US011476003B2

(12) United States Patent
Campbell et al.

(10) Patent No.: US 11,476,003 B2
(45) Date of Patent: Oct. 18, 2022

(54) METHOD FOR PREDICTING RISK OF UNFAVORABLE OUTCOMES, E.G., IN COVID-19 HOSPITALIZATION, FROM CLINICAL CHARACTERISTICS AND BASIC LABORATORY FINDINGS

(71) Applicant: BIODESIX, INC., Boulder, CO (US)

(72) Inventors: Thomas Campbell, Thornton, CO (US); Robert W. Georgantas, III, Broomfield, CO (US); Heinrich Röder, Steamboat Springs, CO (US); Joanna Röder, Steamboat Springs, CO (US); Laura Maguire, Boulder, CO (US)

(73) Assignee: BIODESIX, INC., Boulder, CO (US)

( * ) Notice: Subject to any disclaimer, the term of this patent is extended or adjusted under 35 U.S.C. 154(b) by 0 days.

(21) Appl. No.: 17/344,352

(22) Filed: Jun. 10, 2021

(65) Prior Publication Data
US 2022/0189638 A1    Jun. 16, 2022

Related U.S. Application Data

(60) Provisional application No. 63/125,527, filed on Dec. 15, 2020.

(51) Int. Cl.
*G16H 50/30* (2018.01)
*G16H 40/20* (2018.01)
*G16H 10/60* (2018.01)
*G16H 50/20* (2018.01)

(52) U.S. Cl.
CPC ............. *G16H 50/30* (2018.01); *G16H 10/60* (2018.01); *G16H 40/20* (2018.01); *G16H 50/20* (2018.01)

(58) Field of Classification Search
CPC ........ G16H 50/30; G16H 40/20; G16H 10/60; G16H 50/20

USPC .......................................................... 705/2
See application file for complete search history.

(56) References Cited

U.S. PATENT DOCUMENTS 7,332,294 B2    2/2008 Kelvin et al.
7,736,905 B2    6/2010 Röder et al.
(Continued)

FOREIGN PATENT DOCUMENTS

AU    2020102228 A4    10/2020

OTHER PUBLICATIONS

AlJame et al, "Ensemble learning model for diagnosing COVID-19 from routine blood tests", Informatics in Medicine Unlocked, vol. 21, 10 pages, Oct. 20, 2020.
(Continued)

*Primary Examiner* — Michael Tomaszewski
*Assistant Examiner* — Rachael Sojin Stone
(74) *Attorney, Agent, or Firm* — DLA Piper LLP US

(57) ABSTRACT

A method for predicting an unfavorable outcome for a patient admitted to a hospital, e.g., with a COVID-19 infection is described. Attributes from an electronic health record for the patient are obtained including at least findings obtained at admission, basic patient characteristics, and laboratory data. The attributes are supplied to a classifier implemented in a programmed computer which is trained to predict a risk of the unfavorable outcome. The classifier is arranged as a hierarchical combination of (a) an initial binary classifier stratifying the patient into either a high risk group or a low risk group, and (b) child classifiers further classifying the patient in a lowest risk group or a highest risk group depending how the initial binary classifier stratified the patient as either a member of the high risk or low risk group. The initial binary classifier is configured as a combination of a trained classification decision tree and a logistical combination of atomic classifiers with drop-out regularization.

10 Claims, 25 Drawing Sheets

(56) References Cited

U.S. PATENT DOCUMENTS

| | | | | |
|---|---|---|---|---|
| 8,433,669 | B2* | 4/2013 | Amini | G06N 20/00 |
| | | | | 706/50 |
| 9,477,906 | B2 | 10/2016 | Röder et al. | |
| 10,489,550 | B2 | 11/2019 | Röder et al. | |
| 2010/0293207 | A1* | 11/2010 | Parthasarathy | H04L 51/212 |
| | | | | 707/738 |
| 2011/0295622 | A1* | 12/2011 | Farooq | G16H 50/70 |
| | | | | 705/3 |
| 2012/0197896 | A1* | 8/2012 | Li | G06F 16/313 |
| | | | | 707/740 |
| 2015/0050308 | A1* | 2/2015 | van der Hoek | C07K 14/005 |
| | | | | 424/186.1 |
| 2015/0102216 | A1* | 4/2015 | Roder | H01J 49/26 |
| | | | | 250/282 |
| 2019/0242894 | A1 | 8/2019 | Oved et al. | |
| 2020/0400668 | A1* | 12/2020 | Eden | G01N 33/569 |
| 2022/0059242 | A1* | 2/2022 | Schneider | G16H 10/65 |

OTHER PUBLICATIONS

Bird et al, "Country-level pandemic risk and preparedness classification based on COVID-19 data: A machine learning approach", PLOS One, pp. 1-20, Oct. 28, 2020.

Burdick et al, "Prediction of respiratory decompensation in Covid-19 patients using machine learning: The READY trial", Computers in Biology and Medicine, vol. 124, 6 pages, Aug. 6, 2020.

Chen et al, "An Interpretive Machine Learning Framework for Accurate Severe vs Non-Severe COVID-19 Clinical Type Classification", medRxiv, 23 pages, May 22, 2020.

Higuchi et al, "Early Clinical Factors Predicting the Development of Critical Disease in Japanese Patients with COVID-19: A Single-Center Retrospective, Observational Study", medRxiv, 25 pages, Jul. 30, 2020.

Roder et al, "A dropoout-regulized classifier development approach optimized for precision medicine test discovery from omics data", BMC Bioinformatics, vol. 20, No. 325, 14 pages, (2019).

Roder et al, "Robust indentification of molecular phenotypes using semi-supervised learning", BMC Bioinformatics, vol. 20, No. 273, 25 pages, (2019).

Tulyakov et al, "Review of Classifier Combination Methods", Studies in Computational Intelligence (SCI), vol. 90, pp. 361-386, (2008).

Van der Schaar et al, "How artificial intelligence and machine learning can help healthcare systems respond to COVID-19", Cambridge Centre for AI in Medicine, Mar. 27, 2020.

Xu et al, "Risk Factors Analysis of COVID-19 Patients with ARDS and Prediction Based on Machine Learning", Research Square, 25 pages, Sep. 16, 2020.

International Search Report and Written Opinion issued in PCT/US2021/063560 dated Jan. 19, 2022 (10 pages).

* cited by examiner

ROC Curve for the Binary Classifier Predicting Any Complication

ROC Curve for the Binary Classifier Predicting ARDS

ROC Curve for the Binary Classifier Predicting Intubation

ROC Curve for the Low Risk and High Risk Child Classifiers

FIG. 14 Results Schematic for the Hierarchical Classifier Predicting ICU Admission ROC Curve for the Intermediate Grandchild Classifier Results Schematic for the Hierarchical Classifier Predicting Predicting Intubation

METHOD FOR PREDICTING RISK OF UNFAVORABLE OUTCOMES, E.G., IN COVID-19 HOSPITALIZATION, FROM CLINICAL CHARACTERISTICS AND BASIC LABORATORY FINDINGS

PRIORITY

This application claims priority benefits of U.S. Provisional Application 63/125,527 filed on Dec. 15, 2020. The entire content of the '527 application, including appendices, is incorporated by reference herein.

BACKGROUND

This disclosure is directed to a classifier generation method and related computer-implemented tests that make predictions of risk of unfavorable outcomes for a patient admitted to a hospital. The predictions are made from attributes in the form of clinical data, such as emergency department findings and basic patient data (age, sex or gender, weight, race), and laboratory data associated with the patient. This document sets forth one particular application of the method and tests, namely tests related to predictions of risk of unfavorable outcomes for patients infected with the SARS-CoV-2 virus. However, the classifier generation methods can be used to develop to tests in other scenarios in the health/hospitalization setting, including risks related to patients with influenza and other maladies.

The SARS-CoV-2 virus, also known as the novel coronavirus, is responsible for the current worldwide pandemic. A substantial proportion of people infected with the virus sometimes need care in a hospital setting in order to treat various manifestations of the disease caused by the virus, known as COVID-19, and hopefully save the lives of such patients. These manifestations of COVID-19 presented at the time of hospital admission, typically in the emergency department of a healthcare facility, include difficulty breathing, shortness of breath, fever, extreme fatigue, and coughing, among others.

Given the number of patients infected with the virus, hospitals in hard-hit regions, including the United States and elsewhere, face a daunting task of treating a large number of patients with limited nursing and physician staff, and physical resources, including emergency department and ICU beds, ventilators, medicines approved for treatment of COVID-19, and personal protective equipment. At some point, many hospitals face scarcity triage decisions for allocation of precious and scarce resources. Hence, there is a need for stratification of risk of unfavorable outcomes in COVID-19 patients in the hospital setting in order to effectively manage such resources. For example, patients classified in the lowest risk group according to the tests of this disclosure could be considered for more observation-only based treatment approaches and be candidates for early release, whereas patients classified in the highest risk groups might be candidates for more aggressive early treatment. Administrators presented with the risk predictions of this disclosure may then more effectively allocate their resources to those with the highest risk of unfavorable outcomes.

Even after vaccines for the SARS-CoV-2 virus have become available and some segment of the population has been vaccinated, the need for risk stratification for hospitalized patients will continue to be present, due to such factors as the continued presence of groups within the population who are not vaccinated or otherwise not immune, the infectiousness and ease by which the virus spreads from person to person, the failure of large segments of the population to adopt mitigation measures such as social distancing or mask wearing, and the emergence of new variants to the virus which are even more infectious or resistant to current vaccines. Moreover, the benefits of the tests of this disclosure will apply in the event that new pandemics emerge.

SUMMARY

This document describes a set of practical tests based on machine learning classifiers which can predict the level of risk for a patient presented at a hospital for treatment of COVID-19 of an unfavorable outcome. The predictions are made by a set of classifiers described in this document which are implemented in a programmed computer. The predictions are made from basic patient characteristics, emergency department findings and laboratory data or values obtained at presentation (admission) to the hospital, such findings and laboratory data are typically present in an electronic health record for the patient.

As will be explained below, classifiers are trained to predict risk of specific unfavorable outcomes, including the following: ICU admission, any complication, acute respiratory distress syndrome (ARDS), and intubation. The classifiers could be trained to predict risk of other unfavorable outcomes, including but not limited to mortality.

The method of this disclosure has many practical applications, in terms of both managing care for the patient as well as managing scare hospital resources (space, staff, medicine and equipment) during the pandemic. As noted above, and as an example, patients classified in the lowest risk group could be considered for more observation-only based treatment approaches and be candidates for early release, while patients classified in the highest risk groups might be candidates for more aggressive early treatment. Should hospital resources become limited, determining which patients are at high or low risk for severe disease as they enter the hospital could assist in scarcity triage decisions. Moreover, the methods of this disclosure lend themselves to being performed for all COVID-19 patients in the healthcare facility, so that the risk assessments can be made for the healthcare facility as a whole, as well as manage the care of all the COVID-19 patients.

In one specific embodiment, a method is provided for predicting an unfavorable outcome for a patient admitted to a hospital with a COVID-19 infection. The method includes the steps of:

a) obtaining attributes from an electronic health record for the patient comprising at least findings obtained at hospital admission (e.g., temperature, heart rate, systolic and diastolic blood pressure, respiratory rate and oxygen saturation), basic patient characteristics, and laboratory data (e.g. creatinine, hemoglobin, anion gap, platelet count, sodium, potassium, etc. values), and b) supplying the attributes obtained in step a) to a classifier trained to predict a risk of the unfavorable outcome. The classifier is arranged as a hierarchical combination of (a) an initial binary classifier using the attributes to stratify the patient into either a high risk group or a low risk group, and (b) child classifiers (which are also typically binary in nature) further using the attributes to stratify the patient in a lowest risk group or a highest risk group, depending how the binary classifier stratified the patient as either a member of the high risk or low risk group. The binary classifier is configured as a combination of a trained classification decision tree, or forest of such trees, and a logistical combination of atomic classifiers with drop-out regularization. In this document we use the term "atomic" classifiers to mean classifiers (e.g., k-nearest neighbor classifiers) that use a small number of individual attributes to generate a classification, such as 1 attribute, any possible combination of 2 attributes, or any possible combination of 3 attributes (parameter "s" in the following discussion). The atomic classifiers (also known as "mini-classifiers") are combined using extreme dropout as a regularization technique and logistic regression in the manner described in prior patents of the Assignee, including the patent of Heinrich and Joanna Röder, entitled "Classification generation method using combination of mini-classifiers with regularization and uses thereof," U.S. Pat. No. 9,477,906, the content of which is incorporated by reference here. See also, *A Dropout-Regularized Classifier Development Approach Optimized for Precision Medicine Test Discovery from Omics Data*, Roder et al., BMC Bioinformatics. 2019; 20:325 and *Robust Identification of Molecular Phenotypes using Semi-Supervised Learning*, Roder et al., BMC Bioinformatics. 2019; 20:273, the content of which is incorporated by reference herein. See also the description of other patents of Biodesix, e.g. U.S. Pat. No. 10,489,550 (description of FIG. 1 thereof).

The child classifiers are configured as a logistical combination of atomic classifiers with drop-out regularization, as explained in the above documents and in the following description.

The binary classifiers and the child classifiers are trained from a development set consisting of data from electronic health records for a multitude of hospitalized COVID-19 patients including at least findings obtained at admission (e.g., from an emergency department), basic patient characteristics, and laboratory data for each of the patients. Optionally, the attributes used for classification can include other clinical or patient attributes, such as, comorbidities, and symptoms presented at admission, provided that they are also available for all or most of the patients in the development set.

In one configuration, the method includes the step of training a set of binary and child classifiers to predict each of ICU admission, acute respiratory distress syndrome, any complication, and intubation from emergency department findings, basic patient characteristics, and laboratory data for a COVID-19 patient, and performing step b) iteratively using the trained set of binary and child classifiers to thereby predict the risk of each of ICU admission, acute respiratory distress syndrome, any complication, and intubation of the patient.

In one possible implementation, the patient health record may be missing an attribute which was used in development of the binary or child classifiers, in this implementation the additional step may be performed of predicting the one or more missing attributes.

In one embodiment, the initial binary and child classifiers are developed from attributes which are inclusive of the attributes presented in the health record for the patient. In another embodiment, the findings obtained at admission for the patient are in a binary format and wherein the initial binary and child classifiers are developed from attributes in the form of findings obtained at admission in the development set which are converted into the binary format.

In another aspect, a computer system is provided which implements trained classifiers to predict risk of an unfavorable outcome for a hospitalized COVID-19 patient from attributes from an electronic health record for the patient comprising at least findings obtained at hospital admission, basic patient characteristics, and laboratory data. The computer system includes a memory storing parameters of an initial binary classifier stratifying the patient into either a high risk group or a low risk group, and child classifiers further classifying the patient in a lowest risk group or a highest risk group depending how the binary classifier stratified the patient as either a member of the high risk or low risk group, b) a processor implementing program code executing the binary and child classifiers on the attributes in a hierarchical manner, wherein the binary classifier is configured as a combination of a trained classification decision tree and a logistical combination of atomic classifiers with drop-out regularization, and wherein the child classifiers are configured as a logistical combination of atomic classifiers with drop-out regularization, and c) code for generating an output from one of the child classifiers.

In still another aspect, a method of triaging resources of a healthcare facility for treating COVID-19 patients is described. The method includes the steps of screening COVID-19 patients admitted to the healthcare facility for risk of unfavorable outcomes using the method or computer system as described above, and b) adjusting the allocation of one or more resources within the hospital based on the results of the screening step a). In one embodiment, the steps a) and b) are repeated, such as for all COVID-19 patients in the healthcare facility, e.g., upon admission to the hospital or healthcare facility.

In still another aspect, a method is disclosed for developing a classifier for predicting risk of an unfavorable outcome of a patient admitted to a hospital. The method includes the steps of: a) obtaining a development set comprising data from electronic health records for a multitude of patients admitted to one or more hospitals, wherein the electronic health records include laboratory data, findings obtained at hospital admission, and clinical data including basic patient characteristics and outcome data indicating whether or not the unfavorable outcome occurred during hospitalization of the patients; b) training an initial binary classifier from the development set to stratify members of the development set into high and low risk groups; c) training one or more child classifiers to further stratify high and low risk groups into at least highest and lowest risk groups; and d) configuring a test for predicting risk of unfavorable outcome as a hierarchical combination of the binary classifier and the one or more child classifiers. The binary classifier is configured as a combination of a trained classification decision tree (or forest of trees) and a logistical combination of atomic classifiers with drop-out regularization, and the child classifiers are configured as a logistical combination of atomic classifiers with drop-out regularization. In one embodiment, the patient is infected with the SARS-CoV-2 virus. However, the methods are applicable more generally, for example the patient is an influenza patient.

BRIEF DESCRIPTION OF THE DRAWINGS

FIG. 6 is that in the hierarchical arrangement one of the child classifiers is an intermediate classifier that generates intermediate classification results ("low risk" and "high risk"). This intermediate classifier could be considered a "grandchild" classifier since it further stratifies risk groups classified by the child classifiers above it in the hierarchy.

DETAILED DESCRIPTION

Overview

Figure 1:
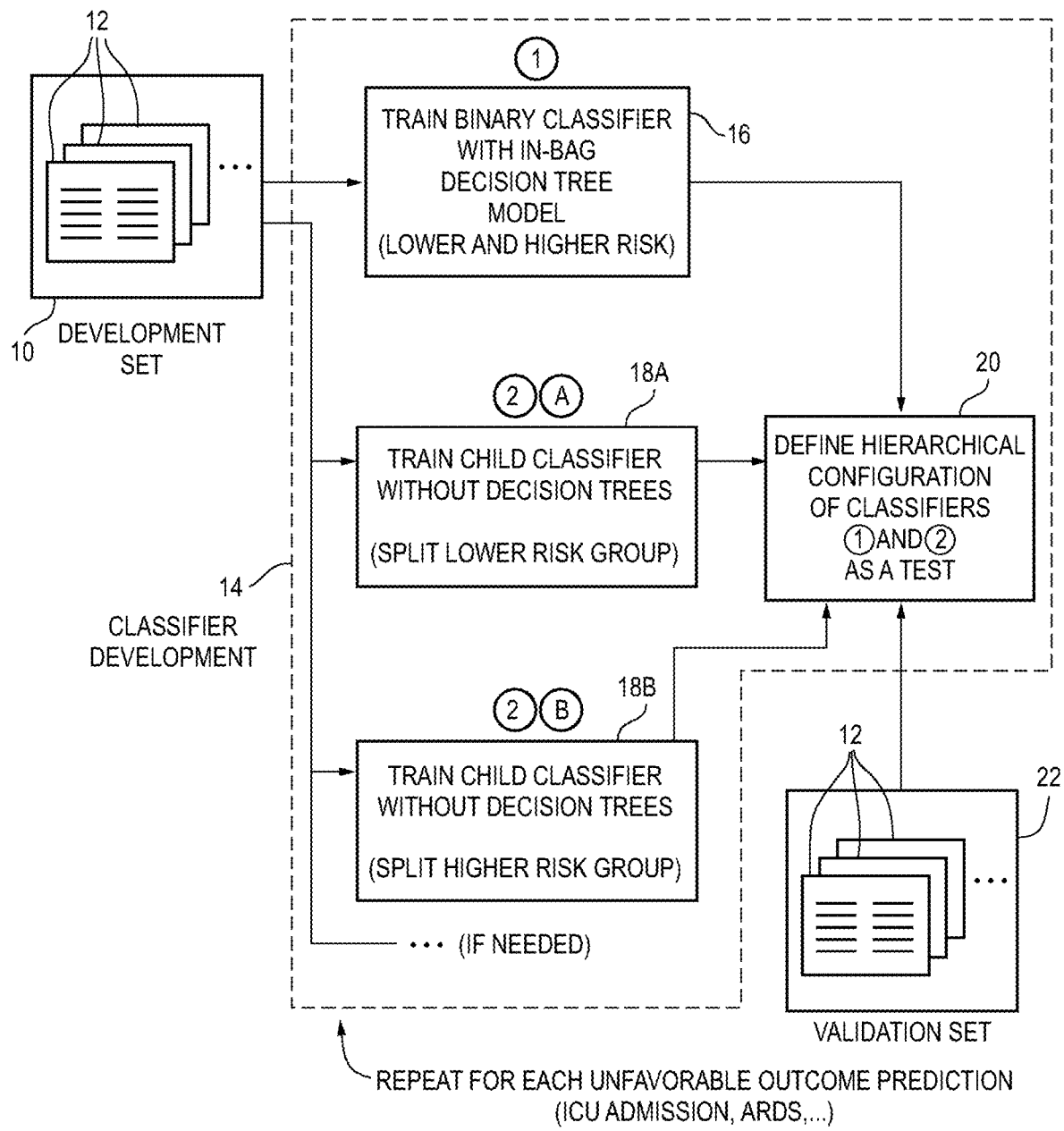
FIG. 1 is an illustration of a classifier development process in which binary and child classifiers are developed from a development set; a test in the form of a hierarchical combination of the binary and child classifiers is then defined. The process of FIG. 1 is performed independently to generate binary and child classifiers for specific endpoints or unfavorable outcomes, such as ARDS, intubation, ICU admission or other complications for hospitalized COVID-19 patients.
Figure 2:
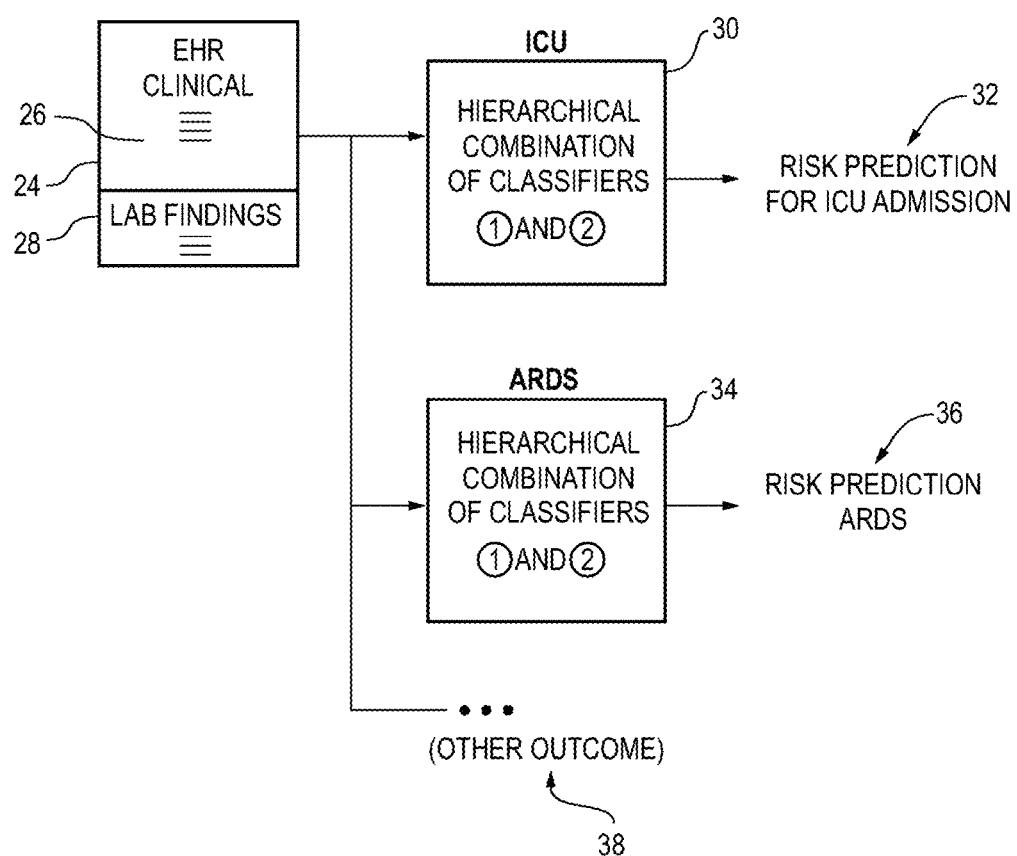
FIG. 2 is an illustration of a testing process using the test defined by the process of FIG. 1 to produce a risk of unfavorable outcome.
Figure 3:
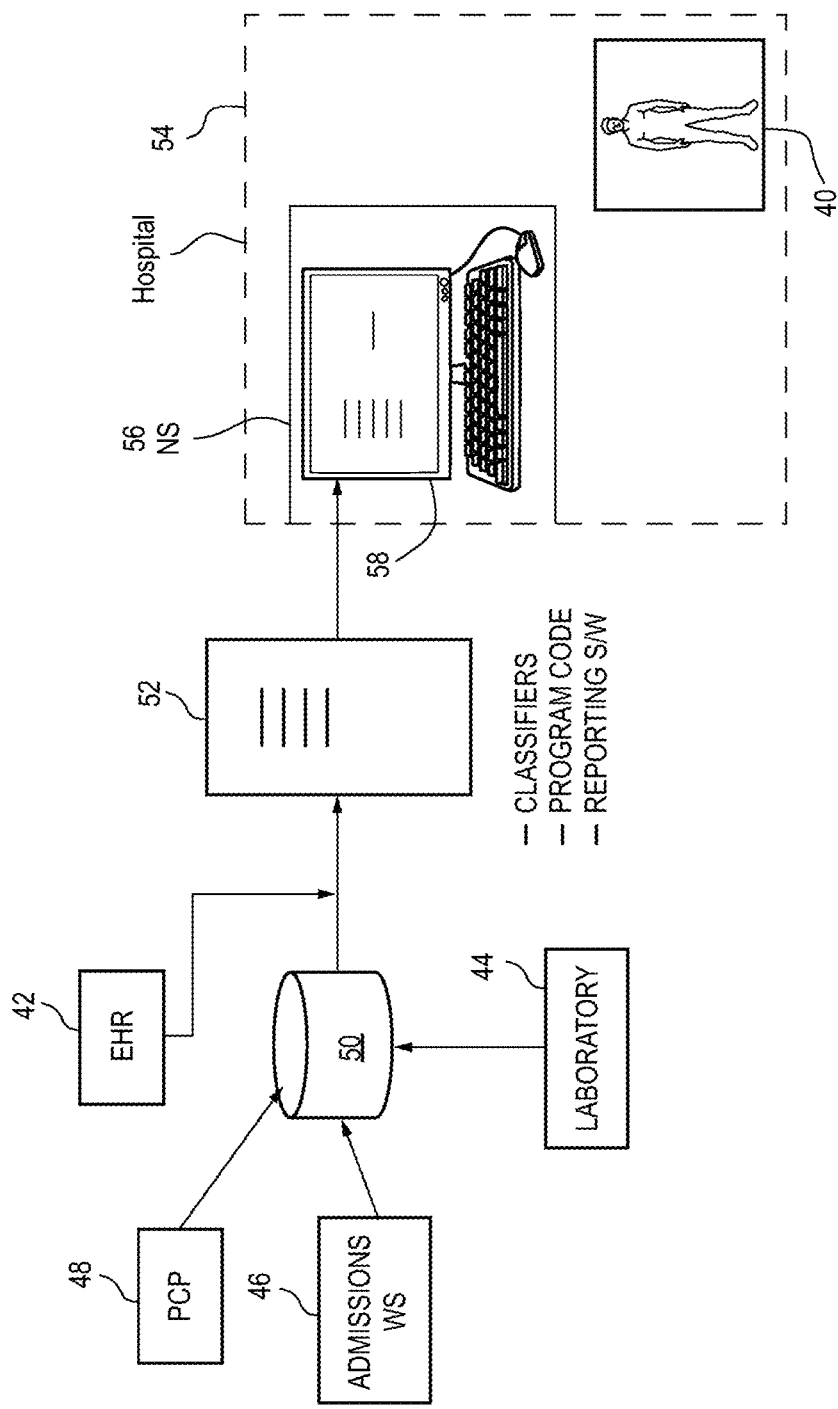
FIG. 3 is an illustration of one possible practical implementation of the test of FIG. 2 in a computing environment of a healthcare facility.
Figure 4:
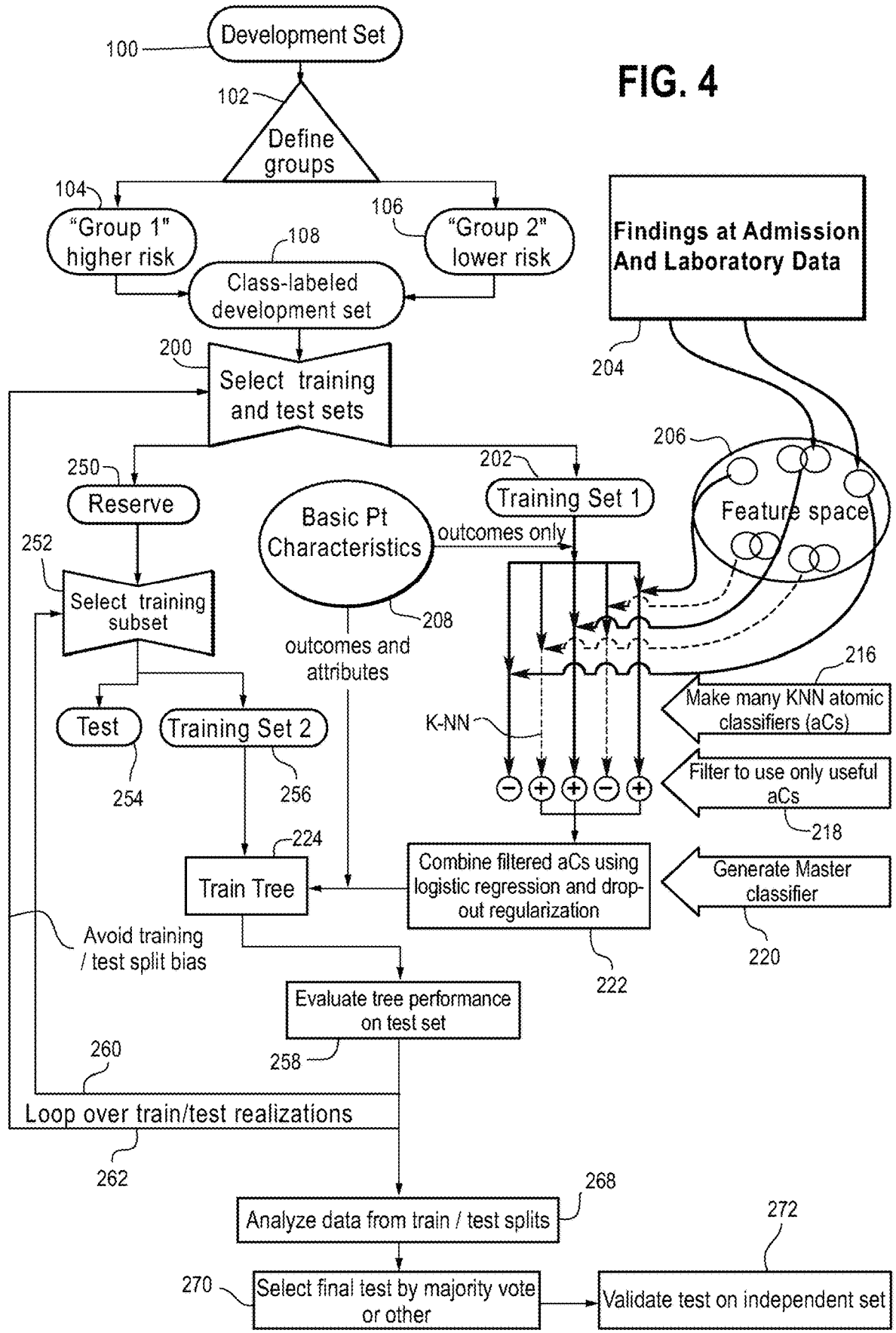
FIG. 4 is an illustration of a classifier development process for developing the binary classifiers of FIG. 1.
Figure 5:
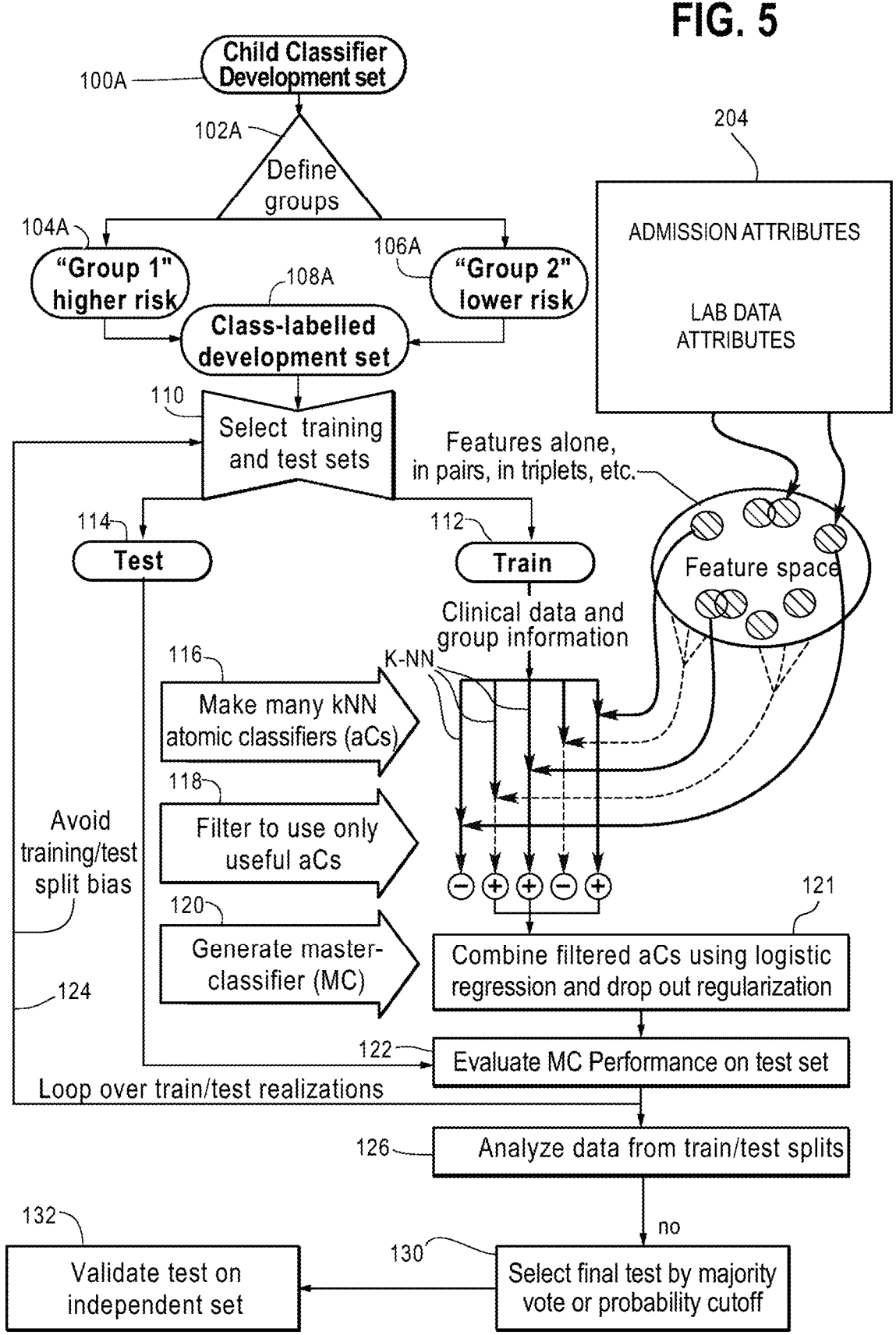
FIG. 5 is an illustration of a classifier development process for developing the child classifiers of FIG. 1.
Figure 6:
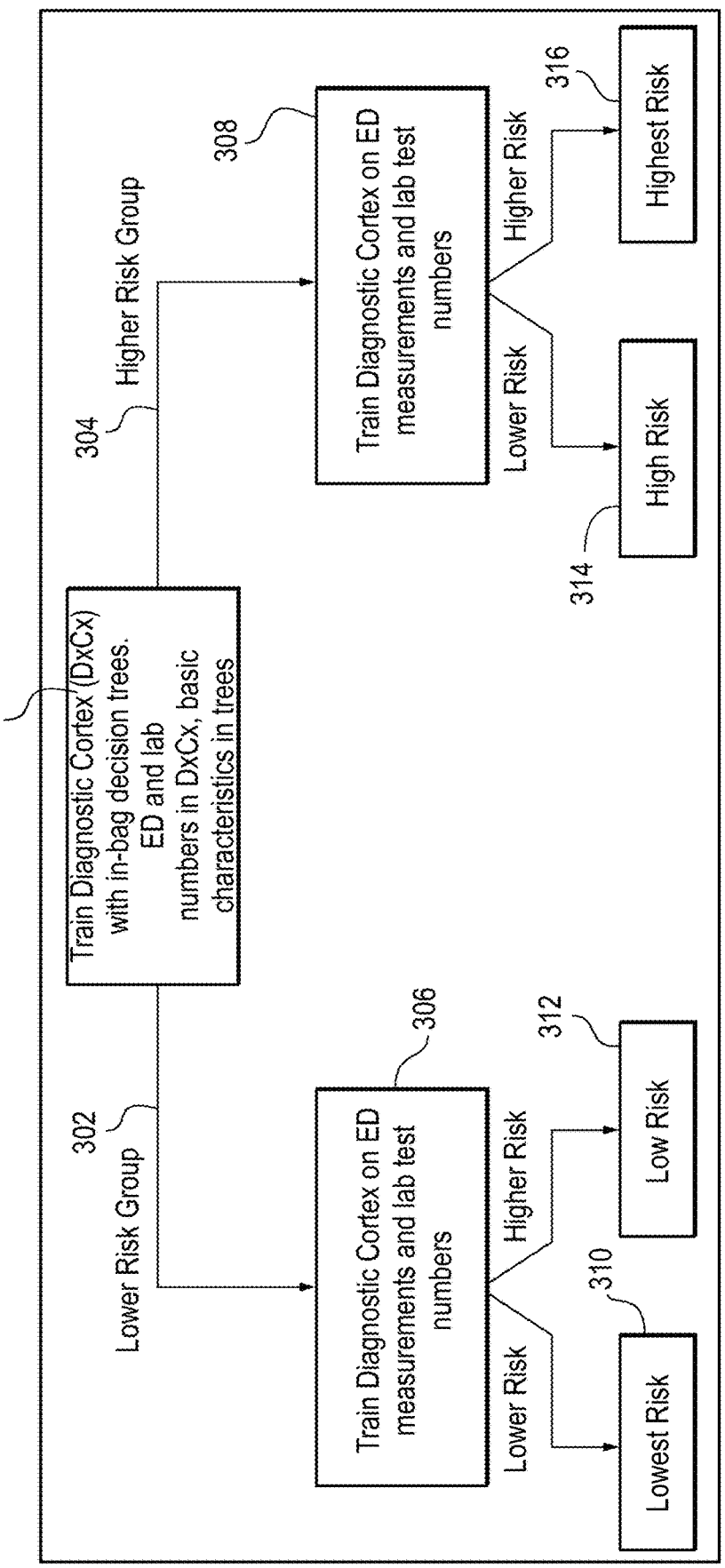
FIG. 6 is an illustration of one possible hierarchical combination of one initial binary classifier and two child classifiers, one stratifying the lower risk group (from the binary classifier) into lowest and low risk groups, and the other stratifying the higher risk group (from the binary classifier) into lower and highest risk groups.
Figure 7:
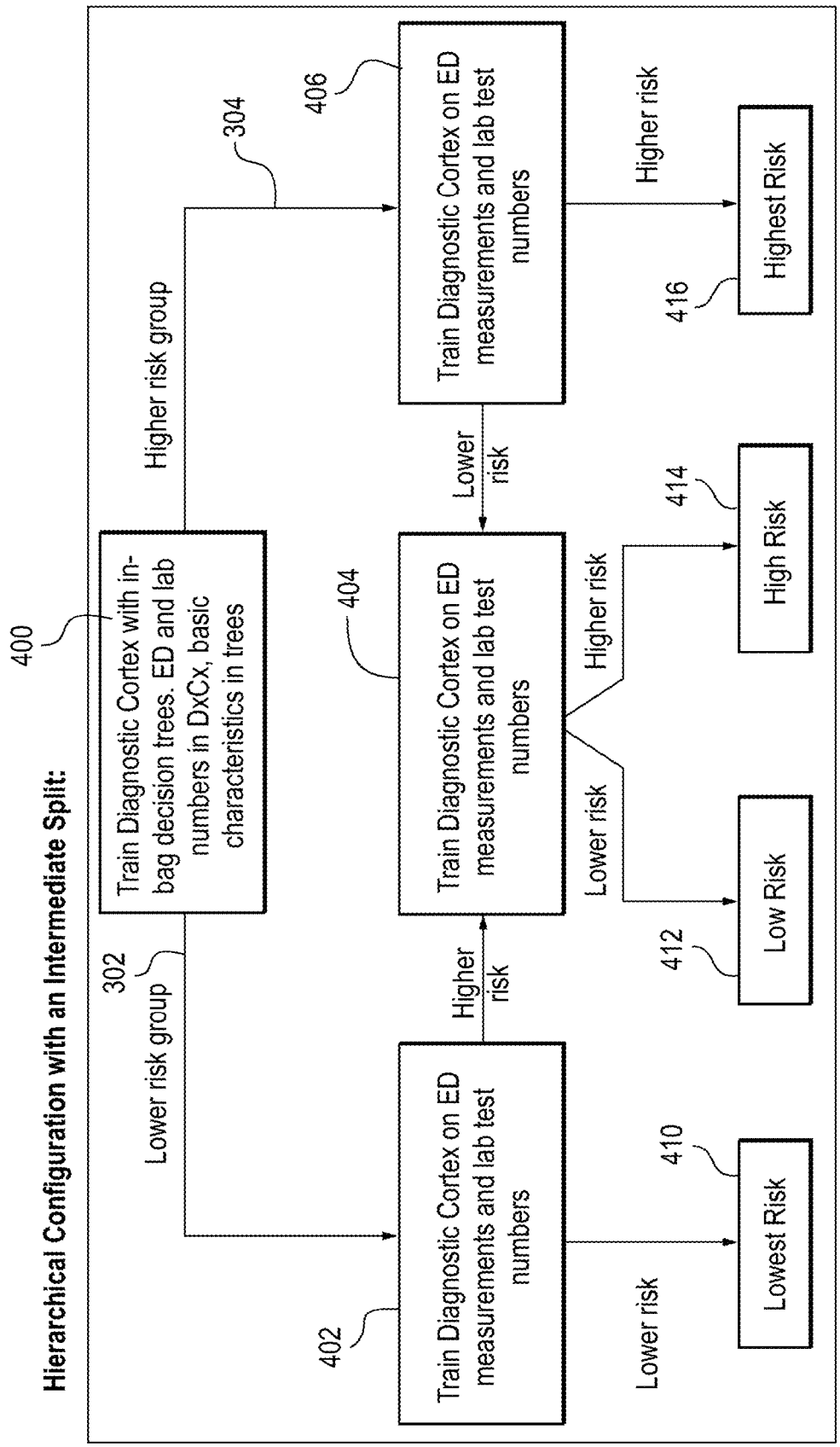
FIG. 7 is an illustration of a hierarchical combination of one binary and three child classifiers. The difference between FIG. 7

An overview of the classifier development process we used is shown in FIG. 1. FIG. 2 shows a procedure for using the classifiers or test trained in accordance with FIG. 1 to generate a prediction in the form of risk of adverse outcome for a COVID-19 patient. FIG. 2 will be explained later in conjunction with FIGS. 22 and 23. FIG. 3 shows a practical embodiment of a computer system for performing the test of FIG. 2. Details of the binary classifier training procedure are shown in FIG. 4, and details of the child and intermediate classifier training procedure are shown in FIG. 5. FIGS. 6 and 7 show two possible ways in which the binary, child and optionally intermediate classifiers can be combined as a test for risk of unfavorable outcome. FIGS. 8-21 shows specific results and configurations of binary and child/intermediate classifiers for the specific unfavorable outcomes in the COVID-19 context.

Referring again to FIG. 1, binary and child/intermediate classifiers are developed from a development set 10 in the form of patient anonymized electronic health record data 12 from a multitude of patients, in this case, hundreds of patients hospitalized with COVID-19 at one or more healthcare facilities. The electronic health record data includes at least laboratory data and findings obtained at hospital admission (e.g., from the emergency department), basic patient characteristics (e.g., age, gender or sex, weight, race), and outcomes. The electronic health record data optionally includes other data, such as clinical data, comorbidities, etc. The specifics of the development set we used for developing the classifiers of this disclosure is described in detail below.

As indicated at 14, this development set 10 was used in a classifier development process that included developing and training several different classifiers: 1) an initial binary classifier 16 trained to stratify the patients in the development set into high and low risk groups, and 2) one or more child or intermediate classifiers 18A, 18B . . . that further stratify the high and low risk groups into lowest and highest risk groups and optionally intermediate risk groups.

After training, these classifiers are then combined in a hierarchical manner (see FIGS. 6 and 7) and at step 20 a test is defined from this hierarchy, see e.g., FIG. 14, 16, 19 or 21. In particular, the patient electronic health record data (laboratory data and emergency department findings, and basic patient characteristics) are classified first by the initial binary classifier which assigns the patient data to either a high or low risk group, and then one or more of the child classifiers further classify the patient into lowest or highest risk groups or intermediate risk groups, as shown in FIGS. 6 and 7 or in the specific hierarchies of FIG. 14, 16, 19 or 21. Hence, this test basically consists of execution of the classification procedure of the initial binary and child (and optionally intermediate) classifiers, and program logic that selects one of the child classifiers to further classify the patient into lowest or highest risk groups (or optionally an intermediate classification label) and program code that generates an output for the test, e.g. "high risk of ICU admission", "low risk of intubation," etc.

It will be appreciated that the classifier generation procedure 14 of FIG. 1 is repeated independently for each different outcome that the classifiers are trained to predict. For example, the procedure of FIG. 1 is performed once for ARDS risk prediction, and then again for intubation risk prediction, etc. Each training process is the same, except that during training the classification label that is used for training is the specific outcome the test is designed for. After training, these trained classifiers (including program code, parameters, etc.) are stored in computer memory and used later to classify a patient from the laboratory data and emergency department findings, and optionally other clinical data or basic patient characteristics in the patient's electronic health record data. As shown at 22, a validation set consisting of a multitude of electronic health records 12 for a previously unseen set of patients is used to test or validate the performance of the classifiers trained in accordance with the procedure of FIG. 1. We have performed this validation work on the classifiers of this disclosure, details of which are set forth in Appendix A of our prior provisional application, Ser. No. 63/125,527.

Still referring to FIG. 1, as will be explained in more detail below, the binary classifiers of this disclosure have preferred architecture and arrangement. In particular, the binary classifier 16 is configured as a combination of a trained random classification decision tree (or forest of such trees) and a logistical combination of atomic classifiers with drop-out regularization. This configuration will be explained in greater detail in conjunction with FIGS. 4 and 22. The child and intermediate classifiers 18A, 18B are configured as a logistical combination of atomic classifiers with drop-out regularization, as will be explained in greater detail in conjunction with FIGS. 5 and 23, and do not use the decision trees in preferred embodiments. Note also that the child and intermediate classifiers are trained using subsets of the development set, as will be explained in more detail below.

FIG. 2 is an illustration of a testing process using the test defined by the process 20 of FIG. 1 to produce a risk of unfavorable outcome. An electronic health record 24 for the patient X is obtained, which includes findings obtained at admission, basic patient characteristics, laboratory data 28, and optionally other clinical data 26. This data is supplied to a classifier 30 which takes the form of a hierarchical combination of the binary classifier (16, FIG. 1) and the child classifiers (18A, 18B, FIG. 1). A classification procedure is then performed on the data in the electronic health record, producing a prediction 32 in the form of risk of unfavorable outcome, e.g., risk of ICU admission. In the preferred situation where four different classifiers are trained to predict four different unfavorable outcomes, the electronic health record data is supplied to each of the classifiers trained to predict such outcomes, such as the ICU admission classifier 30, the ARDS classifier 34, and the other classifiers trained to predict risk of any complication and intubation, indicated at 38, generating a risk prediction for ICU admission 32, a risk prediction for ARDS 36, and risk predictions for risk of any other unfavorable outcomes, such as any complication and intubation. The test performed in accordance with FIG. 2 can be performed at the time of admission or during the hospitalization stay. Additionally, the test of FIG. 2 could be performed for all COVID-19 patients in the healthcare facility, e.g., upon admission.

FIG. 3 is an illustration of a computing environment in which the method of FIG. 2 can be practiced. The healthcare facility (or some other network entity) includes a data store 50 which stores electronic health record data for a patient, such as data obtained in a laboratory 44, clinical, basic patient characteristics, or other data obtained from a workstation in the admissions or emergency department or other facility upon admission 46, data from the patient's primary care physician, 48 etc. This data is consolidated into an electronic health record 42 which is supplied to a general purpose computer 52 that implements the classifiers of this disclosure, including program code, logic combining classifiers in a hierarchical manner as shown in FIG. 6 or 7, reporting software, stored parameters, etc. This computer 52 generates the predictions as explained in this document and supplies them to a workstation 58 in the healthcare facility (e.g., hospital 54) which is treating the patient 40. This workstation 58 could be at the nurses' station 56 where the predictions are available to the healthcare providers treating the patient. Alternatively, the predictions could be provided to hospital administrators or physicians that are responsible for allocation of hospital resources or making resource triage decisions.

Having now described an overview of the training and use of the classifiers of this disclosure, the following sections will describe in more detail the development set we used to develop the classifiers for COVID-19 patient prediction of unfavorable outcomes in a hospital setting, as well as more detail on the binary and child classifiers.

Development Set The development set for the classifiers presented here consisted of electronic health record data for 229 hospitalized COVID-19 patients. Within this health record data were "features" or "attributes" which were used for generating the classifications. The terms "features" and "attributes" are used interchangeably in this document. The attributes are grouped into three types: baseline or basic patient characteristics, findings obtained at hospital admission, e.g., from the emergency department (ED) (numbers), and laboratory data (numbers). They are summarized in tables 1-3. Four endpoints were considered for training classifiers; they are listed in table 4. Selected attributes of the development set are summarized in tables 5 and 6. For categorical attributes, the number and proportion for each observed class are given, and for numeric attributes, the mean, median and inter-quartile range are given.

TABLE 1

Baseline Patient Characteristics Attributes

| | |
|---|---|
| Race or Ethnicity | age |
| weight_kg | sex_or_gender |

TABLE 2

Attributes obtained at Hospital admission (e.g. from ED)

| | |
|---|---|
| ed_temperature_c | ed_diastolic_bp |
| ed_heart_rate | ed_respiratory_rate |
| ed_systolic_bp | ed_oxygen_saturation |

TABLE 3

Lab Data Attributes

| | | | |
|---|---|---|---|
| initial_qtc | bun | wbc_scree | initial_ldh |
| sodium | creatinine | hemoglobin | initial_d_dimer |
| potassium | egfr | hematocrit | initial_c_reactive_protein |
| carbon_dioxide_bicarb | anion_gap | platelet_co | ferritin |

TABLE 4

Endpoints

| | |
|---|---|
| admitted_to_icu | Complications during hospitalization? (choice = ARDS) |
| intubated | Complications during hospitalization? (choice = Any) |

TABLE 5

Summary of Selected Categorical Attributes in the Development Set

| Attribute | Class | Development Set n (proportion of group) |
|---|---|---|
| | Race | |
| | Race or Ethnicity (choice = White) | 41 (0.179) |
| | Race or Ethnicity (choice = Black or African American) | 52 (0.227) |
| | Race or Ethnicity (choice = Hispanic or Latino) | 94 (0.410) |
| | Race or Ethnicity (choice = Other) | 31 (0.135) |
| | Race or Ethnicity (choice = Unknown) | 11 (0.048) |
| | sex or gender | |
| | Male | 124 (0.541) |
| | Female | 105 (0.459) |
| | Comorbidities (choice = None) | |
| | 0 | 191 (0.834) |
| | 1 | 38 (0.166) |
| | Comorbidities (choice = Hypertension) | |
| | 1 | 100 (0.437) |
| | 0 | 129 (0.563) |
| | Comorbidities (choice = Hyperlipidemia) | |
| | 0 | 182 (0.795) |
| | 1 | 47 (0.205) |
| | Comorbidities (choice = Type 2 Diabetes) | |
| | 0 | 147 (0.642) |
| | 1 | 82 (0.358) |
| | Comorbidities (choice = Cardiovascular Disease) | |
| | 0 | 203 (0.886) |
| | 1 | 26 (0.114) |

TABLE 5-continued

Summary of Selected Categorical Attributes in the Development Set

| Attribute | Class | Development Set n (proportion of group) |
|---|---|---|
| Comorbidities (choice = Respiratory Disease) | | |
| | 0 | 180 (0.786) |
| | 1 | 49 (0.214) |
| Comorbidities (choice = Gastrointestinal Disease) | | |
| | 0 | 200 (0.873) |
| | 1 | 29 (0.127) |
| Comorbidities (choice = Renal Disease) | | |
| | 0 | 205 (0.895) |
| | 1 | 24 (0.105) |
| Comorbidities (choice = Endocrine Disease (Excluding Diabetes)) | | |
| | 0 | 214 (0.934) |
| | 1 | 15 (0.066) |
| Comorbidities (choice = Neurologic Disease) | | |
| | 0 | 194 (0.847) |
| | 1 | 35 (0.153) |
| Comorbidities (choice = Psychiatric Disease) | | |
| | 0 | 204 (0.891) |
| | 1 | 25 (0.109) |
| Comorbidities (choice = Cancer) | | |
| | 0 | 212 (0.926) |
| | 1 | 17 (0.074) |
| Comorbidities (choice = Infectious Disease) | | |
| | 0 | 221 (0.965) |
| | 1 | 8 (0.035) |
| Comorbidities (choice = Autoimmune Disease) | | |
| | 0 | 222 (0.969) |
| | 1 | 7 (0.031) |
| Comorbidities (choice = Arthritis) | | |
| | 0 | 213 (0.930) |
| | 1 | 16 (0.070) |
| Comorbidities (choice = Chronic Pain Syndrome) | | |
| | 0 | 218 (0.952) |
| | 1 | 11 (0.048) |
| Comorbidities (choice = Morbid Obesity) | | |
| | 0 | 193 (0.843) |
| | 1 | 36 (0.157) |
| Symptoms at presentation (choice = Shortness of breath) | | |
| | 0 | 85 (0.371) |
| | 1 | 144 (0.629) |
| Symptoms at presentation (choice = Fever) | | |
| | 0 | 79 (0.345) |
| | 1 | 150 (0.655) |
| Symptoms at presentation (choice = Cough) | | |
| | 0 | 57 (0.249) |
| | 1 | 172 (0.751) |
| Symptoms at presentation (choice = AMS/Confusion) | | |
| | 0 | 214 (0.934) |

TABLE 6

Summary of Selected Numeric Attributes in the Development Set

| Attribute | Mean | Median | IQR |
|---|---|---|---|
| age | 56 | 57 | 25 |
| ed_temperature_c | 37 | 37 | 1.0 |
| ed_heart_rate | 99 | 98 | 29 |
| ed_systolic_bp | 140 | 130 | 28 |
| ed_diastolic_bp | 75 | 74 | 18 |
| ed_respiratory_rate | 22 | 20 | 6.0 |
| ed_oxygen_saturation | 90 | 92 | 7.0 |
| weight_kg | 87 | 82 | 28 |
| initial_qtc | 440 | 440 | 37 |
| sodium | 140 | 140 | 4.0 |
| potassium | 3.8 | 3.8 | 0.5 |
| carbon_dioxide_bicarb | 23 | 23 | 4.0 |
| bun | 19 | 13 | 10 |
| creatinine | 1.1 | 0.94 | 0.51 |
| anion_gap | 12 | 12 | 3.0 |
| wbc_screen | 7.9 | 6.8 | 3.7 |
| hemoglobin | 14 | 15 | 2.4 |
| hematocrit | 43 | 44 | 7.0 |
| platelet_count | 220 | 210 | 100 |
| initial_ldh | 360 | 320 | 160 |
| initial_d_dimer | 2200 | 860 | 920 |
| initial_c_reactive_protein | 110 | 83 | 110 |
| ferritin | 820 | 360 | 560 |

Classifier Generation and Training

A. Initial Binary Classifiers

As explained previously in conjunction with FIG. 1, we trained binary classifiers 16 to stratify patients in the development set into high risk and low risk groups (independently for each unfavorable outcome), and then trained what we have termed "intermediate" or "child" classifiers to further stratify these groups into lowest and highest risks groups, or intermediate risk groups. This section will describe these initial binary classifiers.

The binary classifiers represent a novel extension of what we have previously described as the "Diagnostic Cortex" or "Combination of Mini-classifiers with Dropout Regularization" (CMC/D) classifier development methodology platform. This platform is described in FIGS. 4 and 5 below. Full details of the Diagnostic Cortex classification method can be found in Röder et al. U.S. Pat. No. 9,477,906, the content of which is incorporated by reference, and Roder et al., *A Dropout-Regularized Classifier Development Approach Optimized for Precision Medicine Test Discovery from Omics Data, BMC Bioinformatics.* 2019; 20:325 and Roder et al., *Robust Identification of Molecular Phenotypes using Semi-Supervised Learning,* Roder et al., *BMC Bioinformatics.* 2019; 20:273. The extension we describe here is the inclusion of trained random classification decision trees in addition to the combination of mini-classifiers with dropout regularization, as will be explained below in conjunction with FIG. 4.

For this project, the feature space 206 consists of findings at admission typically from the emergency department (table 2) and basic laboratory (bloodwork) numeric features (table 3) for all the members of the development set as shown at 204. The clinical attributes passed to the trees were the basic patient characteristics 208 (table 1).

Referring in particular to the procedure of FIG. 4, the development set is shown at 100 and at step 102 we define two classes, a "group1" or higher risk class and a "group 2" or lower risk class, based on (human) inspection of the outcome data for the members of the development set. Based on such inspection we assign the class labels to the members of the development set resulting in a class-labeled development set 108. At step 200 we select a training subset, which splits the class labeled development set 108 into a reserve set 250 and a "training set 1" 202. The training set 1 202 is then subject to the combination of atomic classifiers with dropout regularization training procedure explained in the prior patent and articles of Röder et al. cited above. Specifically, at step 216 we create many k-nearest neighbor (k-NN) atomic or mini-classifiers (all individual features, all possible combinations of pairs of features, and all possible combinations of triplets of features in the feature space). At step 218 have an optional filtering step to only retain those mini-classifiers that pass certain performance criteria; however, in the present exercise we did not filter out any of the k-NN mini-classifiers. At step 220, we then generate what we have called a "master classifier" by combining all of the mini-classifiers using logistic regression and drop-out regularization.

In step 216, as noted we construct a multitude of individual mini-classifiers using sets of feature values from the development set up to a pre-selected feature set size s (s=integer 1 . . . p). For example, a multiple of individual mini- (or "atomic") classifiers could be constructed using a single feature (s=1), or pairs of features (s=2), or three of the features (s=3), or even higher order combinations containing more than 3 features. The selection of a value of s will normally be small enough to allow the code implementing the method to run in a reasonable amount of time, but could be larger in some circumstances or where longer code run-times are acceptable. The selection of a value of s also may be dictated by the number of measured variables (p) in the data set, and where p is in the hundreds, thousands or even tens of thousands, s will typically be 1, or 2 or possibly 3, depending on the computing resources available, and was 3 in the present work. The mini-classifiers of step 216 execute a supervised learning classification algorithm, such as k-nearest neighbors (k-NN), in which the values for a feature, pairs or triplets of features of a sample instance are compared to the values of the same feature or features in a training set and the nearest neighbors (e.g., k=11) in an s-dimensional feature space are identified and by majority vote a class label is assigned to the sample instance for each mini-classifier. In practice, there may be thousands of such mini-classifiers depending on the number of features which are used for classification.

As noted, there is an optional filtering step 218. If this step is performed, we test the performance, for example the accuracy, of each of the individual mini-classifiers to correctly classify the sample, or measure the individual mini-classifier performance by some other metric (e.g. the Hazard Ratios (HRs) obtained between groups defined by the classifications of the individual mini-classifier for the training set samples) and retain only those mini-classifiers whose classification accuracy, predictive power, or other performance metric, exceeds a pre-defined threshold to arrive at a filtered (pruned) set of mini-classifiers. The class label resulting from the classification operation may be compared with the class label for the sample known in advance if the chosen performance metric for mini-classifier filtering is classification accuracy. However, other performance metrics may be used and evaluated using the class labels resulting from the classification operation. Only those mini-classifiers that perform reasonably well under the chosen performance metric for classification are maintained in the filtering step 218. Alternative supervised classification algorithms could be used, such as linear discriminants, decision trees, probabilistic classification methods, margin-based classifiers like support vector machines, and any other classification method that trains a classifier from a set of labeled training data.

To overcome the problem of being biased by some univariate feature selection method depending on subset bias, we take a large proportion of all possible features as candidates for mini-classifiers. We then construct all possible k-NN classifiers using feature sets up to a maximum pre-selected size (parameter s). This gives us many "mini-classifiers": e.g. if we start with 100 features for each sample/patient (p=100), we would get 4950 "mini-classifiers" from all different possible combinations of pairs of these features (s=2), 161,700 mini-classifiers using all possible combination of three features (s=3), and so forth. Other methods of exploring the space of possible mini-classifiers and features defining them are of course possible and could be used in place of this hierarchical approach. Of course, many of these "mini-classifiers" will have poor performance, and hence in the filtering step we only use those "mini-classifiers" that pass predefined criteria. These filtering criteria are chosen dependent on the particular problem: If one has a two-class classification problem, one would select only those mini-classifiers whose classification accuracy exceeds a pre-defined threshold, i.e., are predictive to some reasonable degree. Even with this filtering of "mini-classifiers" we end up with many thousands of "mini-classifier" candidates with performance spanning the whole range from borderline to decent to excellent performance.

In the present work we discovered the filtering of the mini-classifiers did not substantially affect performance and therefore in the following discussion of step 220 all mini-classifiers constructed in step 216 were used in the logistic regression and drop-out regularization, and a filtering step 218 was not performed.

The method continues with step 220 of generating a Master Classifier (MC) indicated at 222 by combining the mini-classifiers using a regularized combination method. In one embodiment, this regularized combination method takes the form of repeatedly conducting a logistic training of the set of mini-classifiers to the class labels for the samples. This is done by randomly selecting a small fraction of the mini-classifiers as a result of carrying out an extreme dropout from the set of mini-classifiers (a technique referred to as drop-out regularization herein), and conducting logistic training on such selected mini-classifiers. While similar in spirit to standard classifier combination methods (see e.g. S. Tulyakov et al., *Review of Classifier Combination Methods*, Studies in Computational Intelligence, Volume 90, 2008, pp. 361-386), we have the particular problem that some "mini-classifiers" could be artificially perfect just by random chance, and hence would dominate the combinations. To avoid this overfitting to particular dominating mini-classifiers, we generate many logistic training steps by randomly selecting only a small fraction of the mini-classifiers for each of these logistic training steps. This is a regularization of the problem in the spirit of dropout as used in deep learning theory. In this case, where we have many mini-classifiers and a small training set, we use extreme dropout, where in excess of 99% of filtered mini-classifiers are dropped out in each iteration.

In more detail, the result of each mini-classifier is one of two values, either "Group1" or "Group2" in this example. We can then combine the results of the mini-classifiers by defining the probability P of obtaining a "Group1" label via standard logistic regression (see e.g. http://en.wikipedia.org/wiki/Logistic_regression:

$$P(\text{``Group 1''} | \text{feature values}) = \frac{\exp(\sum_{\text{mini-classifiers}} w_{mc} I(mc(\text{feature values})))}{\text{Normalization}} \quad \text{Eq. (1)}$$

where $I(mc(\text{feature values}))=1$, if the mini-classifier mc applied to the feature values of a sample returns "Group2", and 0 if the mini-classifier returns "Group1". The weights $w_{mc}$ for the mini-classifiers are unknown and need to be determined from a regression fit of the above formula for all samples in the training set using +1 for the left hand side of the formula for the Group2-labeled samples in the training set, and 0 for the Group1-labeled samples, respectively.

As we have many more mini-classifiers, and therefore weights, than members of the training set, typically thousands of mini-classifiers and only tens of members, such a fit will always lead to nearly perfect classification, and can easily be dominated by a mini-classifier that, possibly by random chance, fits the particular problem very well. We do not want our final test to be dominated by a single special mini-classifier which only performs well on this particular set and is unable to generalize well. Hence we designed a method to regularize such behavior: Instead of one overall regression to fit all the weights for all mini-classifiers to the training data at the same time, we use only a few of the mini-classifiers for a regression, but repeat this process many times in generating the master classifier. For example, we randomly pick three of the mini-classifiers, perform a regression for their three weights, pick another set of three mini-classifiers, and determine their weights, and repeat this process many times, generating many random picks, i.e. realizations of three mini-classifiers. The Master Classifier (222, FIG. 4) is then defined as the average of all the dropout realizations. The number of realizations should be large enough that each mini-classifier is very likely to be picked at least once during the entire process. This approach is similar in spirit to "drop-out" regularization, a method used in the deep learning community to add noise to neural network training to avoid being trapped in local minima of the objective function.

The classification output of the logistic regression and drop-out regularization 222 is then supplied along with basic patient characteristics to classification trees 224 which are trained separately in the procedure of the left hand-side of FIG. 4.

In particular, referring again to FIG. 4, the training subset selected at step 200 is split in training set 1 202 (and subject to the procedures explained above) and a reserve set 250. The reserve set is further sampled (30 times for this project) into a set 256 for training (Training Set 2) and a set for evaluation (Test Set 254). The training set 2 (256) is used to train a set of random classification tree classifiers 224, which includes the classification output of the Master Classifier 222 with for samples in Training Set 2 and basic patient characteristics 208. Samples in the evaluation Test Set 254 are not used at all in training and can be used to generate out-of-bag classifications in an evaluation step 258. This process of selecting training subsets and splitting into test and training set 2 subsets is performed many times as represented by the inner loop 260, such as 30 times in this example. Furthermore, the procedure of training the classification trees 224 and generating master classifiers 222 is performed for many different training/test split realizations as indicated by the outer loop 262, for example 625 times in this example.

At step 268 we analyze the classification performance data from the many different training and test splits (step 200 and iterations through loop 262) and at step 270 we select a final test or implementation of the classifier, for example as a majority vote of all the 30×625 trained classification trees trained at step 224, by selecting one specific train/test split iteration that has optimum performance and generalizes well, or in some other manner. As indicated at 272, the classifier as configured and defined at step 270 is then validated on an independent sample set.

Referring to FIG. 4, in each sampling of the reserved set 250, a classification tree was grown on Training Set 2 (256) and the test set (254) was evaluated with it. The data was split at step 200 into ⅓ for Training Set 1 (202), ⅔ for Reserve set (250), and then equal proportions of the subsequent splits (252) of the Reserve set (250) to Training Set 2 (256) and the Test set (254).

The procedure for growing the classification trees (224) for this project was as follows:
1. For non-categorical features, the values of each feature were sampled to get a list of feature values to consider when splitting each node in the tree. The values were taken to be the $10^{th}$, $20^{th}$, . . . , $90^{th}$ percentile of observed feature values in the training set.
2. The training set 2 (256) was recursively split: The entire training set 2 (256) was assigned to the initial node. The procedure for each recursive node split was as follows:
   a. Sample the features in the training set 2 (256): Take a random subset of floor(sqrk<number of features>)) features out of the list of the total set of features in the training data.
   b. If the depth of the tree exceeds 100: stop this recursion.
   c. For each possible value of the feature, for each feature in this feature subset, split the samples at this node by feature value into two candidate children nodes. If both groups have at least one sample present, consider this split valid. Calculate and store the weighted change in cross entropy from the parent node to the candidate children nodes. The class entropy for a set of samples with some classes is defined in terms of the class proportions in the set, $p_i$, as: $I_C = -\Sigma_{i \in classes} p_i * \log(p_i)$, with $0* \log (0)$ taken to be the limit from the right which is 0. The average entropy gain from the parent to the child nodes with the left node containing fraction $f_{left}$ of the samples and the right node containing fraction $f_{right}$ is: $L_C = I_C$ (parent) $-(f_{left} * I_C(\text{left}) + f_{right} * I_C(\text{right}))$.
   d. If no possible splits are found, stop this recursion.
   e. Pick the feature and associated feature value that gives the largest change in cross entropy as defined in (c).
   f. Assign each group the label (event or no event) corresponding to the majority of its members.
   g. Split one child node.
   h. Split the other child node.

The trained classification trees 224 now play the role of the logistic regression master classifiers in the original "Diagnostic Cortex" procedure for the purpose of obtaining the final (binary) class label for a new sample, e.g., Group1 (higher risk) or Group 2 (lower risk). Out of bag estimates are obtained by looking at the prediction of each classification tree for which a sample was in the test set. For the purpose of generating Receiver Operator Characteristic (ROC) curves, a binary classifier needs a continuous score that can be thresholded to produce classifications for different choices of the threshold. For the classifiers that did not include additional decision trees (child classifiers), the output probability or logit from the master classifier logistic regression step in each bag was used as this score. For a given threshold, master classifiers giving a score of less than the threshold were treated as voting for higher risk and the modified majority vote was then done as normal to get the final classification. For the models with additional classification trees (initial binary classifiers), this score was taken to be the fraction of trees voting for higher risk. For this project, a majority vote was used as the selection of the final test in step 270 that could be applied to patients from an independent test set or other unseen patients. (This was implemented as an out-of-bag estimate to obtain classifications for patients in the development set.)

As indicated previously in the discussion of FIG. 1, a set of binary classifiers were trained to directly predict risk of 4 unfavorable endpoints: admission to the ICU ('admitted_to_icu' in table 4), development of any complication during hospitalization ('Complications during hospitalization? (choice=Any)' in table 4), development of acute respiratory distress syndrome during hospitalization ('Complications during hospitalization? (choice=ARDS)' in table 4), patient was intubated ('intubated' in table 4). All 4 cases used identical Diagnostic Cortex (i.e., procedure of steps 216, optional step 218, and step 220 and 222 of FIG. 4) and Decision tree parameters which are summarized below.

Diagnostic Cortex Parameters (steps 216, optional step 218, 220, 222)

625 Train/Test realizations (bags) were used, i.e., iterations through loop 262.

The atomic or mini-classifiers created at step 216 were k-NN's with k=11 and were allowed to go up to 3 features deep, considering classifiers at all levels. No atomic classifier filtering (step 218) was used.

Standard logistic regression with dropout was used with 10 atomic classifiers left in at each of the 100,000 dropout iterations in step 222.

Decision Tree Parameters (254):

30 sub-bags (iterations through inner loop 260) were used for each realization of the separation of the development set into Test and Training set 2, at step 252.

The outputs of the master classifiers 222 (logits) were binarized using a cutoff of 0.5 and treated as categorical in the trees.

Categorical interaction terms were calculated between the binarized logit feature and all other included categorical features.

The minimum leaf size was 1.

The maximum depth of the trees was set to 100

The optimization metric for splitting criteria was 'cross-entropy' as defined above A weighted (by resulting group size) average was used in the entropy gain calculation at each split.

Feature binning was used for non-categorical features. The 'percentile' option was used with 10 bins.

Figure 22:
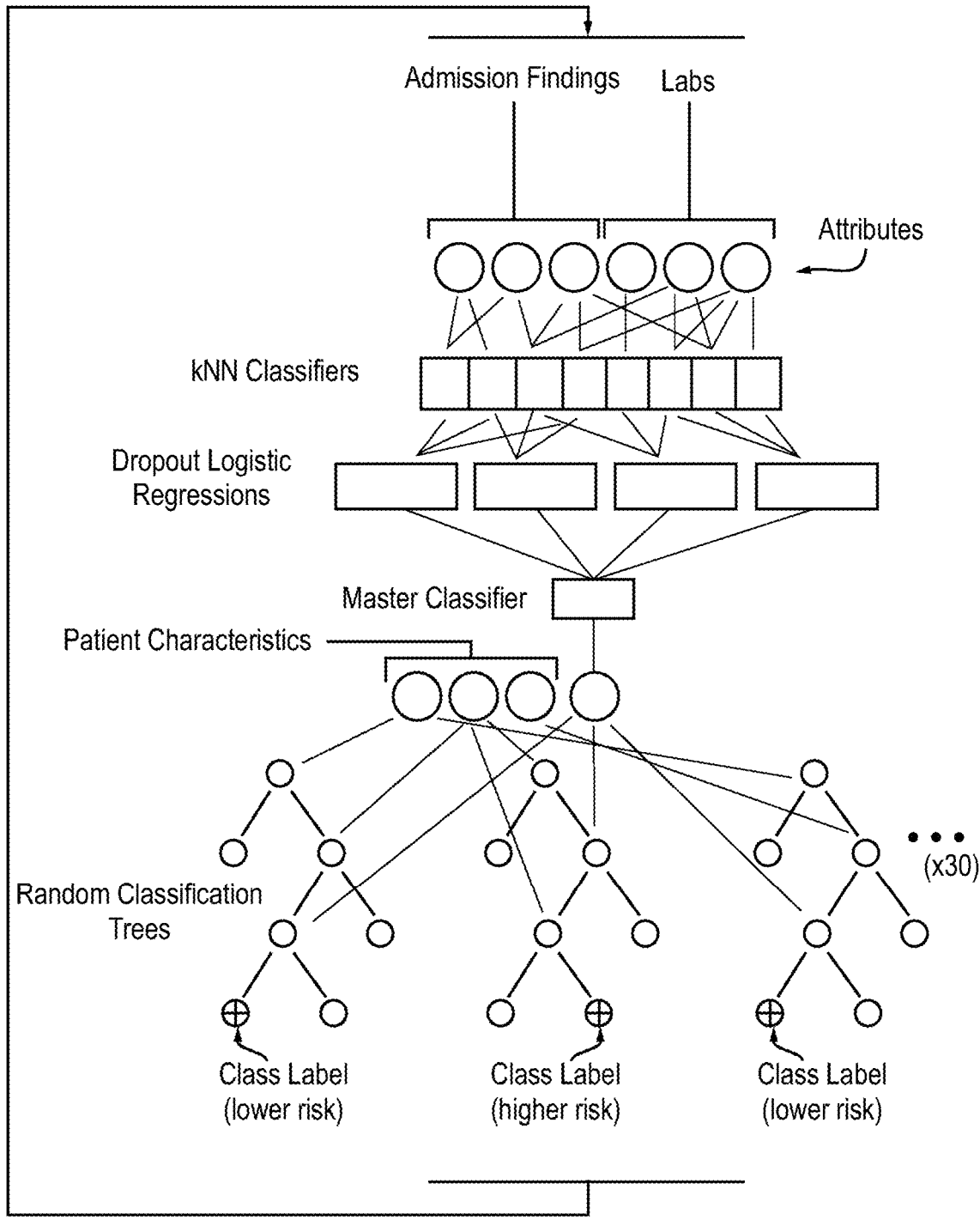
FIG. 22 is an illustration showing the procedure, implemented in a computer, for generating a classification for a patient using an initial binary classifier, e.g., of FIG. 6 or 7.

FIG. 22 shows the procedure for generating a classification for a patient in accordance with the initial binary classifiers 16 trained in accordance with FIG. 4 and shown in the tests described below. From top to bottom, data collected at admission (e.g. emergency department findings (e.g., vital signs)) and laboratory data (i.e., classification features or attributes, the feature space 204 of FIG. 4)) are fed into the set of k-NN classifiers which each use up to three attributes. Each k-NN individually outputs 0 or 1 for high or low risk. The output of the k-NNs are input to the set of dropout logistic regressions which each use 10 k-NNs as regressors. The predictions of these regressions are aggregated to a single label, 0 or 1 for high or low risk. This label is combined with basic patient characteristic data in a set of decision trees (224 in FIG. 4) where each split in the tree corresponds to an individual decision rule. Each tree classifies a sample as either high or low risk. This is all done for each of the 625 bags that were defined in classifier development (loop 262 in FIG. 4) and the 30 bags that were defined in classifier development (loop 260 in FIG. 4). A simple majority vote over the set of resulting trees across all bags (625×30) is used to assign the final classification under this binary classifier, namely lower risk or higher risk.

B. Child Classifiers

The child classifiers without decision trees, which are used to further stratify the class labels produced by the classifiers trained in accordance with FIG. 4, are shown in FIG. 6 at 306 and 308 and shown in FIG. 7 at 402, 404 and 406. These child classifiers are developed and trained in accordance with the procedure of FIG. 5. Basically, these child classifiers are configured as a logistical combination of atomic or mini-classifiers with drop-out regularization and the process of generating and training the classifier is as explained in FIG. 5, and in the prior patent and articles of Röder et al. cited above.

In particular, referring to FIG. 5, we have the "child classifier development set" 100A, consisting of clinical data, findings at admission and laboratory data for a multitude of hospitalized COVID-19 patients classified as either higher risk or lower risk by the initial binary classifier as explained above, with the higher risk group of patients used to train a child "highest" or "high risk" classifier, and the lower risk group of patients used to train a child "lowest" or "low risk" classifier. At step 102A, a label associated with some attribute of each member of the child classifier development set is assigned (for example, patient intubated or not intubated, "Group1", "Group2" etc. the precise moniker of the label is not important). In this example, and was also the case with the assignment of class labels in FIG. 4 at step 102, the class labels were assigned by a human operator to each member of the child classifier development set after investigation of the outcome data associated with the sample. In this example, the child classifier development set is split into two groups, "Group1" (104A) being the label assigned to patients who experienced the particular unfavorable outcome and "Group2" (106A) being the label assigned to patients who did not experience the unfavorable outcome, based on the outcome data associated with the samples. This results in a class-labelled child development set shown at 108A.

Then, at step 110, the class-labeled child classifier development sample set 108A is split into a training set 112 and a test set 114. The training set is used in the following steps 116, 118 and 120, which are described in detail in conjunction with the similar steps 216, 218, and 220 of FIG. 4 and therefore a description is omitted. The master classifier is generated at step 120 from logistic regression and dropout regularization. At step 122 the classification performance of this this master classifier is evaluated on the test set 114. We loop over many train/test split realizations, such as 625 in all, each iteration generating a master classifier. At step 126 we analyze the data from all the realizations of the separation of the development set of samples into training and test sets.

The method continues with step 130 of defining a final classifier from one or a combination of more than one of the plurality of master classifiers. For example, the final classifier is defined as a majority vote or ensemble average of all the master classifiers resulting from each separation of the sample set into training and test sets, or alternatively by selecting one Master Classifier that has typical performance, or some other procedure. In the examples in this application, the continuous logit output of the master classifiers was averaged (using an out-of-bag procedure for patients in the development set). This continuous output was analyzed using receiver operating characteristics methods to investigate the family of binary classifiers obtained applying a cutoff to this output. The final classifier was obtained by applying a cutoff of 0.5 to the logit output of each master classifier and carrying out a majority vote over the resulting classifications (out-of-bag majority vote for patients in the development set). This is similar, but not identical to applying a cutoff of 0.5 to the ensemble averaged continuous master classifier logit output. At step 132, the classifier (or test) developed from the procedure of FIG. 5 and defined at step 130 is validated on an independent validation set. A report describing our validation of the classifiers of FIGS. 4 and 5 on an independent validation set is set forth as Appendix A to our prior provisional application, Ser. No. 63/125,527.

Figure 23:
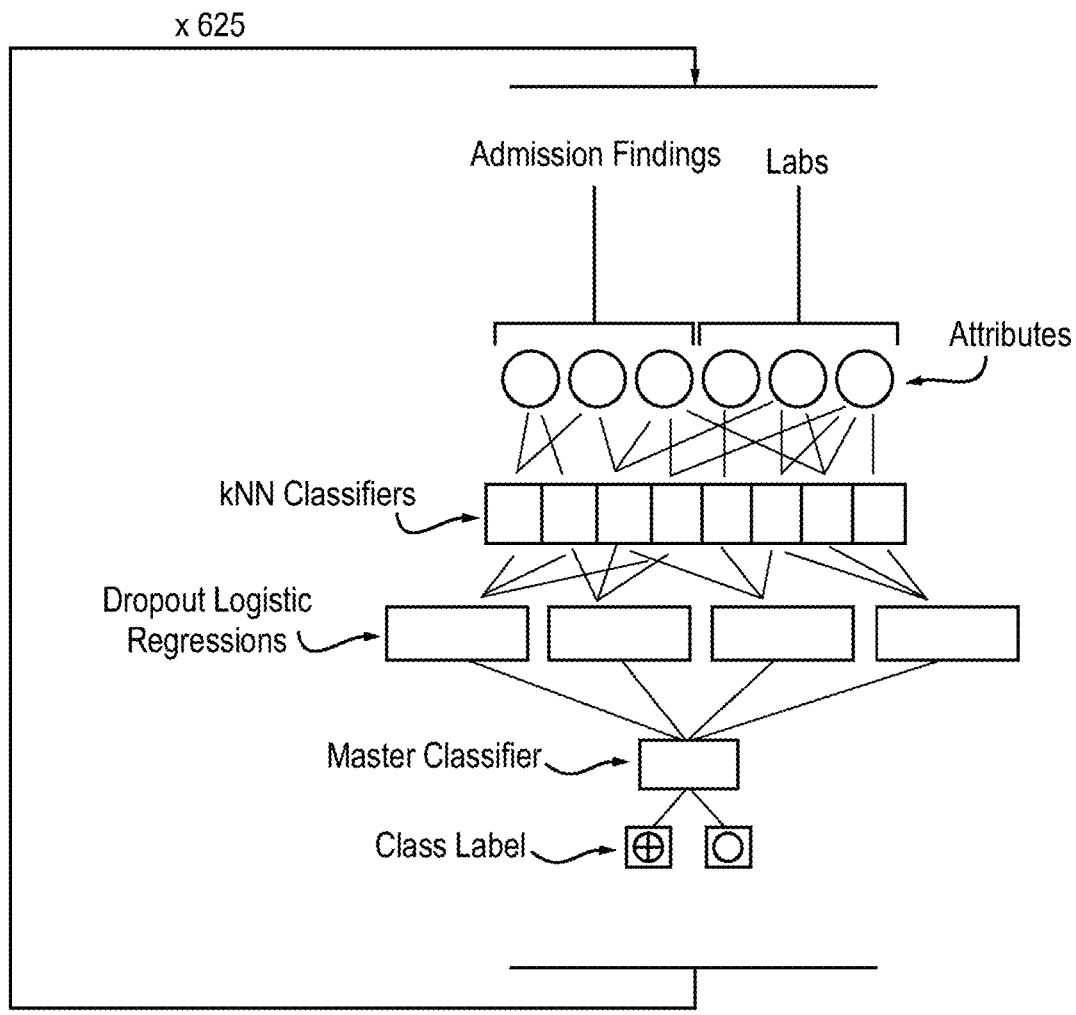
FIG. 23 is an illustration showing the procedure, implemented in a computer, for generating a classification for a patient using a child classifier, e.g., one of the child classifiers of FIGS. 6, or child and intermediate classifiers of FIG. 7. To generate a class label for the patient, e.g., lowest or highest risk, the procedures of FIGS. 22 and 23 are combined using a logical operation linking the binary and child classifiers as shown in FIGS. 6 and 7 or in the hierarchical arrangements for the ARDS, intubation, any complication and ICU admission tests of FIG. 14, 16, 19 or 21.

FIG. 23 shows the procedure for generating a classification for a patient in accordance with the child (and intermediate) classifiers of the tests described below. From top to bottom, findings at hospital admission (e.g., vital signs) and laboratory data (i.e., classification features or attributes, the feature space of FIG. 5)) are fed into the set of k-NN classifiers which each use up to three attributes. Each k-NN individually outputs 0 or 1 for high or low risk. The output of the kNNs are input to the set of dropout logistic regressions which each use 10 kNNs as regressors. The predictions of these regressions are aggregated to form a master classifier yielding a single label, 0 or 1 for high or low risk, for example by averaging the outputs of all the dropout logistic regressions. The classification of a patient is then obtained by performing an ensemble average, for example by majority vote, over the outputs of all master classifiers.

Results

Figure 8:
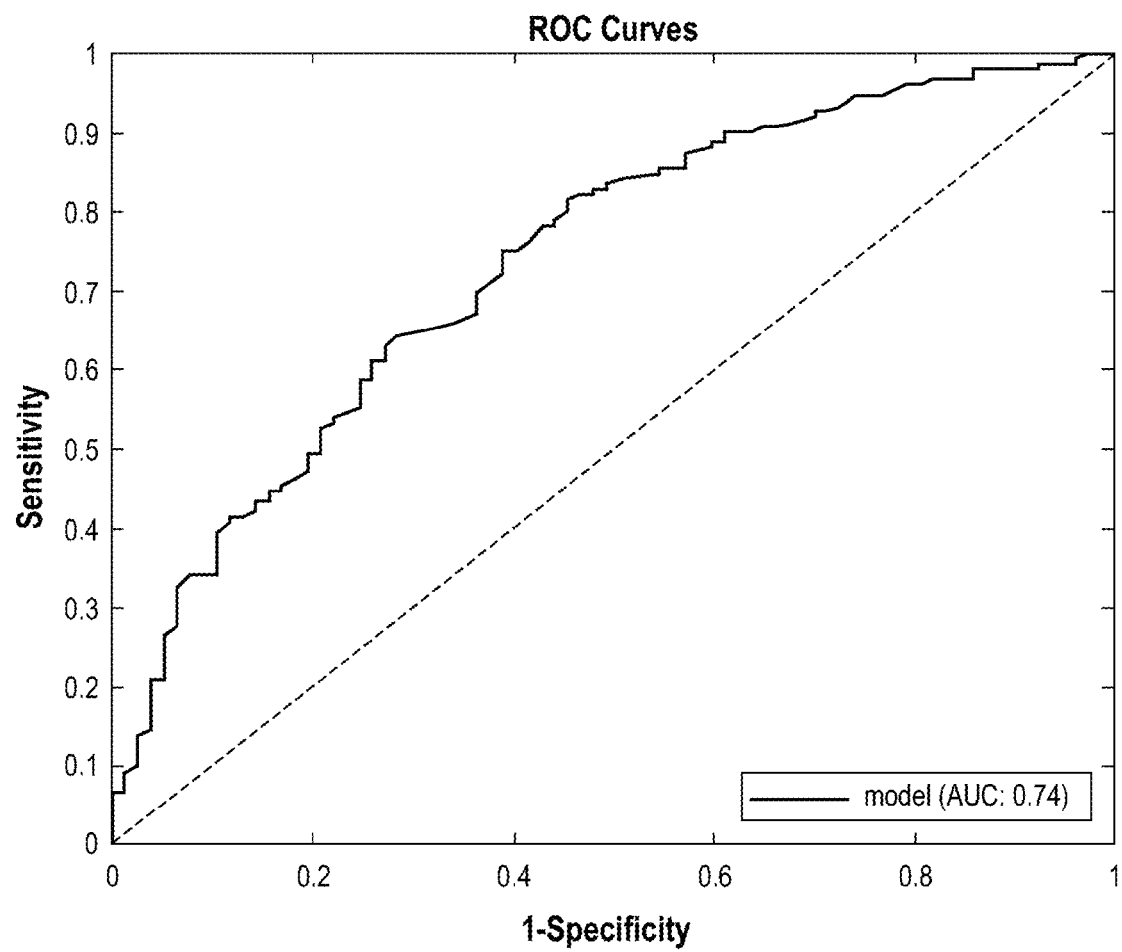
FIG. 8 is a receiver operating characteristic curve for an initial binary classifier predicting risk of ICU admission.
Figure 9:
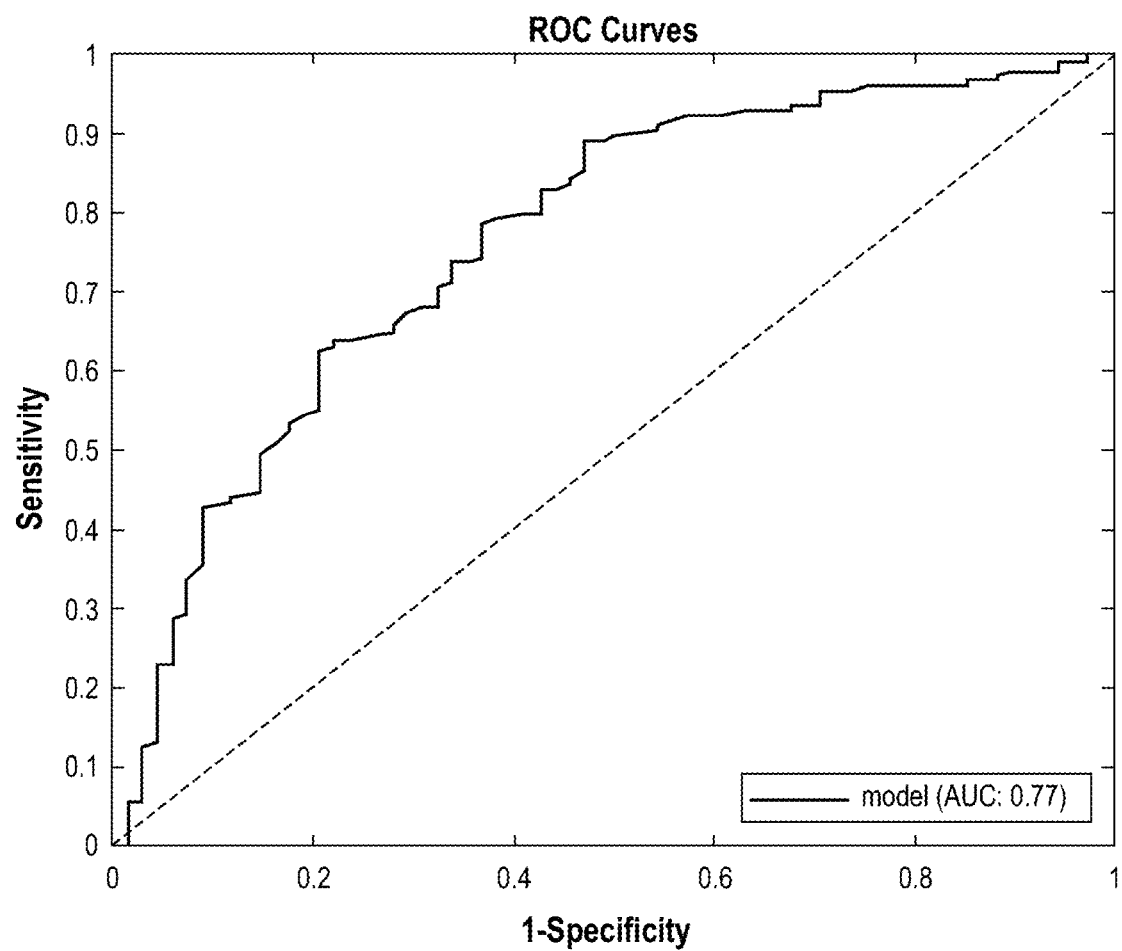
FIG. 9 is a receiver operating characteristic curve for an initial binary classifier predicting risk of any complication.
Figure 10:
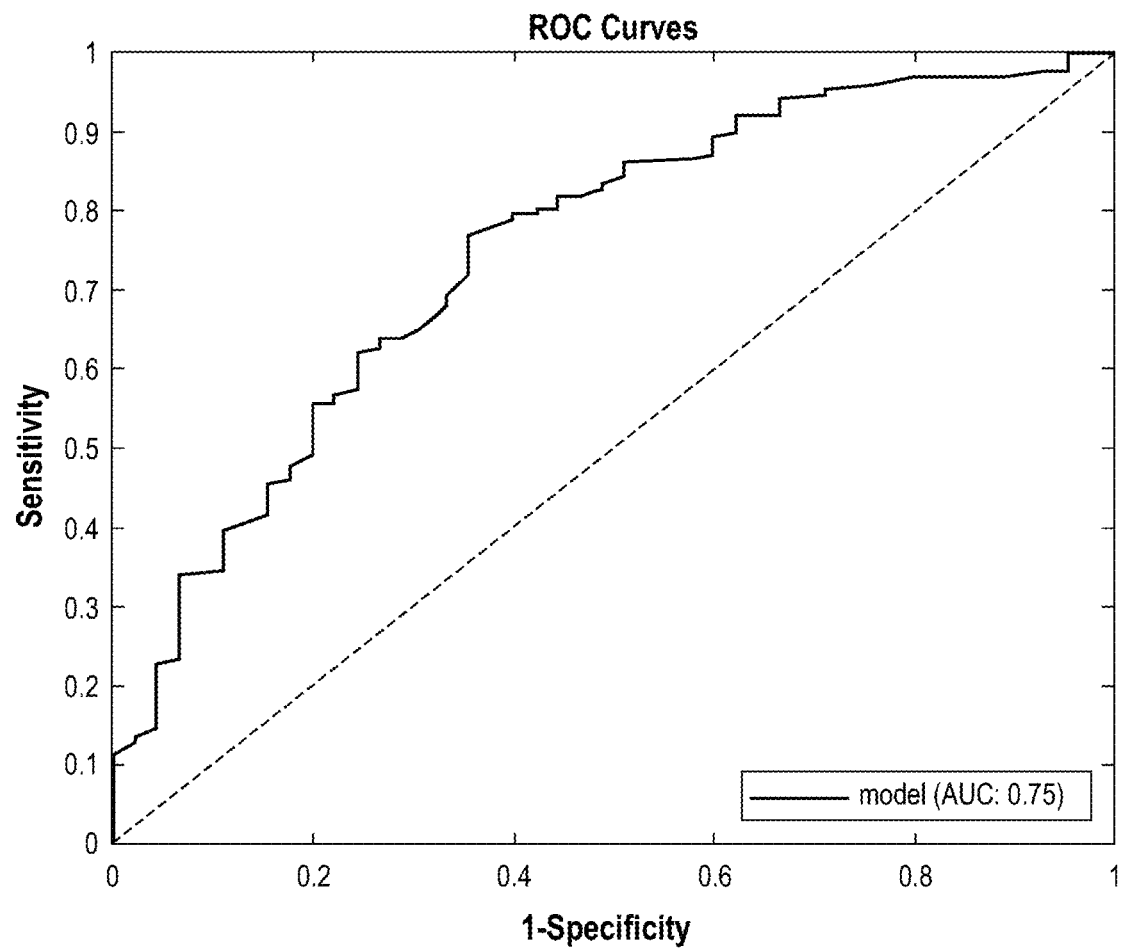
FIG. 10 is a receiver operating characteristic curve for an initial binary classifier predicting risk of ARDS.
Figure 11:
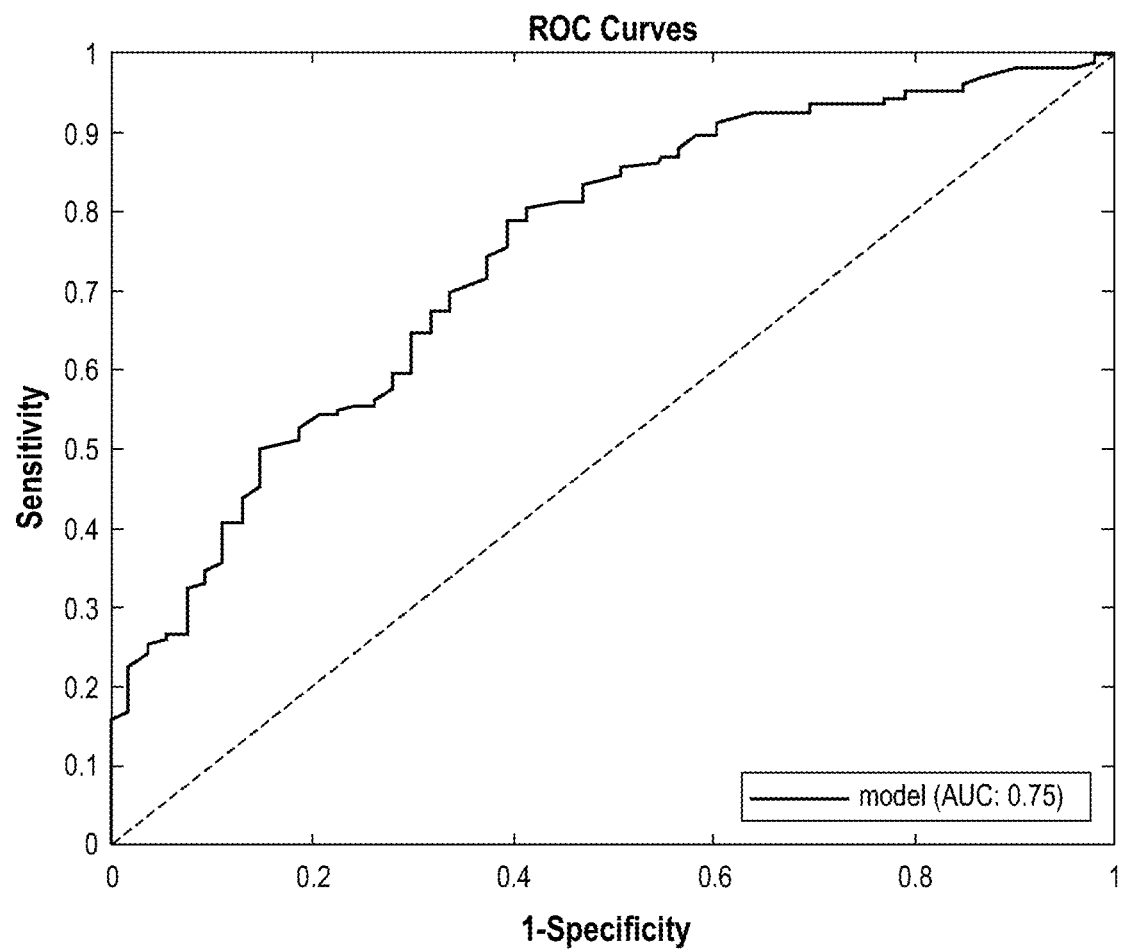
FIG. 11 is a receiver operating characteristic curve for an initial binary classifier predicting risk of intubation.

For each endpoint (unfavorable outcome) considered, the proportion of classification trees classifying a sample as the positive class (occurrence of the endpoint) was used to define a score following the standard out of bag estimate procedure. FIGS. 8-11 give receiver operating characteristic (ROC) curves based on this score for each of the four endpoints. In particular, FIG. 8 is a receiver operating characteristic curve for a binary classifier (trained in accordance with FIG. 4) predicting risk of ICU admission on the development set. FIG. 9 is a receiver operating characteristic curve for a binary classifier predicting risk of any complication on the development set. FIG. 10 is a receiver operating characteristic curve for a binary classifier predicting risk of ARDS on the development set. FIG. 11 is a receiver operating characteristic curve for a binary classifier predicting risk of intubation on the development set.

While in theory a test for predicting risk of one of the endpoints illustrated in the ROC curves of FIGS. 8-11 could simply consist of the output of the initial binary classifier trained in accordance with FIG. 4, in practice we have found it advisable to further stratify the classification results from the initial binary classifier with what we have called "child" or intermediate classifiers, which are trained in accordance with the procedure of FIG. 5.

Specifically, additional (no-tree) "Diagnostic Cortex" classifiers (trained per FIG. 5) were trained to split the resulting groups of the binary classifiers of the previous section in a hierarchical fashion. Note that each child classifier was trained using a subset of the initial development set. For example, the child classifier splitting patients defined to be at lower risk of any complication by the binary classifier into lowest risk and low risk groups was trained using only data from patients defined as lower risk by the any complication binary classifier. All models took a default cutoff value of 0.5 to assign patients either a 'higher risk' or 'lower risk' binary classification. All child classifiers did not use trees and were trained only using the findings at admission and bloodwork numbers, and were trained as stated in accordance with FIG. 5. The Diagnostic Cortex operating parameters were the same as for the binary classifiers previously described.

One of two different hierarchical configurations of the binary classifiers and the child classifiers were used to define the tests of this disclosure, and are illustrated in FIGS. 6 and 7. In particular, FIG. 6 shows a hierarchical configuration without an intermediate classifier. Specifically, this hierarchical combination consists of an initial binary classifier 300 which is trained in accordance with FIG. 4 to produce lower risk and higher risk classifications, and "child" classifiers 306 and 308 which further stratify the lower risk and higher risk groups. If the initial binary classifier 300 produces a lower risk class label for the patient, the patient's electronic health record data (laboratory and emergency department findings) are classified by the child classifier 306, which is trained in accordance with FIG. 5 to produce either lower risk or higher risk labels. If the child classifier 306 produces a lower risk class label the patient is classified as lowest risk (310), whereas if the child classifier 306 produces the higher risk class label the patient is classified as low risk (312). Conversely, if the binary classifier 300 produces the higher risk class label 304, the patient's electronic health record data (laboratory and findings obtained at admission) are classified by the child classifier 308 which produces a lower risk or a higher risk class label. If the classifier 308 produces the lower risk class label the patient is classified as high risk (314) and if the classifier 308 produces the higher risk class label the patient is classified as highest risk (316).

FIG. 7 shows an alternative hierarchical configuration of binary and child classifiers, which includes an intermediate or "grandchild" classifier. In this configuration, there is an initial binary classifier 400 which generates lower and higher risk classifications, which is trained in accordance with FIG. 4. There are two child and one intermediate classifiers. If the binary classifier 400 produces a lower risk classification, a child classifier 402 further stratifies the patient into a lower risk or higher risk group. If the patient is classified as lower risk, the lowest risk classification label (410) is reported. If the child classifier 402 produces the higher risk class label, the patient is classified with an intermediate classifier 404, which generates low and high risk classification labels 412 and 414. If the binary classifier 400 produces a higher risk classification 304, the patient is classified with the second child classifier 406 which produces higher and lower risk classifications. If the classification produced by the classifier 406 is higher risk, a highest risk classification label 416 is reported. If the classifier 406 produces a lower risk classification label, the patient is further classified by the intermediate classifier 404 which produces the classification labels low risk and high risk as indicated at 412 and 414. Binary classifier 400 is trained in accordance with FIG. 4 and includes the decision trees, whereas the intermediate and child classifiers 402, 404 and 406 are trained in accordance with FIG. 5 and do not include decision trees.

Predicting Risk of ICU Admission

Figure 14:
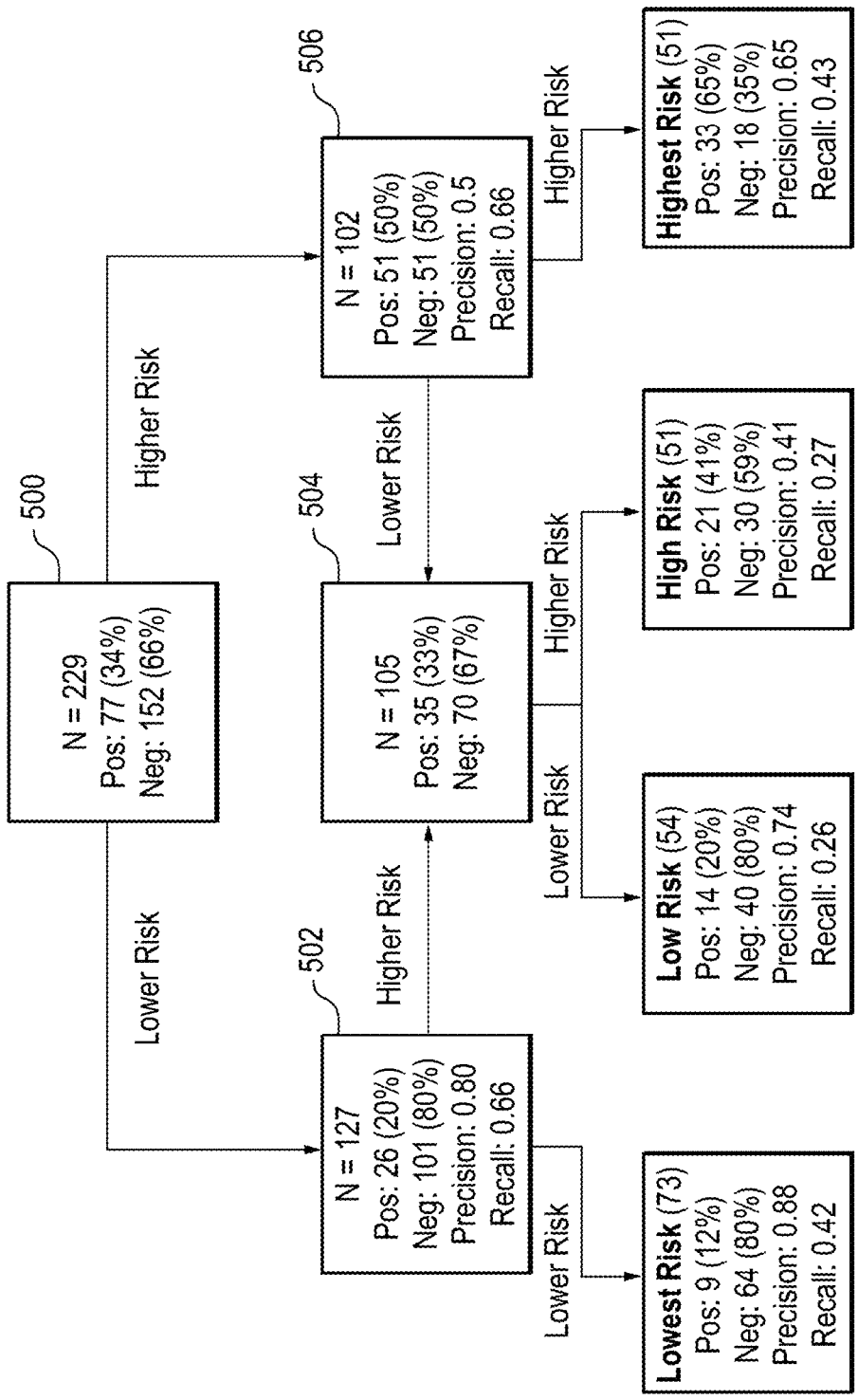
FIG. 14 is a schematic diagram showing the hierarchical combination of binary and child classifiers for predicting risk of ICU admission; note that this schema follows the configuration of FIG. 7.

FIG. 14 shows the configuration of the ICU classifier, which is designed in accordance with the schema of FIG. 7. It includes the initial binary classifier 500 generating higher and lower risk classifications, developed in accordance with the procedure of FIG. 4, and child and intermediate classifiers 502, 504 and 506, each developed in accordance with the procedure of FIG. 5.

Figure 12:
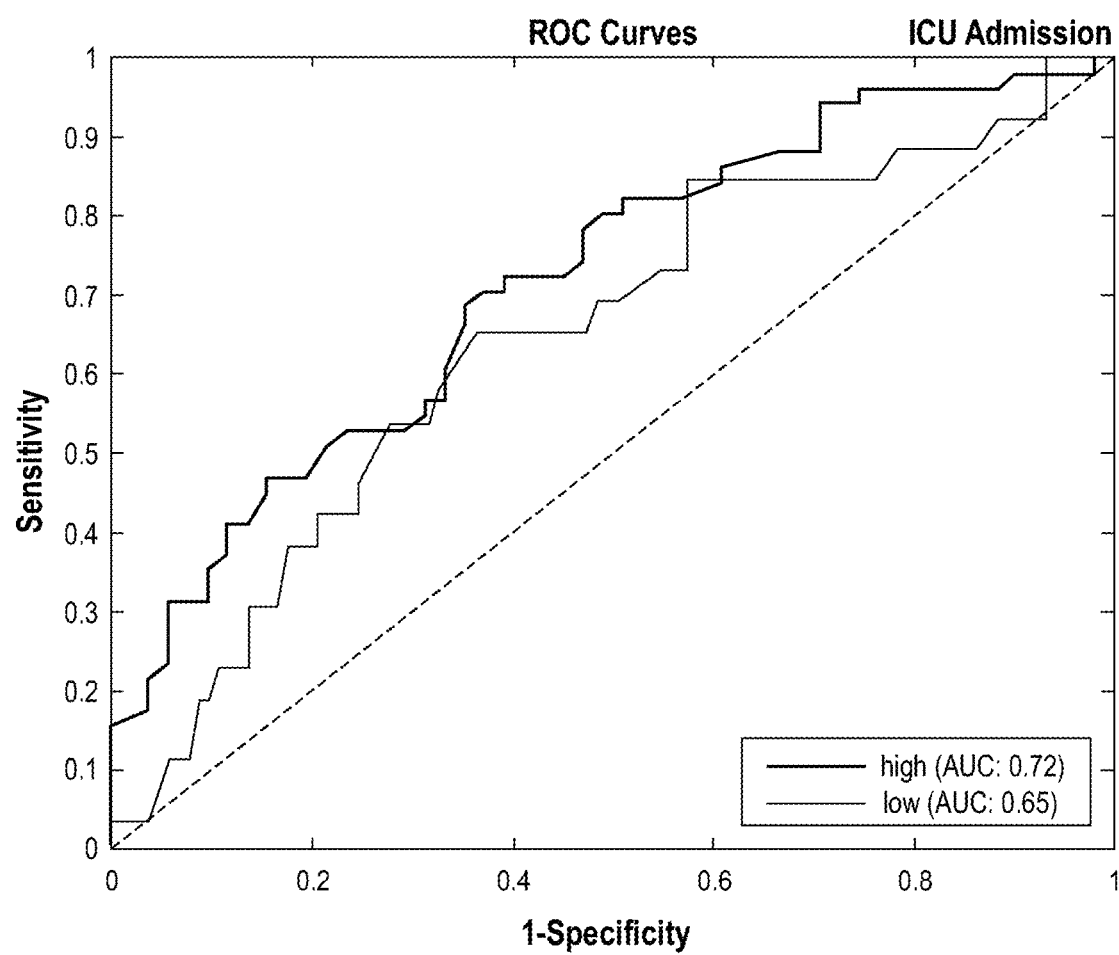
FIG. 12 is a receiver operating characteristic curve for low risk and high risk child classifiers predicting risk of ICU admission.
Figure 13:
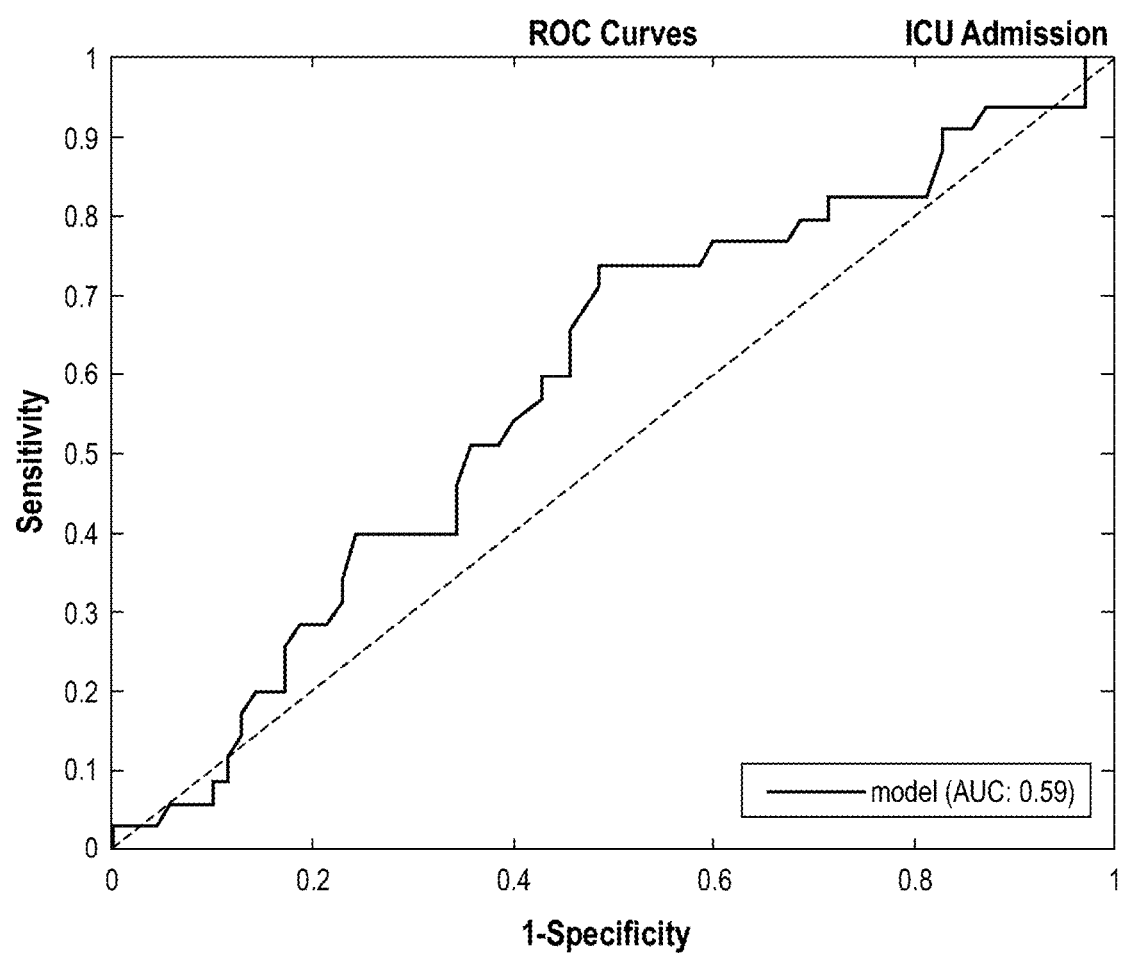
FIG. 13 is a receiver operating characteristic curve for an intermediate risk classifier predicting risk of ICU admission.

FIG. 12 is a receiver operating characteristic curve for the low risk and high risk child classifiers 502 and 506 predicting risk of ICU admission. FIG. 13 is a receiver operating characteristic curve for the intermediate classifier 504 predicting risk of ICU admission. The ROC curve for the binary classifier 500 is shown in FIG. 8.

Referring to FIG. 14, seventy-seven patients out of the 229 in the development set were admitted to the ICU. The initial binary classifier 500 separated these patients into lower and higher risk groups. The lower risk group had 127 patients of whom 26 were admitted to the ICU. The higher risk group had 102 patients of whom 51 were admitted to the ICU. Both groups were split again into higher and lower risk groups using a high and low risk child classifier (502 and 506 in FIG. 14). Patients from the lower risk group that were classified as lower risk by the low risk child classifier (502) were assigned to the lowest risk final group consisting of 73 patients of whom 9 were admitted to the ICU. Likewise, patients from the higher risk group that were classified as higher risk by the high risk child classifier (506) were assigned to the highest risk final group consisting of 51 patients of whom 33 were admitted to the ICU.

The remaining two groups were combined into a group of 105 patients of whom 35 were admitted to the ICU. This group of patents was split into a higher and lower risk group by the intermediate risk classifier 504. Patients in the higher risk group were assigned to the final high risk group, consisting of 51 patients of whom 21 were admitted to the ICU. Patients in the lower risk group were assigned to the final low risk group, consisting of 54 patients of whom 14 were admitted to the ICU.

Tables 7 and 8 shows selected clinical attributes by final group classification.

TABLE 7

Summary of selected categorical attributes for the classes of the hierarchical classifier for assessment of risk of ICU Admission

| | | lowest | low | high | highest |
|---|---|---|---|---|---|
| | | | n (proportion of group) | | |
| Attribute | Category | N = 73 | N = 54 | N = 51 | N = 51 |
| | Race | | | | |
| | Race or Ethnicity (choice = White) | 21 (0.288) | 12 (0.222) | 6 (0.118) | 2 (0.039) |

TABLE 7-continued

Summary of selected categorical attributes for the classes of the hierarchical classifier for assessment of risk of ICU Admission

| Attribute | Category | lowest N = 73 | low N = 54 | high N = 51 | highest N = 51 |
|---|---|---|---|---|---|
| | | n (proportion of group) | | | |
| | Race or Ethnicity (choice = Black or African American) | 14 (0.192) | 13 (0.241) | 11 (0.216) | 14 (0.275) |
| | Race or Ethnicity (choice = Hispanic or Latino) | 31 (0.425) | 19 (0.352) | 23 (0.451) | 21 (0.412) |
| | Race or Ethnicity (choice = Other) | 6 (0.082) | 7 (0.130) | 8 (0.157) | 10 (0.196) |
| | Race or Ethnicity (choice = Unknown) | 1 (0.014) | 3 (0.056) | 3 (0.059) | 4 (0.078) |
| sex or gender | | | | | |
| | Male | 27 (0.370) | 34 (0.630) | 25 (0.490) | 38 (0.745) |
| | Female | 46 (0.630) | 20 (0.370) | 26 (0.510) | 13 (0.255) |
| Comorbidities (choice = None) | | | | | |
| | 0 | 58 (0.795) | 48 (0.889) | 43 (0.843) | 42 (0.824) |
| | 1 | 15 (0.205) | 6 (0.111) | 8 (0.157) | 9 (0.176) |
| Comorbidities (choice = Hypertension) | | | | | |
| | 1 | 29 (0.397) | 29 (0.537) | 17 (0.333) | 25 (0.490) |
| | 0 | 44 (0.603) | 25 (0.463) | 34 (0.667) | 26 (0.510) |
| Comorbidities (choice = Hyperlipidemia) | | | | | |
| | 0 | 56 (0.767) | 46 (0.852) | 39 (0.765) | 41 (0.804) |
| | 1 | 17 (0.233) | 8 (0.148) | 12 (0.235) | 10 (0.196) |
| Comorbidities (choice = Type 2 Diabetes) | | | | | |
| | 0 | 53 (0.726) | 27 (0.500) | 35 (0.686) | 32 (0.627) |
| | 1 | 20 (0.274) | 27 (0.500) | 16 (0.314) | 19 (0.373) |
| Comorbidities (choice = Cardiovascular Disease) | | | | | |
| | 0 | 61 (0.836) | 49 (0.907) | 48 (0.941) | 45 (0.882) |
| | 1 | 12 (0.164) | 5 (0.093) | 3 (0.059) | 6 (0.118) |
| Comorbidities (choice = Respiratory Disease) | | | | | |
| | 0 | 58 (0.795) | 39 (0.722) | 43 (0.843) | 40 (0.784) |
| | 1 | 15 (0.205) | 15 (0.278) | 8 (0.157) | 11 (0.216) |
| Comorbidities (choice = Gastrointestinal Disease) | | | | | |
| | 0 | 62 (0.849) | 48 (0.889) | 42 (0.824) | 48 (0.941) |
| | 1 | 11 (0.151) | 6 (0.111) | 9 (0.176) | 3 (0.059) |
| Comorbidities (choice = Renal Disease) | | | | | |
| | 0 | 66 (0.904) | 46 (0.852) | 47 (0.922) | 46 (0.902) |
| | 1 | 7 (0.096) | 8 (0.148) | 4 (0.078) | 5 (0.098) |
| Comorbidities (choice = Endocrine Disease (Excluding Diabetes)) | | | | | |
| | 0 | 65 (0.890) | 53 (0.981) | 46 (0.902) | 50 (0.980) |
| | 1 | 8 (0.110) | 1 (0.019) | 5 (0.098) | 1 (0.020) |
| Comorbidities (choice = Neurologic Disease) | | | | | |
| | 0 | 56 (0.767) | 47 (0.870) | 44 (0.863) | 47 (0.922) |
| | 1 | 17 (0.233) | 7 (0.130) | 7 (0.137) | 4 (0.078) |
| Comorbidities (choice = Psychiatric Disease) | | | | | |
| | 0 | 63 (0.863) | 47 (0.870) | 47 (0.922) | 47 (0.922) |
| | 1 | 10 (0.137) | 7 (0.130) | 4 (0.078) | 4 (0.078) |
| Comorbidities (choice = Cancer) | | | | | |
| | 0 | 65 (0.890) | 52 (0.963) | 46 (0.902) | 49 (0.961) |
| | 1 | 8 (0.110) | 2 (0.037) | 5 (0.098) | 2 (0.039) |

TABLE 7-continued

Summary of selected categorical attributes for the classes of the
hierarchical classifier for assessment of risk of ICU Admission

| Attribute | Category | lowest<br>N = 73 | low<br>n (proportion of group)<br>N = 54 | high<br>N = 51 | highest<br>N = 51 |
|---|---|---|---|---|---|
| Comorbidities<br>(choice = Infectious Disease) | | | | | |
| | 0 | 71 (0.973) | 50 (0.926) | 50 (0.980) | 50 (0.980) |
| | 1 | 2 (0.027) | 4 (0.074) | 1 (0.020) | 1 (0.020) |
| Comorbidities<br>(choice = Autoimmune Disease) | | | | | |
| | 0 | 70 (0.959) | 54 (1.000) | 47 (0.922) | 51 (1.000) |
| | 1 | 3 (0.041) | 0 (0.000) | 4 (0.078) | 0 (0.000) |
| Comorbidities<br>(choice = Arthritis) | | | | | |
| | 0 | 67 (0.918) | 51 (0.944) | 45 (0.882) | 50 (0.980) |
| | 1 | 6 (0.082) | 3 (0.056) | 6 (0.118) | 1 (0.020) |
| Comorbidities<br>(choice = Chronic Pain Syndrome) | | | | | |
| | 0 | 67 (0.918) | 51 (0.944) | 50 (0.980) | 50 (0.980) |
| | 1 | 6 (0.082) | 3 (0.056) | 1 (0.020) | 1 (0.020) |
| Comorbidities<br>(choice = Morbid Obesity) | | | | | |
| | 0 | 71 (0.973) | 40 (0.741) | 42 (0.824) | 40 (0.784) |
| | 1 | 2 (0.027) | 14 (0.259) | 9 (0.176) | 11 (0.216) |
| Symptoms at presentation<br>(choice = Shortness of breath) | | | | | |
| | 0 | 37 (0.507) | 19 (0.352) | 17 (0.333) | 12 (0.235) |
| | 1 | 36 (0.493) | 35 (0.648) | 34 (0.667) | 39 (0.765) |
| Symptoms at presentation<br>(choice = Fever) | | | | | |
| | 0 | 19 (0.260) | 19 (0.352) | 21 (0.412) | 20 (0.392) |
| | 1 | 54 (0.740) | 35 (0.648) | 30 (0.588) | 31 (0.608) |
| Symptoms at presentation<br>(choice = Cough) | | | | | |
| | 0 | 20 (0.274) | 15 (0.278) | 10 (0.196) | 12 (0.235) |
| | 1 | 53 (0.726) | 39 (0.722) | 41 (0.804) | 39 (0.765) |
| Symptoms at presentation<br>(choice = AMS/Confusion) | | | | | |
| | 0 | 69 (0.945) | 47 (0.870) | 51 (1.000) | 47 (0.922) |
| | 1 | 4 (0.055) | 7 (0.130) | 0 (0.000) | 4 (0.078) |
| Symptoms at presentation<br>(choice = Headache) | | | | | |
| | 0 | 62 (0.849) | 47 (0.870) | 46 (0.902) | 47 (0.922) |
| | 1 | 11 (0.151) | 7 (0.130) | 5 (0.098) | 4 (0.078) |
| Symptoms at presentation<br>(choice = Myalgia) | | | | | |
| | 1 | 19 (0.260) | 11 (0.204) | 10 (0.196) | 5 (0.098) |
| | 0 | 54 (0.740) | 43 (0.796) | 41 (0.804) | 46 (0.902) |
| Symptoms at presentation<br>(choice = Chills) | | | | | |
| | 0 | 52 (0.712) | 42 (0.778) | 39 (0.765) | 46 (0.902) |
| | 1 | 21 (0.288) | 12 (0.222) | 12 (0.235) | 5 (0.098) |
| Symptoms at presentation<br>(choice = Diarrhea) | | | | | |
| | 0 | 57 (0.781) | 47 (0.870) | 36 (0.706) | 39 (0.765) |
| | 1 | 16 (0.219) | 7 (0.130) | 15 (0.294) | 12 (0.235) |
| Symptoms at presentation<br>(choice = Sore Throat) | | | | | |
| | 0 | 70 (0.959) | 54 (1.000) | 49 (0.961) | 50 (0.980) |
| | 1 | 3 (0.041) | 0 (0.000) | 2 (0.039) | 1 (0.020) |

TABLE 7-continued

Summary of selected categorical attributes for the classes of the hierarchical classifier for assessment of risk of ICU Admission

| Attribute | Category | lowest<br>N = 73 | low<br>n (proportion of group)<br>N = 54 | high<br>N = 51 | highest<br>N = 51 |
|---|---|---|---|---|---|
| Symptoms at presentation (choice = Chest pain) | | | | | |
| | 0 | 67 (0.918) | 48 (0.889) | 44 (0.863) | 47 (0.922) |
| | 1 | 6 (0.082) | 6 (0.111) | 7 (0.137) | 4 (0.078) |
| Symptoms at presentation (choice = Fatigue) | | | | | |
| | 1 | 20 (0.274) | 11 (0.204) | 27 (0.529) | 11 (0.216) |
| | 0 | 53 (0.726) | 43 (0.796) | 24 (0.471) | 40 (0.784) |
| Symptoms at presentation (choice = Headache)_1 | | | | | |
| | 1 | 2 (0.027) | 3 (0.056) | 7 (0.137) | 0 (0.000) |
| | 0 | 71 (0.973) | 51 (0.944) | 44 (0.863) | 51 (1.000) |
| Symptoms at presentation (choice = Other) | | | | | |
| | 0 | 44 (0.603) | 33 (0.611) | 29 (0.569) | 32 (0.627) |
| | 1 | 29 (0.397) | 21 (0.389) | 22 (0.431) | 19 (0.373) |

TABLE 8

Summary of Selected Numeric Attributes for the Classes of the Hierarchical Classifier for risk assessment of ICU Admission (p values compare lowest risk group with others (low + high + highest) and highest risk group with others (lowest + low + high)

| Attribute | Class | Mean | Median | IQR | Mann-Whitney p |
|---|---|---|---|---|---|
| age | lowest | 54 | 54 | 32 | 0.245 |
| | low | 59 | 60 | 20 | |
| | high | 54 | 57 | 25 | |
| | highest | 57 | 55 | 20 | 0.791 |
| ed_temperature_c | lowest | 37 | 37 | 1.0 | 0.915 |
| | low | 37 | 37 | 0.80 | |
| | high | 37 | 37 | 1.1 | |
| | highest | 37 | 37 | 1.3 | 0.241 |
| ed_heart_rate | lowest | 100 | 110 | 28 | 0.339 |
| | low | 94 | 92 | 22 | |
| | high | 95 | 93 | 26 | |
| | highest | 110 | 110 | 35 | 0.003 |
| ed_systolic_bp | lowest | 140 | 140 | 35 | 0.02 |
| | low | 130 | 130 | 28 | |
| | high | 130 | 120 | 20 | |
| | highest | 140 | 140 | 20 | 0.212 |
| ed_diastolic_bp | lowest | 78 | 77 | 17 | 0.005 |
| | low | 73 | 73 | 15 | |
| | high | 70 | 66 | 20 | |
| | highest | 77 | 76 | 17 | 0.192 |
| ed_respiratory_rate | lowest | 21 | 20 | 4.5 | 0.082 |
| | low | 21 | 20 | 6.0 | |
| | high | 21 | 18 | 4.0 | |
| | highest | 25 | 24 | 9.0 | <0.001 |
| ed_oxygen_saturation | lowest | 93 | 93 | 4.0 | <0.001 |
| | low | 91 | 92 | 6.0 | |
| | high | 90 | 91 | 7.8 | |
| | highest | 82 | 85 | 13 | <0.001 |
| weight_kg | lowest | 77 | 77 | 12 | <0.001 |
| | low | 92 | 85 | 40 | |
| | high | 88 | 85 | 29 | |
| | highest | 95 | 94 | 32 | 0.008 |
| initial_qtc | lowest | 450 | 450 | 35 | 0.366 |
| | low | 440 | 440 | 30 | |
| | high | 430 | 420 | 37 | |
| | highest | 450 | 440 | 47 | 0.279 |

TABLE 8-continued

Summary of Selected Numeric Attributes for the Classes of the
Hierarchical Classifier for risk assessment of ICU Admission (p values
compare lowest risk group with others (low + high + highest)
and highest risk group with others (lowest + low + high)

| Attribute | Class | Mean | Median | IQR | Mann-Whitney p |
|---|---|---|---|---|---|
| sodium | lowest | 140 | 140 | 5.0 | 0.233 |
| | low | 140 | 140 | 3.0 | |
| | high | 140 | 140 | 3.8 | |
| | highest | 140 | 140 | 5.8 | 0.795 |
| potassium | lowest | 3.7 | 3.7 | 0.50 | 0.038 |
| | low | 3.8 | 3.7 | 0.40 | |
| | high | 3.8 | 3.8 | 0.55 | |
| | highest | 3.9 | 3.9 | 0.58 | 0.014 |
| carbon_dioxide_bicarb | lowest | 23 | 23 | 4.0 | 0.082 |
| | low | 23 | 23 | 3.0 | |
| | high | 23 | 23 | 3.8 | |
| | highest | 22 | 22 | 4.0 | 0.023 |
| bun | lowest | 14 | 12 | 7.0 | <0.001 |
| | low | 20 | 13 | 13 | |
| | high | 15 | 13 | 7.0 | |
| | highest | 29 | 20 | 17 | <0.001 |
| creatinine | lowest | 0.79 | 0.69 | 0.30 | <0.001 |
| | low | 1.3 | 1.0 | 0.49 | |
| | high | 0.98 | 0.95 | 0.41 | |
| | highest | 1.5 | 1.1 | 0.72 | <0.001 |
| anion_gap | lowest | 11 | 11 | 3.3 | 0.002 |
| | low | 12 | 12 | 3.0 | |
| | high | 12 | 12 | 3.0 | |
| | highest | 14 | 13 | 3.0 | <0.001 |
| wbc_screen | lowest | 6.2 | 5.8 | 2.8 | <0.001 |
| | low | 7.6 | 6.8 | 2.9 | |
| | high | 8.8 | 7.1 | 3.2 | |
| | highest | 9.8 | 8.9 | 4.6 | <0.001 |
| hemoglobin | lowest | 14 | 15 | 2.1 | 0.62 |
| | low | 14 | 15 | 2.4 | |
| | high | 14 | 14 | 2.4 | |
| | highest | 15 | 15 | 2.5 | 0.007 |
| hematocrit | lowest | 43 | 44 | 6.8 | 0.666 |
| | low | 43 | 43 | 7.4 | |
| | high | 42 | 42 | 6.0 | |
| | highest | 45 | 46 | 8.3 | 0.003 |
| platelet_count | lowest | 230 | 220 | 94 | 0.16 |
| | low | 210 | 210 | 66 | |
| | high | 210 | 210 | 120 | |
| | highest | 220 | 200 | 150 | 0.849 |
| initial_ldh | lowest | 270 | 250 | 82 | <0.001 |
| | low | 320 | 320 | 83 | |
| | high | 370 | 360 | 170 | |
| | highest | 520 | 440 | 220 | <0.001 |
| initial_d_dimer | lowest | 1100 | 560 | 620 | <0.001 |
| | low | 1100 | 840 | 1100 | |
| | high | 1300 | 900 | 760 | |
| | highest | 5900 | 1200 | 1600 | <0.001 |
| initial_c_reactive_protein | lowest | 56 | 48 | 54 | <0.001 |
| | low | 94 | 66 | 100 | |
| | high | 110 | 100 | 70 | |
| | highest | 180 | 150 | 150 | <0.001 |
| ferritin | lowest | 310 | 230 | 260 | <0.001 |
| | low | 610 | 440 | 430 | |
| | high | 740 | 480 | 860 | |
| | highest | 1900 | 590 | 850 | <0.001 |

Predicting Risk of Any Complication

Figure 16:
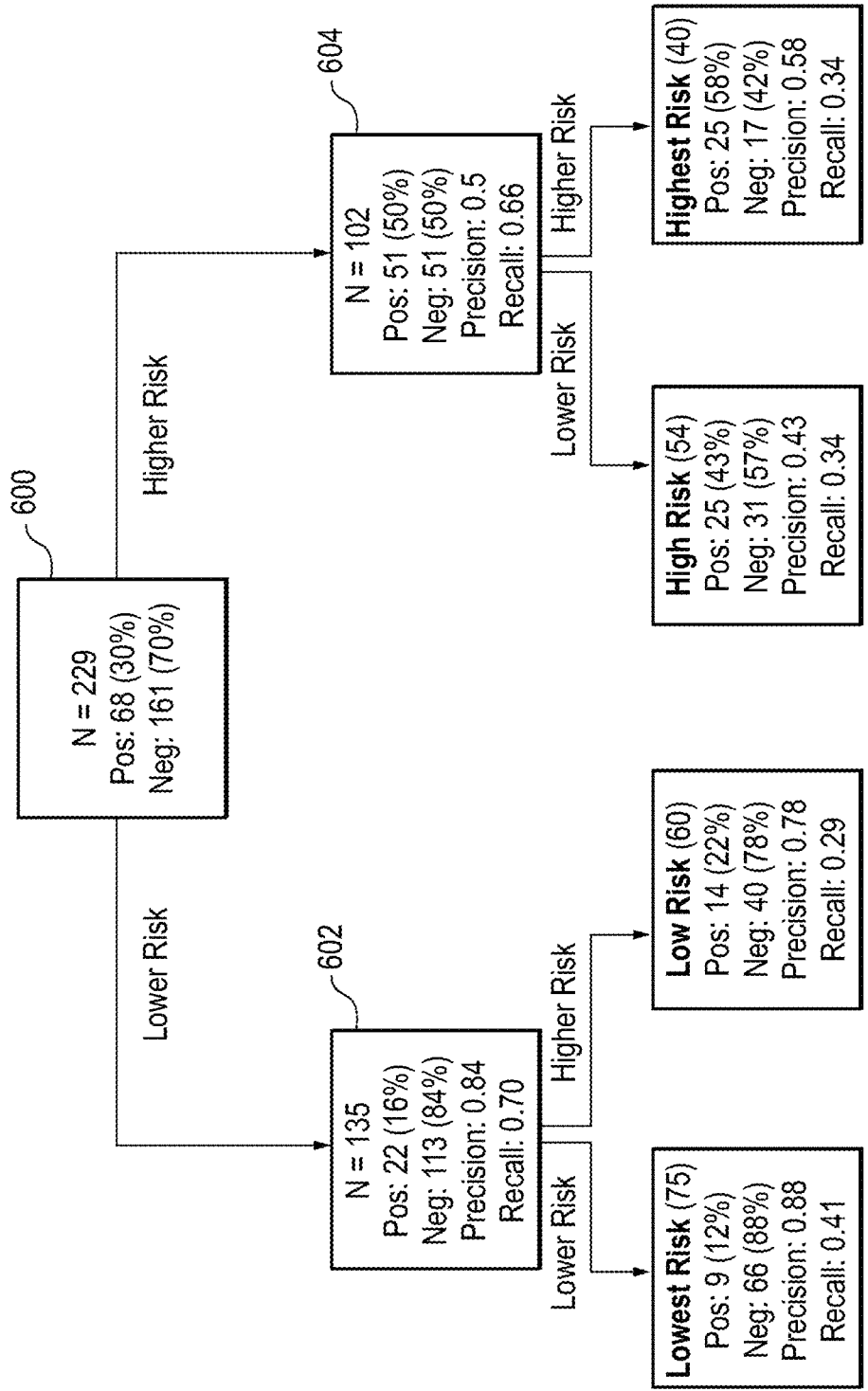
FIG. 16 is a schematic diagram showing the hierarchical combination of binary and child classifiers for predicting any complication; note that this schema follows the configuration of FIG. 6.

FIG. 16 is an illustration of the schema or classification hierarchy for generating a prediction of the risk of any complication during hospitalization of a COVID-19 patient. The schema includes an initial binary classifier 600 (developed in accordance with FIG. 4) and two child classifiers 602 and 604 (developed in accordance with FIG. 5). This schema is in accordance with the schema of FIG. 6. The binary classifier 600 generates lower risk and higher risk group stratification. The child classifiers 602 and 604 further stratify the lower and higher risk groups, respectively, into lower and higher risk groups. If the child classifier 602 classifies the patient as lower risk, the lowest risk prediction is returned, and if it classifies the patient as higher risk, the low risk prediction is returned. If the binary classifier classifies the patient as higher risk, the patient is classified by the child classifier 604, which then produces either a lower risk or higher risk classification. If the higher risk classification is returned, the patient is classified as highest risk. If the lower risk classification is returned, the patient is classified as high risk, as illustrated in FIG. 16.

Figure 15:
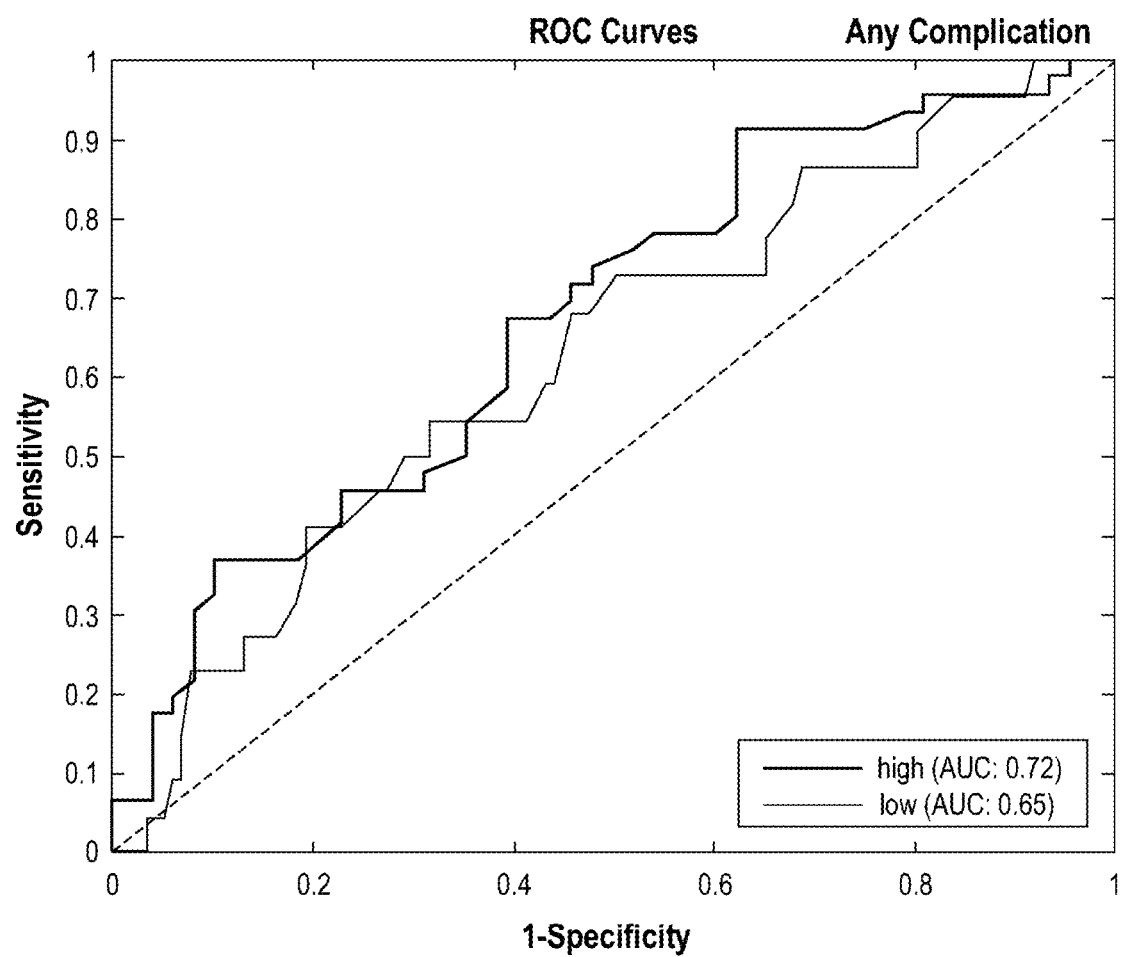
FIG. 15 is a receiver operating characteristic curve for low risk and high risk child classifiers predicting risk of any complication.

FIG. 9 shows the ROC curve for the binary classifier 600 of FIG. 16. FIG. 15 shows the ROC curve for the low and high risk child classifiers 602 and 604 of FIG. 16.

Sixty-eight patients out of the 229 in the development set developed a complication. The initial binary classifier 600 separated these patients into a lower and higher risk group. The lower risk group had 135 patients of which 22 developed a complication. The higher risk group had 101 patients of which 51 developed a complication. Both groups were split again into higher and lower risk groups using the high and low risk child classifiers (602 and 604).

Patients from the lower risk group that were classified as lower risk by the low risk child classifier (602) were assigned to the lowest risk final group consisting of 75 patients of whom 9 developed a complication. The remaining lower risk group patients were assigned to the final low risk group consisting of 60 patients of whom 14 developed a complication. Patients from the higher risk group who were classified as higher risk by the high risk child classifier (604) were assigned to the highest risk final group, consisting of 40 patients of whom 23 developed a complication. The remaining higher risk group patients were assigned to the final high risk group, consisting of 54 patients of whom 23 developed a complication.

Tables 9 and 10 summarize selected attributes by final group classification.

TABLE 9

Summary of Selected Categorical Attributes for the Classes of the Hierarchical Classifier for Assessment of Risk of Any Complication

| Attribute | Category | lowest N = 75 | low N = 60 | high N = 54 | highest N = 40 |
|---|---|---|---|---|---|
| | | n (proportion of group) | | | |
| | Race | | | | |
| | Race or Ethnicity (choice = White) | 15 (0.200) | 17 (0.283) | 6 (0.111) | 3 (0.075) |
| | Race or Ethnicity (choice = Black or African American) | 9 (0.120) | 6 (0.100) | 22 (0.407) | 15 (0.375) |
| | Race or Ethnicity (choice = Hispanic or Latino) | 35 (0.467) | 30 (0.500) | 16 (0.296) | 13 (0.325) |
| | Race or Ethnicity (choice = Other) | 11 (0.147) | 6 (0.100) | 8 (0.148) | 6 (0.150) |
| | Race or Ethnicity (choice = Unknown) | 5 (0.067) | 1 (0.017) | 2 (0.037) | 3 (0.075) |
| sex_or_gender | | | | | |
| | Male | 35 (0.467) | 26 (0.433) | 35 (0.648) | 28 (0.700) |
| | Female | 40 (0.533) | 34 (0.567) | 19 (0.352) | 12 (0.300) |
| Comorbidities (choice = None) | | | | | |
| | 0 | 62 (0.827) | 46 (0.767) | 46 (0.852) | 37 (0.925) |
| | 1 | 13 (0.173) | 14 (0.233) | 8 (0.148) | 3 (0.075) |
| Comorbidities (choice = Hypertension) | | | | | |
| | 1 | 22 (0.293) | 23 (0.383) | 31 (0.574) | 24 (0.600) |
| | 0 | 53 (0.707) | 37 (0.617) | 23 (0.426) | 16 (0.400) |
| Comorbidities (choice = Hyperlipidemia) | | | | | |
| | 0 | 63 (0.840) | 49 (0.817) | 40 (0.741) | 30 (0.750) |
| | 1 | 12 (0.160) | 11 (0.183) | 14 (0.259) | 10 (0.250) |
| Comorbidities (choice = Type 2 Diabetes) | | | | | |
| | 0 | 52 (0.693) | 42 (0.700) | 31 (0.574) | 22 (0.550) |
| | 1 | 23 (0.307) | 18 (0.300) | 23 (0.426) | 18 (0.450) |
| Comorbidities (choice = Cardiovascular Disease) | | | | | |
| | 0 | 69 (0.920) | 55 (0.917) | 46 (0.852) | 33 (0.825) |
| | 1 | 6 (0.080) | 5 (0.083) | 8 (0.148) | 7 (0.175) |
| Comorbidities (choice = Respiratory Disease) | | | | | |
| | 0 | 61 (0.813) | 46 (0.767) | 45 (0.833) | 28 (0.700) |
| | 1 | 14 (0.187) | 14 (0.233) | 9 (0.167) | 12 (0.300) |
| Comorbidities (choice = Gastrointestinal Disease) | | | | | |
| | 0 | 63 (0.840) | 51 (0.850) | 48 (0.889) | 38 (0.950) |
| | 1 | 12 (0.160) | 9 (0.150) | 6 (0.111) | 2 (0.050) |

TABLE 9-continued

Summary of Selected Categorical Attributes for the Classes of the
Hierarchical Classifier for Assessment of Risk of Any Complication

| Attribute | Category | lowest<br>N = 75 | low<br>N = 60 | high<br>N = 54 | highest<br>N = 40 |
|---|---|---|---|---|---|
| Comorbidities (choice = Renal Disease) | | | | | |
| | 0 | 71 (0.947) | 54 (0.900) | 47 (0.870) | 33 (0.825) |
| | 1 | 4 (0.053) | 6 (0.100) | 7 (0.130) | 7 (0.175) |
| Comorbidities (choice = Endocrine Disease (Excluding Diabetes)) | | | | | |
| | 0 | 68 (0.907) | 57 (0.950) | 51 (0.944) | 38 (0.950) |
| | 1 | 7 (0.093) | 3 (0.050) | 3 (0.056) | 2 (0.050) |
| Comorbidities (choice = Neurologic Disease) | | | | | |
| | 0 | 66 (0.880) | 51 (0.850) | 44 (0.815) | 33 (0.825) |
| | 1 | 9 (0.120) | 9 (0.150) | 10 (0.185) | 7 (0.175) |
| Comorbidities (choice = Psychiatric Disease) | | | | | |
| | 0 | 66 (0.880) | 52 (0.867) | 49 (0.907) | 37 (0.925) |
| | 1 | 9 (0.120) | 8 (0.133) | 5 (0.093) | 3 (0.075) |
| Comorbidities (choice = Cancer) | | | | | |
| | 0 | 71 (0.947) | 55 (0.917) | 47 (0.870) | 39 (0.975) |
| | 1 | 4 (0.053) | 5 (0.083) | 7 (0.130) | 1 (0.025) |
| Comorbidities (choice = Infectious Disease) | | | | | |
| | 0 | 72 (0.960) | 58 (0.967) | 53 (0.981) | 38 (0.950) |
| | 1 | 3 (0.040) | 2 (0.033) | 1 (0.019) | 2 (0.050) |
| Comorbidities (choice = Autoimmune Disease) | | | | | |
| | 0 | 72 (0.960) | 57 (0.950) | 54 (1.000) | 39 (0.975) |
| | 1 | 3 (0.040) | 3 (0.050) | 0 (0.000) | 1 (0.025) |
| Comorbidities (choice = Arthritis) | | | | | |
| | 0 | 70 (0.933) | 58 (0.967) | 48 (0.889) | 37 (0.925) |
| | 1 | 5 (0.067) | 2 (0.033) | 6 (0.111) | 3 (0.075) |
| Comorbidities (choice = Chronic Pain Syndrome) | | | | | |
| | 0 | 71 (0.947) | 56 (0.933) | 52 (0.963) | 39 (0.975) |
| | 1 | 4 (0.053) | 4 (0.067) | 2 (0.037) | 1 (0.025) |
| Comorbidities (choice = Morbid Obesity) | | | | | |
| | 0 | 63 (0.840) | 56 (0.933) | 41 (0.759) | 33 (0.825) |
| | 1 | 12 (0.160) | 4 (0.067) | 13 (0.241) | 7 (0.175) |
| Symptoms at presentation (choice = Shortness of breath) | | | | | |
| | 0 | 30 (0.400) | 22 (0.367) | 23 (0.426) | 10 (0.250) |
| | 1 | 45 (0.600) | 38 (0.633) | 31 (0.574) | 30 (0.750) |
| Symptoms at presentation (choice = Fever) | | | | | |
| | 0 | 27 (0.360) | 16 (0.267) | 20 (0.370) | 16 (0.400) |
| | 1 | 48 (0.640) | 44 (0.733) | 34 (0.630) | 24 (0.600) |
| Symptoms at presentation (choice = Cough) | | | | | |
| | 0 | 21 (0.280) | 12 (0.200) | 12 (0.222) | 12 (0.300) |
| | 1 | 54 (0.720) | 48 (0.800) | 42 (0.778) | 28 (0.700) |
| Symptoms at presentation (choice = AMS/Confusion) | | | | | |
| | 0 | 74 (0.987) | 58 (0.967) | 47 (0.870) | 35 (0.875) |
| | 1 | 1 (0.013) | 2 (0.033) | 7 (0.130) | 5 (0.125) |

TABLE 9-continued

Summary of Selected Categorical Attributes for the Classes of the
Hierarchical Classifier for Assessment of Risk of Any Complication

| | | lowest | low | high | highest |
|---|---|---|---|---|---|
| | | | n (proportion of group) | | |
| Attribute | Category | N = 75 | N = 60 | N = 54 | N = 40 |
| Symptoms at presentation (choice = Headache) | | | | | |
| | 0 | 65 (0.867) | 54 (0.900) | 44 (0.815) | 39 (0.975) |
| | 1 | 10 (0.133) | 6 (0.100) | 10 (0.185) | 1 (0.025) |
| Symptoms at presentation (choice = Myalgia) | | | | | |
| | 1 | 25 (0.333) | 11 (0.183) | 7 (0.130) | 2 (0.050) |
| | 0 | 50 (0.667) | 49 (0.817) | 47 (0.870) | 38 (0.950) |
| Symptoms at presentation (choice = Chills) | | | | | |
| | 0 | 55 (0.733) | 49 (0.817) | 39 (0.722) | 36 (0.900) |
| | 1 | 20 (0.267) | 11 (0.183) | 15 (0.278) | 4 (0.100) |
| Symptoms at presentation (choice = Diarrhea) | | | | | |
| | 0 | 62 (0.827) | 46 (0.767) | 42 (0.778) | 29 (0.725) |
| | 1 | 13 (0.173) | 14 (0.233) | 12 (0.222) | 11 (0.275) |
| Symptoms at presentation (choice = Sore Throat) | | | | | |
| | 0 | 73 (0.973) | 59 (0.983) | 52 (0.963) | 39 (0.975) |
| | 1 | 2 (0.027) | 1 (0.017) | 2 (0.037) | 1 (0.025) |
| Symptoms at presentation (choice = Chest pain) | | | | | |
| | 0 | 67 (0.893) | 53 (0.883) | 47 (0.870) | 39 (0.975) |
| | 1 | 8 (0.107) | 7 (0.117) | 7 (0.130) | 1 (0.025) |
| Symptoms at presentation (choice = Fatigue) | | | | | |
| | 1 | 28 (0.373) | 14 (0.233) | 20 (0.370) | 7 (0.175) |
| | 0 | 47 (0.627) | 46 (0.767) | 34 (0.630) | 33 (0.825) |
| Symptoms at presentation (choice = Headache)_1 | | | | | |
| | 1 | 4 (0.053) | 5 (0.083) | 3 (0.056) | 0 (0.000) |
| | 0 | 71 (0.947) | 55 (0.917) | 51 (0.944) | 40 (1.000) |
| Symptoms at presentation (choice = Other) | | | | | |
| | 0 | 45 (0.600) | 37 (0.617) | 32 (0.593) | 24 (0.600) |
| | 1 | 30 (0.400) | 23 (0.383) | 22 (0.407) | 16 (0.400) |
| egfr | | | | | |
| | x >= 60 | 69 (0.920) | 56 (0.933) | 39 (0.722) | 16 (0.400) |
| | 30 >= x > 60 | 2 (0.027) | 4 (0.067) | 10 (0.185) | 18 (0.450) |
| | x < 30 | 4 (0.053) | 0 (0.000) | 5 (0.093) | 6 (0.150) |

TABLE 10

Summary of Selected Numeric Attributes for the Classes of the Hierarchical
Classifier of Assessment of Risk for Any Complication (p values
compare lowest risk group with others (low + high + highest)
and highest risk group with others (lowest + low + high)

| Attribute | Class | Mean | Median | IQR | Mann-Whitney p |
|---|---|---|---|---|---|
| age | | | | | |
| | lowest | 49 | 48 | 25 | <0.001 |
| | low | 51 | 54 | 26 | |
| | high | 66 | 65 | 20 | |
| | highest | 63 | 63 | 21 | 0.004 |

TABLE 10-continued

Summary of Selected Numeric Attributes for the Classes of the Hierarchical Classifier of Assessment of Risk for Any Complication (p values compare lowest risk group with others (low + high + highest) and highest risk group with others (lowest + low + high)

| Attribute | Class | Mean | Median | IQR | Mann-Whitney p |
|---|---|---|---|---|---|
| ed_temperature_c | | | | | |
| | lowest | 37 | 37 | 0.88 | 0.013 |
| | low | 37 | 37 | 1.0 | |
| | high | 37 | 37 | 1.0 | |
| | highest | 37 | 37 | 1.1 | 0.565 |
| ed_heart_rate | | | | | |
| | lowest | 96 | 96 | 28 | 0.136 |
| | low | 100 | 100 | 27 | |
| | high | 96 | 95 | 26 | |
| | highest | 110 | 110 | 37 | 0.038 |
| ed_systolic_bp | | | | | |
| | lowest | 130 | 130 | 34 | 0.366 |
| | low | 140 | 130 | 26 | |
| | high | 140 | 130 | 31 | |
| | highest | 130 | 130 | 23 | 0.936 |
| ed_diastolic_bp | | | | | |
| | lowest | 76 | 75 | 21 | 0.284 |
| | low | 74 | 74 | 16 | |
| | high | 74 | 74 | 17 | |
| | highest | 75 | 74 | 19 | 0.927 |
| ed_respiratory_rate | | | | | |
| | lowest | 21 | 20 | 4.8 | 0.486 |
| | low | 21 | 20 | 6.0 | |
| | high | 21 | 20 | 6.0 | |
| | highest | 26 | 24 | 11 | <0.001 |
| ed_oxygen_saturation | | | | | |
| | lowest | 92 | 93 | 5.0 | 0.002 |
| | low | 91 | 92 | 6.0 | |
| | high | 90 | 91 | 7.0 | |
| | highest | 81 | 85 | 16 | <0.001 |
| weight_kg | | | | | |
| | lowest | 84 | 78 | 17 | 0.059 |
| | low | 79 | 79 | 20 | |
| | high | 96 | 99 | 32 | |
| | highest | 91 | 93 | 35 | 0.236 |
| initial_qtc | | | | | |
| | lowest | 440 | 430 | 43 | 0.048 |
| | low | 440 | 440 | 28 | |
| | high | 450 | 450 | 28 | |
| | highest | 450 | 450 | 44 | 0.275 |
| sodium | | | | | |
| | lowest | 140 | 140 | 4.0 | 0.908 |
| | low | 140 | 140 | 4.0 | |
| | high | 140 | 140 | 4.0 | |
| | highest | 140 | 140 | 5.5 | 0.454 |
| potassium | | | | | |
| | lowest | 3.8 | 3.8 | 0.5 | 0.931 |
| | low | 3.7 | 3.7 | 0.6 | |
| | high | 3.8 | 3.7 | 0.6 | |
| | highest | 4.0 | 3.9 | 0.55 | 0.006 |
| carbon_dioxide_bicarb | | | | | |
| | lowest | 24 | 24 | 3.0 | <0.001 |
| | low | 22 | 22 | 2.5 | |
| | high | 23 | 23 | 3.0 | |
| | highest | 22 | 22 | 5.0 | 0.043 |
| bun | | | | | |
| | lowest | 14 | 12 | 6.8 | <0.001 |
| | low | 13 | 13 | 8.0 | |
| | high | 22 | 15 | 15 | |
| | highest | 34 | 28 | 21 | <0.001 |
| creatinine | | | | | |
| | lowest | 0.89 | 0.77 | 0.40 | <0.001 |
| | low | 0.82 | 0.79 | 0.34 | |
| | high | 1.2 | 1.0 | 0.56 | |
| | highest | 1.8 | 1.4 | 0.98 | <0.001 |
| anion_gap | | | | | |
| | lowest | 11 | 11 | 3.0 | <0.001 |
| | low | 12 | 12 | 3.0 | |
| | high | 12 | 12 | 3.0 | |
| | highest | 15 | 13 | 3.5 | <0.001 |

TABLE 10-continued

Summary of Selected Numeric Attributes for the Classes of the Hierarchical Classifier of Assessment of Risk for Any Complication (p values compare lowest risk group with others (low + high + highest) and highest risk group with others (lowest + low + high)

| Attribute | Class | Mean | Median | IQR | Mann-Whitney p |
|---|---|---|---|---|---|
| wbc_screen | | | | | |
| | lowest | 5.7 | 5.6 | 2.5 | <0.001 |
| | low | 9.5 | 7.3 | 4.6 | |
| | high | 7.6 | 7.0 | 3.1 | |
| | highest | 10 | 8.7 | 4.9 | <0.001 |
| hemoglobin | | | | | |
| | lowest | 15 | 15 | 1.9 | 0.059 |
| | low | 14 | 14 | 2.8 | |
| | high | 14 | 14 | 2.6 | |
| | highest | 15 | 15 | 2.6 | 0.314 |
| hematocrit | | | | | |
| | lowest | 44 | 44 | 4.9 | 0.088 |
| | low | 42 | 42 | 8.0 | |
| | high | 43 | 43 | 7.3 | |
| | highest | 45 | 45 | 8.5 | 0.087 |
| platelet_count | | | | | |
| | lowest | 200 | 190 | 75 | 0.015 |
| | low | 250 | 230 | 99 | |
| | high | 230 | 230 | 110 | |
| | highest | 200 | 180 | 160 | 0.224 |
| initial_ldh | | | | | |
| | lowest | 310 | 310 | 110 | 0.008 |
| | low | 330 | 290 | 180 | |
| | high | 330 | 310 | 170 | |
| | highest | 550 | 460 | 300 | <0.001 |
| initial_d_dimer | | | | | |
| | lowest | 1000 | 630 | 520 | <0.001 |
| | low | 1100 | 830 | 830 | |
| | high | 1300 | 910 | 1100 | |
| | highest | 7600 | 1400 | 2500 | <0.001 |
| initial_c_reactive_protein | | | | | |
| | lowest | 50 | 48 | 48 | <0.001 |
| | low | 120 | 100 | 110 | |
| | high | 110 | 93 | 93 | |
| | highest | 180 | 150 | 150 | <0.001 |
| ferritin | | | | | |
| | lowest | 480 | 350 | 400 | 0.277 |
| | low | 560 | 260 | 460 | |
| | high | 500 | 360 | 360 | |
| | highest | 2300 | 850 | 1000 | <0.001 |

Predicting Risk of ARDS

Figure 17:
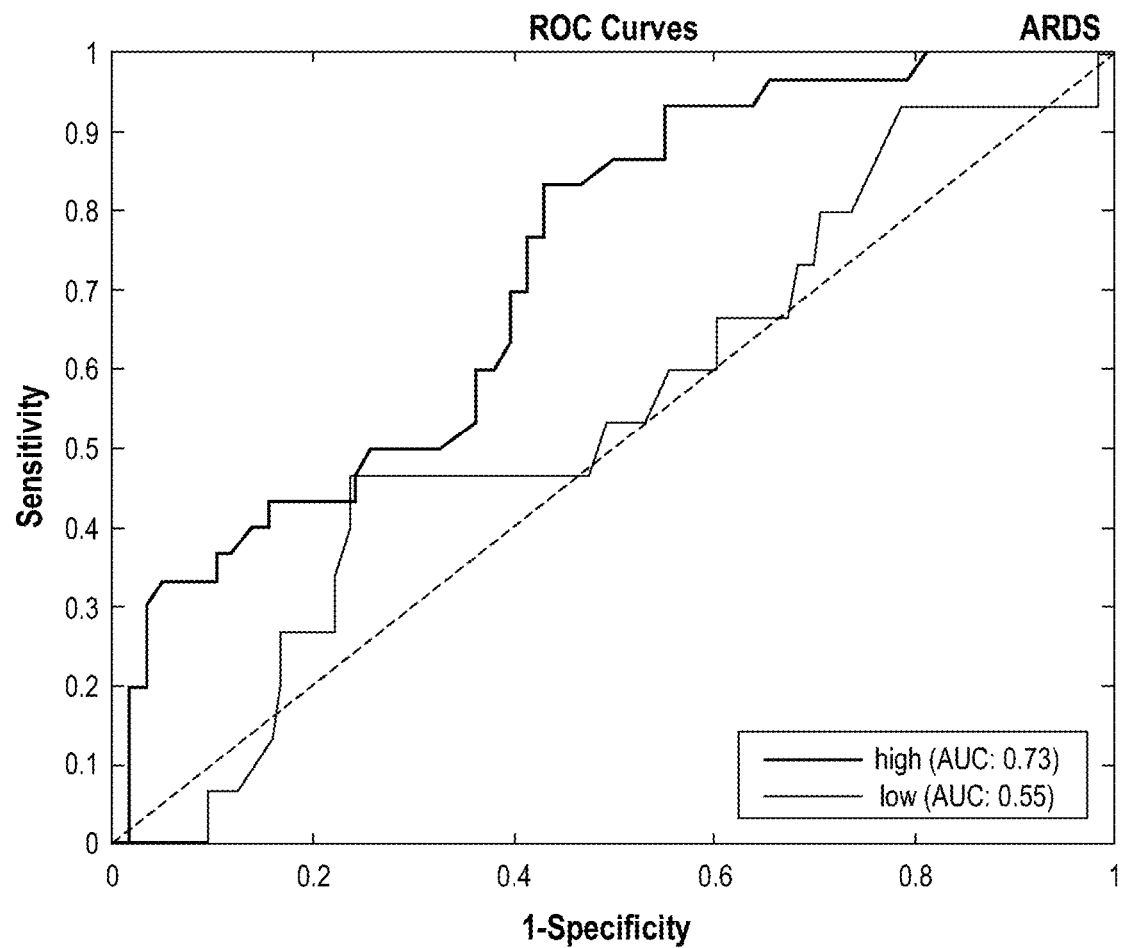
FIG. 17 is a receiver operating characteristic curve for low risk and high risk child classifiers predicting risk of ARDS.
Figure 18:
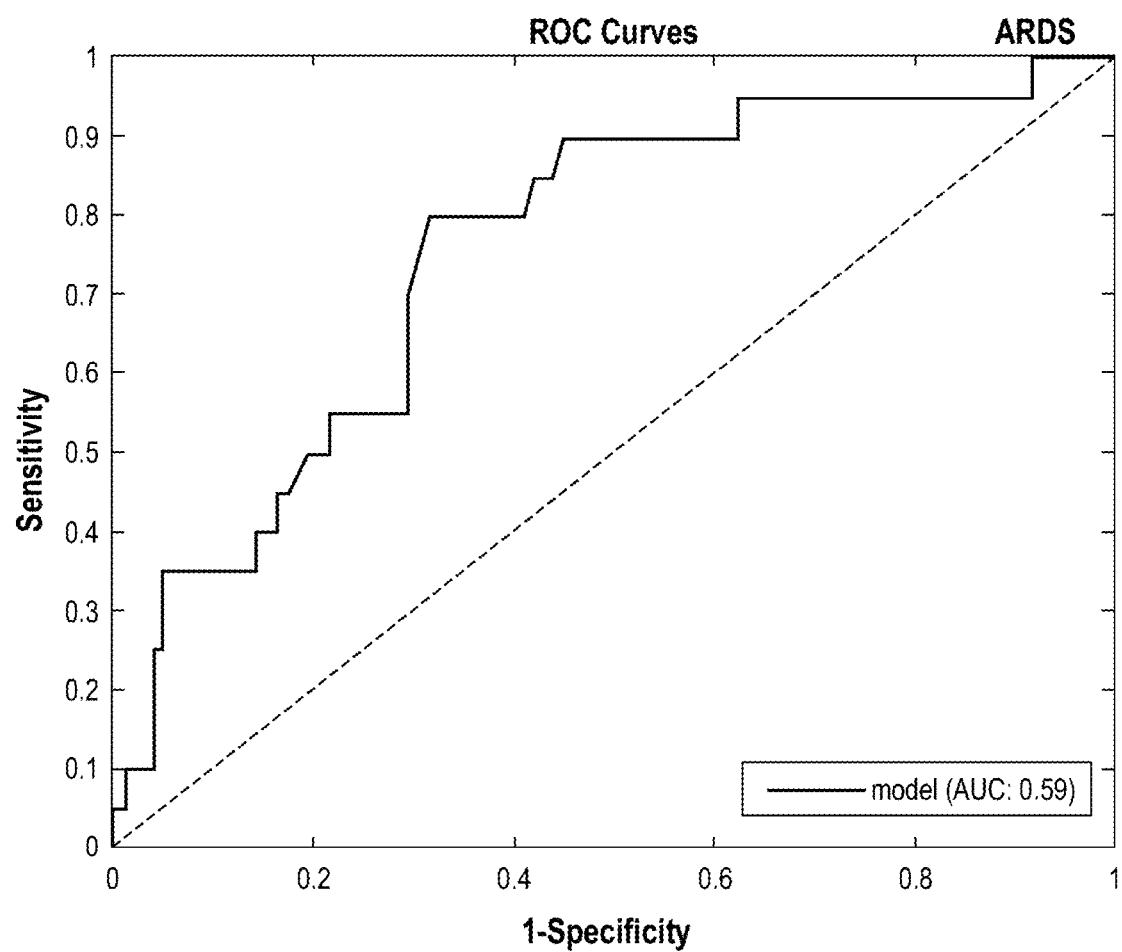
FIG. 18 is a receiver operating characteristic curve for an intermediate risk classifier predicting ARDS.
Figure 19:
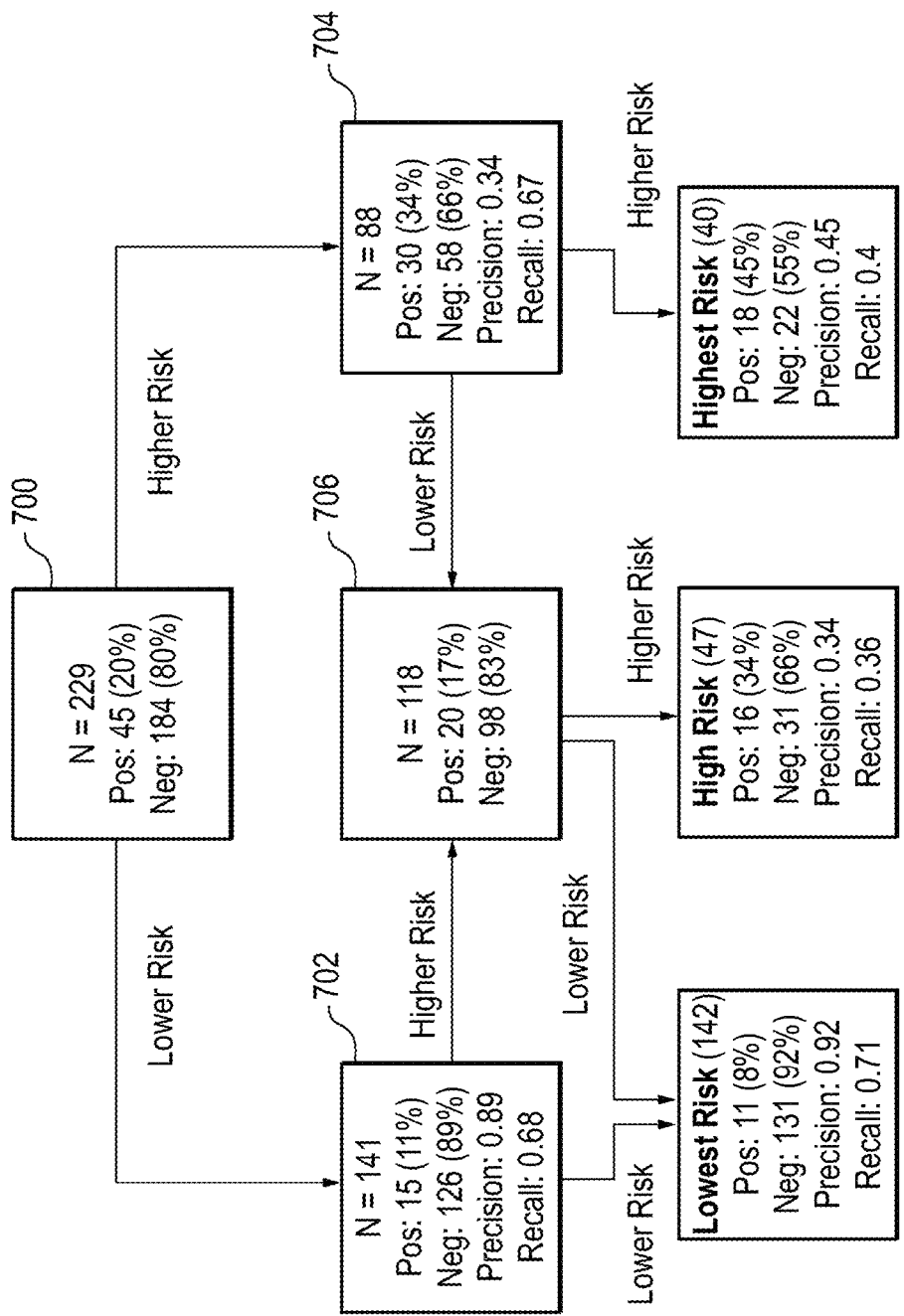
FIG. 19 is a schematic diagram showing the hierarchical combination of binary, child, and intermediate classifiers for predicting risk of ARDS; note that this schema follows the configuration of FIG. 7.

The hierarchical classifier to predict risk of developing acute respiratory distress syndrome (ARDS) used the configuration shown in FIG. 19, which is basically an embodiment of the hierarchical schema shown in FIG. 7. The classifier includes an initial binary classifier 700, low risk child classifier 702, high risk child classifier 704, and an intermediate child classifier 706. ROC curves for the binary classifier 700 is shown in FIG. 10, and ROC curves for the high and low risk child classifiers 702 and 704 are shown in FIG. 17, and the ROC curve for the intermediate risk classifier 706 is shown in FIG. 18. FIG. 19 schematically shows how the patients are split into the three final groups, namely lowest risk, high risk, and highest risk.

Classifier 700 was developed and trained in accordance with FIG. 4; child and intermediate classifiers 702, 704, and 706 were developed and trained in accordance with FIG. 5.

Forty-five patients out of the 229 in the development set developed ARDS. The initial binary classifier 700 separated these patients into a lower and higher risk group. The lower risk group had 141 patients of whom 15 developed ARDS. The higher risk group had 88 patients of whom 30 developed ARDS. Both groups were split again into higher and lower risk groups using the high and low risk child classifiers, 704 and 702 respectively.

Patients from the lower risk group who were classified as lower risk by the low risk child classifier 702 were assigned to the lowest risk final group. Patients from the higher risk group who were classified as higher risk by the high risk child classifier 704 were assigned to the highest risk final group, consisting of 40 patients of whom 18 developed ARDS.

The remaining two groups were combined into a group of 118 patients of whom 20 developed ARDS. This group of patents was split into a higher and lower risk group by the intermediate classifier 706. Patients classified by intermediate classifier 706 in the higher risk group were assigned to the final high risk group consisting of 47 patients of whom 16 developed ARDS. Patients classified by the intermediate classifier 706 in the lower risk group were assigned to the final lowest risk group (combined with those already assigned to this group by the low risk child classifier 702 as shown in FIG. 19). The lowest risk final group had 142 patients of whom 11 developed ARDS.

Tables 11 and 12 summarize selected attributes by final group classification.

TABLE 11

Summary of Selected Categorical Attributes for the Classes of
the Hierarchical Classifier for Assessment of Risk of ARDS

| Attribute | Category | lowest | high | highest |
|---|---|---|---|---|
| | | n (proportion of group) | | |
| | | N = 142 | N = 47 | N = 40 |
| Race | | | | |
| | Race or Ethnicity (choice = White) | 30 (0.211) | 9 (0.191) | 2 (0.050) |
| | Race or Ethnicity (choice = Black or African American) | 27 (0.190) | 10 (0.213) | 15 (0.375) |
| | Race or Ethnicity (choice = Hispanic or Latino) | 59 (0.415) | 21 (0.447) | 14 (0.350) |
| | Race or Ethnicity (choice = Other) | 18 (0.127) | 7 (0.149) | 6 (0.150) |
| | Race or Ethnicity (choice = Unknown) | 8 (0.056) | 0 (0.000) | 3 (0.075) |
| sex_or_gender | | | | |
| | Male | 71 (0.500) | 24 (0.511) | 29 (0.725) |
| | Female | 71 (0.500) | 23 (0.489) | 11 (0.275) |
| Comorbidities (choice = None) | | | | |
| | 0 | 120 (0.845) | 39 (0.830) | 32 (0.800) |
| | 1 | 22 (0.155) | 8 (0.170) | 8 (0.200) |
| Comorbidities (choice = Hypertension) | | | | |
| | 1 | 59 (0.415) | 18 (0.383) | 23 (0.575) |
| | 0 | 83 (0.585) | 29 (0.617) | 17 (0.425) |
| Comorbidities (choice = Hyperlipidemia) | | | | |
| | 0 | 114 (0.803) | 37 (0.787) | 31 (0.775) |
| | 1 | 28 (0.197) | 10 (0.213) | 9 (0.225) |
| Comorbidities (choice = Type 2 Diabetes) | | | | |
| | 0 | 91 (0.641) | 30 (0.638) | 26 (0.650) |
| | 1 | 51 (0.359) | 17 (0.362) | 14 (0.350) |
| Comorbidities (choice = Cardiovascular Disease) | | | | |
| | 0 | 125 (0.880) | 42 (0.894) | 36 (0.900) |
| | 1 | 17 (0.120) | 5 (0.106) | 4 (0.100) |
| Comorbidities (choice = Respiratory Disease) | | | | |
| | 0 | 109 (0.768) | 41 (0.872) | 30 (0.750) |
| | 1 | 33 (0.232) | 6 (0.128) | 10 (0.250) |
| Comorbidities (choice = Gastrointestinal Disease) | | | | |
| | 0 | 122 (0.859) | 39 (0.830) | 39 (0.975) |
| | 1 | 20 (0.141) | 8 (0.170) | 1 (0.025) |
| Comorbidities (choice = Renal Disease) | | | | |
| | 0 | 130 (0.915) | 40 (0.851) | 35 (0.875) |
| | 1 | 12 (0.085) | 7 (0.149) | 5 (0.125) |
| Comorbidities (choice = Endocrine Disease (Excluding Diabetes)) | | | | |
| | 0 | 131 (0.923) | 45 (0.957) | 38 (0.950) |
| | 1 | 11 (0.077) | 2 (0.043) | 2 (0.050) |
| Comorbidities (choice = Neurologic Disease) | | | | |
| | 0 | 119 (0.838) | 39 (0.830) | 36 (0.900) |
| | 1 | 23 (0.162) | 8 (0.170) | 4 (0.100) |
| Comorbidities (choice = Psychiatric Disease) | | | | |
| | 0 | 126 (0.887) | 41 (0.872) | 37 (0.925) |
| | 1 | 16 (0.113) | 6 (0.128) | 3 (0.075) |

TABLE 11-continued

Summary of Selected Categorical Attributes for the Classes of
the Hierarchical Classifier for Assessment of Risk of ARDS

| | | lowest | high | highest |
|---|---|---|---|---|
| | | n (proportion of group) | | |
| Attribute | Category | N = 142 | N = 47 | N = 40 |
| Comorbidities (choice = Cancer) | | | | |
| | 0 | 131 (0.923) | 42 (0.894) | 39 (0.975) |
| | 1 | 11 (0.077) | 5 (0.106) | 1 (0.025) |
| Comorbidities (choice = Infectious Disease) | | | | |
| | 0 | 135 (0.951) | 47 (1.000) | 39 (0.975) |
| | 1 | 7 (0.049) | 0 (0.000) | 1 (0.025) |
| Comorbidities (choice = Autoimmune Disease) | | | | |
| | 0 | 139 (0.979) | 43 (0.915) | 40 (1.000) |
| | 1 | 3 (0.021) | 4 (0.085) | 0 (0.000) |
| Comorbidities (choice = Arthritis) | | | | |
| | 0 | 132 (0.930) | 42 (0.894) | 39 (0.975) |
| | 1 | 10 (0.070) | 5 (0.106) | 1 (0.025) |
| Comorbidities (choice = Chronic Pain Syndrome) | | | | |
| | 0 | 134 (0.944) | 45 (0.957) | 39 (0.975) |
| | 1 | 8 (0.056) | 2 (0.043) | 1 (0.025) |
| Comorbidities (choice = Morbid Obesity) | | | | |
| | 0 | 120 (0.845) | 39 (0.830) | 34 (0.850) |
| | 1 | 22 (0.155) | 8 (0.170) | 6 (0.150) |
| Symptoms at presentation (choice = Shortness of breath) | | | | |
| | 0 | 55 (0.387) | 20 (0.426) | 10 (0.250) |
| | 1 | 87 (0.613) | 27 (0.574) | 30 (0.750) |
| Symptoms at presentation (choice = Fever) | | | | |
| | 0 | 47 (0.331) | 16 (0.340) | 16 (0.400) |
| | 1 | 95 (0.669) | 31 (0.660) | 24 (0.600) |
| Symptoms at presentation (choice = Cough) | | | | |
| | 0 | 33 (0.232) | 15 (0.319) | 9 (0.225) |
| | 1 | 109 (0.768) | 32 (0.681) | 31 (0.775) |
| Symptoms at presentation (choice = AMS/Confusion) | | | | |
| | 0 | 135 (0.951) | 44 (0.936) | 35 (0.875) |
| | 1 | 7 (0.049) | 3 (0.064) | 5 (0.125) |
| Symptoms at presentation (choice = Headache) | | | | |
| | 0 | 122 (0.859) | 43 (0.915) | 37 (0.925) |
| | 1 | 20 (0.141) | 4 (0.085) | 3 (0.075) |
| Symptoms at presentation (choice = Myalgia) | | | | |
| | 1 | 37 (0.261) | 6 (0.128) | 2 (0.050) |
| | 0 | 105 (0.739) | 41 (0.872) | 38 (0.950) |
| Symptoms at presentation (choice = Chills) | | | | |
| | 0 | 105 (0.739) | 39 (0.830) | 35 (0.875) |
| | 1 | 37 (0.261) | 8 (0.170) | 5 (0.125) |
| Symptoms at presentation (choice = Diarrhea) | | | | |
| | 0 | 117 (0.824) | 33 (0.702) | 29 (0.725) |
| | 1 | 25 (0.176) | 14 (0.298) | 11 (0.275) |

TABLE 11-continued

Summary of Selected Categorical Attributes for the Classes of
the Hierarchical Classifier for Assessment of Risk of ARDS

| | | lowest | high | highest |
|---|---|---|---|---|
| | | \multicolumn{3}{c}{n (proportion of group)} | | |
| Attribute | Category | N = 142 | N = 47 | N = 40 |
| Symptoms at presentation (choice = Sore Throat) | | | | |
| | 0 | 138 (0.972) | 47 (1.000) | 38 (0.950) |
| | 1 | 4 (0.028) | 0 (0.000) | 2 (0.050) |
| Symptoms at presentation (choice = Chest pain) | | | | |
| | 0 | 126 (0.887) | 42 (0.894) | 38 (0.950) |
| | 1 | 16 (0.113) | 5 (0.106) | 2 (0.050) |
| Symptoms at presentation (choice = Fatigue) | | | | |
| | 1 | 43 (0.303) | 16 (0.340) | 10 (0.250) |
| | 0 | 99 (0.697) | 31 (0.660) | 30 (0.750) |
| Symptoms at presentation (choice = Headache)_1 | | | | |
| | 1 | 7 (0.049) | 5 (0.106) | 0 (0.000) |
| | 0 | 135 (0.951) | 42 (0.894) | 40 (1.000) |
| Symptoms at presentation (choice = Other) | | | | |
| | 0 | 84 (0.592) | 30 (0.638) | 24 (0.600) |
| | 1 | 58 (0.408) | 17 (0.362) | 16 (0.400) |
| egfr | | | | |
| | x >= 60 | 126 (0.887) | 37 (0.787) | 17 (0.425) |
| | 30 >= x > 60 | 8 (0.056) | 7 (0.149) | 19 (0.475) |
| | x < 30 | 8 (0.056) | 3 (0.064) | 4 (0.100) |

TABLE 12

Summary of Selected Numeric Attributes for the Classes of the Hierarchical Classifier
for Assessment of Risk of ARDS (p values compare lowest risk group with others (low
+ high + highest) and highest risk group with others (lowest + low + high)

| Attribute | Class | Mean | Median | IQR | Mann-Whitney p |
|---|---|---|---|---|---|
| age | | | | | |
| | lowest | 54 | 55 | 31 | 0.024 |
| | high | 58 | 60 | 18 | |
| | highest | 61 | 59 | 22 | 0.05 |
| ed_temperature_c | | | | | |
| | lowest | 37 | 37 | 1.0 | 0.974 |
| | high | 37 | 37 | 1.2 | |
| | highest | 37 | 37 | 1.0 | 0.524 |
| ed_heart_rate | | | | | |
| | lowest | 99 | 98 | 30 | 0.837 |
| | high | 95 | 93 | 23 | |
| | highest | 110 | 110 | 35 | 0.078 |
| ed_systolic_bp | | | | | |
| | lowest | 140 | 140 | 33 | <0.001 |
| | high | 120 | 120 | 21 | |
| | highest | 130 | 130 | 22 | 0.604 |
| ed_diastolic_bp | | | | | |
| | lowest | 77 | 77 | 17 | <0.001 |
| | high | 68 | 68 | 15 | |
| | highest | 75 | 74 | 18 | 0.988 |
| ed_respiratory_rate | | | | | |
| | lowest | 21 | 20 | 6.0 | 0.261 |
| | high | 21 | 18 | 6.0 | |
| | highest | 25 | 24 | 12 | 0.005 |
| ed_oxygen_saturation | | | | | |
| | lowest | 92 | 92 | 5.0 | <0.001 |
| | high | 90 | 92 | 7.0 | |
| | highest | 81 | 85 | 14 | <0.001 |

TABLE 12-continued

Summary of Selected Numeric Attributes for the Classes of the Hierarchical Classifier for Assessment of Risk of ARDS (p values compare lowest risk group with others (low + high + highest) and highest risk group with others (lowest + low + high)

| Attribute | Class | Mean | Median | IQR | Mann-Whitney p |
|---|---|---|---|---|---|
| weight_kg | | | | | |
| | lowest | 86 | 80 | 25 | 0.186 |
| | high | 86 | 84 | 25 | |
| | highest | 92 | 92 | 34 | 0.198 |
| initial_qtc | | | | | |
| | lowest | 450 | 450 | 35 | 0.067 |
| | high | 430 | 430 | 35 | |
| | highest | 450 | 440 | 39 | 0.626 |
| sodium | | | | | |
| | lowest | 140 | 140 | 4.0 | 0.449 |
| | high | 140 | 140 | 3.0 | |
| | highest | 140 | 140 | 6.0 | 1 |
| potassium | | | | | |
| | lowest | 3.7 | 3.7 | 0.50 | 0.039 |
| | high | 3.9 | 3.8 | 0.47 | |
| | highest | 3.9 | 3.8 | 0.80 | 0.203 |
| carbon_dioxide_bicarb | | | | | |
| | lowest | 23 | 23 | 3.0 | <0.001 |
| | high | 22 | 22 | 2.8 | |
| | highest | 21 | 22 | 5.0 | 0.022 |
| bun | | | | | |
| | lowest | 15 | 12 | 7.0 | <0.001 |
| | high | 18 | 15 | 13 | |
| | highest | 33 | 27 | 23 | <0.001 |
| creatinine | | | | | |
| | lowest | 0.94 | 0.82 | 0.42 | <0.001 |
| | high | 1.2 | 0.99 | 0.43 | |
| | highest | 1.7 | 1.3 | 0.7 | <0.001 |
| anion_gap | | | | | |
| | lowest | 12 | 11 | 3.0 | <0.001 |
| | high | 12 | 12 | 3.0 | |
| | highest | 15 | 13 | 4.0 | <0.001 |
| wbc_screen | | | | | |
| | lowest | 6.5 | 6.0 | 2.9 | <0.001 |
| | high | 9.6 | 7.3 | 4.1 | |
| | highest | 11 | 9.8 | 8.0 | <0.001 |
| hemoglobin | | | | | |
| | lowest | 15 | 15 | 2.1 | 0.102 |
| | high | 13 | 14 | 2.4 | |
| | highest | 15 | 15 | 2.4 | 0.035 |
| hematocrit | | | | | |
| | lowest | 43 | 44 | 5.9 | 0.14 |
| | high | 40 | 40 | 5.7 | |
| | highest | 45 | 45 | 8.0 | 0.014 |
| platelet_count | | | | | |
| | lowest | 220 | 210 | 78 | 0.899 |
| | high | 220 | 220 | 130 | |
| | highest | 220 | 200 | 150 | 0.968 |
| initial_ldh | | | | | |
| | lowest | 300 | 290 | 110 | <0.001 |
| | high | 350 | 320 | 180 | |
| | highest | 590 | 500 | 220 | <0.001 |
| initial_d_dimer | | | | | |
| | lowest | 980 | 600 | 490 | <0.001 |
| | high | 2000 | 1000 | 1100 | |
| | highest | 6900 | 1500 | 1600 | <0.001 |
| initial_c_reactive_protein | | | | | |
| | lowest | 65 | 57 | 67 | <0.001 |
| | high | 140 | 130 | 84 | |
| | highest | 210 | 220 | 170 | <0.001 |
| ferritin | | | | | |
| | lowest | 470 | 300 | 400 | <0.001 |
| | high | 650 | 430 | 720 | |
| | highest | 2300 | 850 | 950 | <0.001 |

Predicting Risk of Intubation

Figure 21:
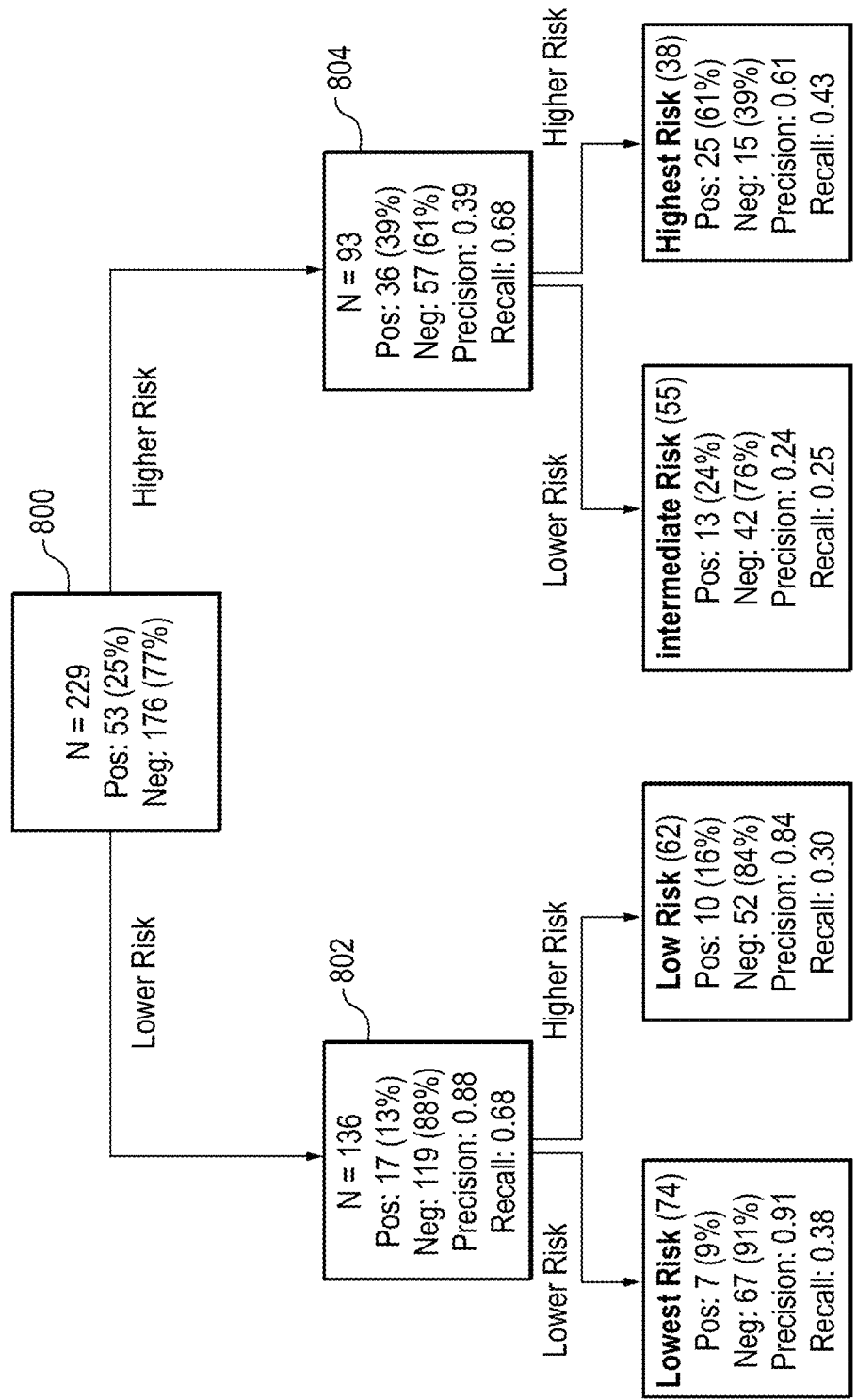
FIG. 21 is a schematic diagram showing the hierarchical combination of binary and child classifiers for predicting risk of intubation; note that this schema follows the configuration of FIG. 6.

The hierarchical classifier to predict risk of the need for mechanical ventilation (intubation) used the configuration shown in FIG. 21, which is in accordance with the schema shown in FIG. 6. This classifier includes an initial binary classifier 800 classifying patients into lower and higher risk groups, and child classifiers 802 and 804. Classifier 800 was developed in accordance with FIG. 4, and child classifiers 802 and 804 were developed in accordance with FIG. 5.

Figure 20:
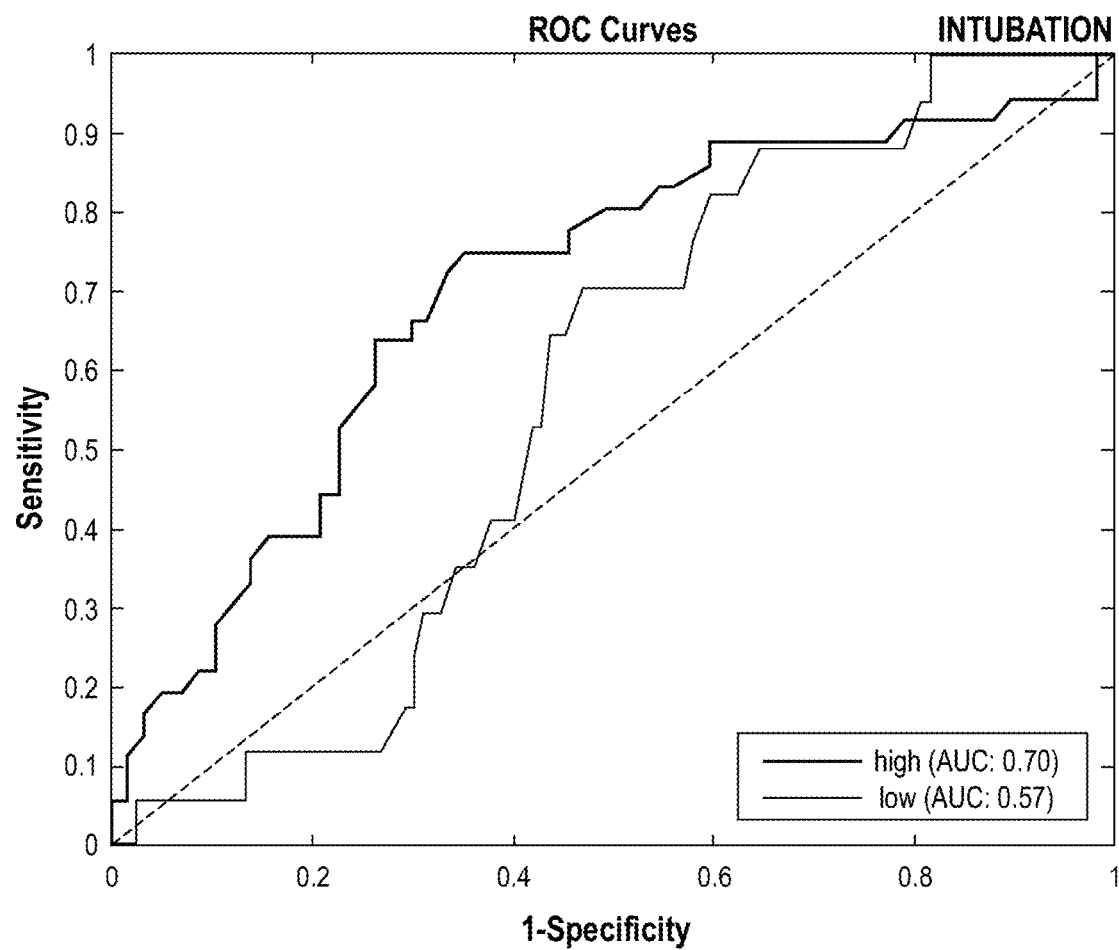
FIG. 20 is a receiver operating characteristic curve for low risk and high risk child classifiers predicting risk of intubation.

ROC curves for the high and low risk child classifiers 802 and 804 are shown in FIG. 20. ROC curves for the binary classifier are shown in FIG. 11. FIG. 21 schematically shows how the patients are split into the four final groups, lowest risk, low risk, intermediate risk and highest risk.

Fifty-three patients out of the 229 in the development set were intubated. The initial binary classifier 800 separated these patients into a lower and higher risk group. The lower risk group had 136 patients of whom 17 were intubated. The higher risk group had 93 patients of whom 36 were intubated. Both groups were split again into higher and lower risk groups using the high and low risk child classifiers, 804 and 802 respectively.

Patients from the lower risk group that were classified as lower risk by the low risk child classifier 802 were assigned to the lowest risk final group consisting of 74 patients of whom 7 were intubated. The remaining lower risk group patients were assigned to the final low risk group consisting of 62 patients of whom 10 were intubated.

Patients from the higher risk group who were classified as higher risk by the high risk child classifier 804 were assigned to the highest risk final group consisting of 38 patients of which 23 were intubated. The remaining higher risk group patients were assigned to the final intermediate risk group consisting of 55 patients of whom 13 were intubated. A label of 'intermediate' was used in this case as the proportion of intubated patients in this group was nearly identical to that of the entire development set.

Tables 13 and 14 summarize selected attributes by final group classification.

TABLE 13

Summary of Selected Categorical Attributes for the Classes of the Hierarchical Classifier for assessment of Risk of Intubation

| Attribute | Category | lowest | low | intermediate | highest |
|---|---|---|---|---|---|
| | | | n (proportion of group) | | |
| | | N = 74 | N = 62 | N = 55 | N = 38 |
| | Race | | | | |
| | Race or Ethnicity (choice = White) | 19 (0.257) | 20 (0.323) | 1 (0.018) | 1 (0.026) |
| | Race or Ethnicity (choice = Black or African American) | 9 (0.122) | 6 (0.097) | 22 (0.400) | 15 (0.395) |
| | Race or Ethnicity (choice = Hispanic or Latino) | 34 (0.459) | 29 (0.468) | 20 (0.364) | 11 (0.289) |
| | Race or Ethnicity (choice = Other) | 7 (0.095) | 4 (0.065) | 12 (0.218) | 8 (0.211) |
| | Race or Ethnicity (choice = Unknown) | 5 (0.068) | 3 (0.048) | 0 (0.000) | 3 (0.079) |
| | sex_or_gender | | | | |
| | Male | 38 (0.514) | 26 (0.419) | 33 (0.600) | 27 (0.711) |
| | Female | 36 (0.486) | 36 (0.581) | 22 (0.400) | 11 (0.289) |
| | Comorbidities (choice = None) | | | | |
| | 0 | 62 (0.838) | 48 (0.774) | 49 (0.891) | 32 (0.842) |
| | 1 | 12 (0.162) | 14 (0.226) | 6 (0.109) | 6 (0.158) |
| | Comorbidities (choice = Hypertension) | | | | |
| | 1 | 25 (0.338) | 22 (0.355) | 31 (0.564) | 22 (0.579) |
| | 0 | 49 (0.662) | 40 (0.645) | 24 (0.436) | 16 (0.421) |
| | Comorbidities (choice = Hyperlipidemia) | | | | |
| | 0 | 60 (0.811) | 51 (0.823) | 43 (0.782) | 28 (0.737) |
| | 1 | 14 (0.189) | 11 (0.177) | 12 (0.218) | 10 (0.263) |
| | Comorbidities (choice = Type 2 Diabetes) | | | | |
| | 0 | 52 (0.703) | 42 (0.677) | 31 (0.564) | 22 (0.579) |
| | 1 | 22 (0.297) | 20 (0.323) | 24 (0.436) | 16 (0.421) |
| | Comorbidities (choice = Cardiovascular Disease) | | | | |
| | 0 | 66 (0.892) | 55 (0.887) | 49 (0.891) | 33 (0.868) |
| | 1 | 8 (0.108) | 7 (0.113) | 6 (0.109) | 5 (0.132) |
| | Comorbidities (choice = Respiratory Disease) | | | | |
| | 0 | 60 (0.811) | 48 (0.774) | 43 (0.782) | 29 (0.763) |
| | 1 | 14 (0.189) | 14 (0.226) | 12 (0.218) | 9 (0.237) |
| | Comorbidities (choice = Gastrointestinal Disease) | | | | |
| | 0 | 61 (0.824) | 54 (0.871) | 49 (0.891) | 36 (0.947) |
| | 1 | 13 (0.176) | 8 (0.129) | 6 (0.109) | 2 (0.053) |
| | Comorbidities (choice = Renal Disease) | | | | |
| | 0 | 66 (0.892) | 56 (0.903) | 50 (0.909) | 33 (0.868) |
| | 1 | 8 (0.108) | 6 (0.097) | 5 (0.091) | 5 (0.132) |
| | Comorbidities (choice = Endocrine Disease (Excluding Diabetes)) | | | | |
| | 0 | 68 (0.919) | 57 (0.919) | 52 (0.945) | 37 (0.974) |
| | 1 | 6 (0.081) | 5 (0.081) | 3 (0.055) | 1 (0.026) |

TABLE 13-continued

Summary of Selected Categorical Attributes for the Classes of the
Hierarchical Classifier for assessment of Risk of Intubation

|  |  | lowest | low | intermediate | highest |
|---|---|---|---|---|---|
|  |  | | n (proportion of group) | | |
| Attribute | Category | N = 74 | N = 62 | N = 55 | N = 38 |
| Comorbidities (choice = Neurologic Disease) | | | | | |
| | 0 | 62 (0.838) | 52 (0.839) | 46 (0.836) | 34 (0.895) |
| | 1 | 12 (0.162) | 10 (0.161) | 9 (0.164) | 4 (0.105) |
| Comorbidities (choice = Psychiatric Disease) | | | | | |
| | 0 | 64 (0.865) | 53 (0.855) | 51 (0.927) | 36 (0.947) |
| | 1 | 10 (0.135) | 9 (0.145) | 4 (0.073) | 2 (0.053) |
| Comorbidities (choice = Cancer) | | | | | |
| | 0 | 68 (0.919) | 57 (0.919) | 50 (0.909) | 37 (0.974) |
| | 1 | 6 (0.081) | 5 (0.081) | 5 (0.091) | 1 (0.026) |
| Comorbidities (choice = Infectious Disease) | | | | | |
| | 0 | 70 (0.946) | 61 (0.984) | 53 (0.964) | 37 (0.974) |
| | 1 | 4 (0.054) | 1 (0.016) | 2 (0.036) | 1 (0.026) |
| Comorbidities (choice = Autoimmune Disease) | | | | | |
| | 0 | 71 (0.959) | 60 (0.968) | 54 (0.982) | 37 (0.974) |
| | 1 | 3 (0.041) | 2 (0.032) | 1 (0.018) | 1 (0.026) |
| Comorbidities (choice = Arthritis) | | | | | |
| | 0 | 70 (0.946) | 57 (0.919) | 49 (0.891) | 37 (0.974) |
| | 1 | 4 (0.054) | 5 (0.081) | 6 (0.109) | 1 (0.026) |
| Comorbidities (choice = Chronic Pain Syndrome) | | | | | |
| | 0 | 70 (0.946) | 58 (0.935) | 53 (0.964) | 37 (0.974) |
| | 1 | 4 (0.054) | 4 (0.065) | 2 (0.036) | 1 (0.026) |
| Comorbidities (choice = Morbid Obesity) | | | | | |
| | 0 | 64 (0.865) | 55 (0.887) | 43 (0.782) | 31 (0.816) |
| | 1 | 10 (0.135) | 7 (0.113) | 12 (0.218) | 7 (0.184) |
| Symptoms at presentation (choice = Shortness of breath) | | | | | |
| | 0 | 33 (0.446) | 24 (0.387) | 19 (0.345) | 9 (0.237) |
| | 1 | 41 (0.554) | 38 (0.613) | 36 (0.655) | 29 (0.763) |
| Symptoms at presentation (choice = Fever) | | | | | |
| | 0 | 26 (0.351) | 18 (0.290) | 20 (0.364) | 15 (0.395) |
| | 1 | 48 (0.649) | 44 (0.710) | 35 (0.636) | 23 (0.605) |
| Symptoms at presentation (choice = Cough) | | | | | |
| | 0 | 20 (0.270) | 15 (0.242) | 14 (0.255) | 8 (0.211) |
| | 1 | 54 (0.730) | 47 (0.758) | 41 (0.745) | 30 (0.789) |
| Symptoms at presentation (choice = AMS/Confusion) | | | | | |
| | 0 | 71 (0.959) | 58 (0.935) | 51 (0.927) | 34 (0.895) |
| | 1 | 3 (0.041) | 4 (0.065) | 4 (0.073) | 4 (0.105) |
| Symptoms at presentation (choice = Headache) | | | | | |
| | 0 | 66 (0.892) | 57 (0.919) | 44 (0.800) | 35 (0.921) |
| | 1 | 8 (0.108) | 5 (0.081) | 11 (0.200) | 3 (0.079) |
| Symptoms at presentation (choice = Myalgia) | | | | | |
| | 1 | 23 (0.311) | 10 (0.161) | 10 (0.182) | 2 (0.053) |
| | 0 | 51 (0.689) | 52 (0.839) | 45 (0.818) | 36 (0.947) |
| Symptoms at presentation (choice = Chills) | | | | | |
| | 0 | 49 (0.662) | 55 (0.887) | 43 (0.782) | 32 (0.842) |
| | 1 | 25 (0.338) | 7 (0.113) | 12 (0.218) | 6 (0.158) |
| Symptoms at presentation (choice = Diarrhea) | | | | | |
| | 0 | 60 (0.811) | 53 (0.855) | 39 (0.709) | 27 (0.711) |
| | 1 | 14 (0.189) | 9 (0.145) | 16 (0.291) | 11 (0.289) |
| Symptoms at presentation (choice = Sore Throat) | | | | | |
| | 0 | 73 (0.986) | 60 (0.968) | 54 (0.982) | 36 (0.947) |
| | 1 | 1 (0.014) | 2 (0.032) | 1 (0.018) | 2 (0.053) |

TABLE 13-continued

Summary of Selected Categorical Attributes for the Classes of the Hierarchical Classifier for assessment of Risk of Intubation

| | | lowest | low | intermediate | highest |
|---|---|---|---|---|---|
| | | \multicolumn{4}{c}{n (proportion of group)} | | | |
| Attribute | Category | N = 74 | N = 62 | N = 55 | N = 38 |
| Symptoms at presentation (choice = Chest pain) | | | | | |
| | 0 | 67 (0.905) | 55 (0.887) | 47 (0.855) | 37 (0.974) |
| | 1 | 7 (0.095) | 7 (0.113) | 8 (0.145) | 1 (0.026) |
| Symptoms at presentation (choice = Fatigue) | | | | | |
| | 1 | 27 (0.365) | 15 (0.242) | 17 (0.309) | 10 (0.263) |
| | 0 | 47 (0.635) | 47 (0.758) | 38 (0.691) | 28 (0.737) |
| Symptoms at presentation (choice = Headache)_1 | | | | | |
| | 1 | 4 (0.054) | 2 (0.032) | 6 (0.109) | 0 (0.000) |
| | 0 | 70 (0.946) | 60 (0.968) | 49 (0.891) | 38 (1.000) |
| Symptoms at presentation (choice = Other) | | | | | |
| | 0 | 43 (0.581) | 38 (0.613) | 34 (0.618) | 23 (0.605) |
| | 1 | 31 (0.419) | 24 (0.387) | 21 (0.382) | 15 (0.395) |
| egfr | | | | | |
| | x >= 60 | 67 (0.905) | 54 (0.871) | 46 (0.836) | 13 (0.342) |
| | 30 >= x > 60 | 3 (0.041) | 6 (0.097) | 4 (0.073) | 21 (0.553) |
| | x < 30 | 4 (0.054) | 2 (0.032) | 5 (0.091) | 4 (0.105) |

TABLE 14

Summary of Selected Numeric Attributes for the Classes of the Hierarchical Classifier for Assessment of Risk of Intubation (p values compare lowest risk group with others (low + high + highest) and highest risk group with others (lowest + low + high)

| Attribute | Class | Mean | Median | IQR | Mann-Whitney p |
|---|---|---|---|---|---|
| age | | | | | |
| | lowest | 51 | 51 | 28 | 0.004 |
| | low | 52 | 55 | 34 | |
| | intermediate | 62 | 62 | 17 | |
| | highest | 62 | 60 | 20 | 0.015 |
| ed_temperature_c | | | | | |
| | lowest | 37 | 37 | 0.90 | 0.05 |
| | low | 37 | 37 | 1.2 | |
| | intermediate | 37 | 37 | 1.3 | |
| | highest | 37 | 37 | 0.90 | 0.098 |
| ed_heart_rate | | | | | |
| | lowest | 96 | 97 | 30 | 0.154 |
| | low | 100 | 100 | 26 | |
| | intermediate | 95 | 88 | 24 | |
| | highest | 110 | 110 | 33 | 0.021 |
| ed_systolic_bp | | | | | |
| | lowest | 130 | 130 | 34 | 0.297 |
| | low | 140 | 140 | 27 | |
| | intermediate | 130 | 130 | 29 | |
| | highest | 130 | 130 | 21 | 0.431 |
| ed_diastolic_bp | | | | | |
| | lowest | 76 | 74 | 23 | 0.805 |
| | low | 75 | 74 | 14 | |
| | intermediate | 75 | 74 | 14 | |
| | highest | 74 | 74 | 20 | 0.614 |
| ed_respiratory_rate | | | | | |
| | lowest | 21 | 20 | 5.0 | 0.169 |
| | low | 21 | 20 | 6.0 | |
| | intermediate | 22 | 20 | 6.8 | |
| | highest | 25 | 24 | 12 | 0.007 |
| ed_oxygen_saturation | | | | | |
| | lowest | 92 | 93 | 5.0 | <0.001 |
| | low | 91 | 92 | 7.0 | |
| | intermediate | 91 | 92 | 6.0 | |
| | highest | 80 | 85 | 12 | <0.001 |

TABLE 14-continued

Summary of Selected Numeric Attributes for the Classes of the Hierarchical Classifier for Assessment of Risk of Intubation (p values compare lowest risk group with others (low + high + highest) and highest risk group with others (lowest + low + high)

| Attribute | Class | Mean | Median | IQR | Mann-Whitney p |
|---|---|---|---|---|---|
| weight_kg | | | | | |
| | lowest | 83 | 77 | 19 | 0.065 |
| | low | 83 | 80 | 18 | |
| | intermediate | 92 | 89 | 36 | |
| | highest | 93 | 93 | 38 | 0.102 |
| initial_qtc | | | | | |
| | lowest | 440 | 440 | 43 | 0.354 |
| | low | 440 | 440 | 30 | |
| | intermediate | 440 | 450 | 32 | |
| | highest | 450 | 440 | 47 | 0.583 |
| sodium | | | | | |
| | lowest | 140 | 140 | 4.0 | 0.319 |
| | low | 140 | 140 | 4.0 | |
| | intermediate | 140 | 140 | 4.8 | |
| | highest | 140 | 140 | 5.0 | 0.985 |
| potassium | | | | | |
| | lowest | 3.8 | 3.7 | 0.50 | 0.794 |
| | low | 3.8 | 3.8 | 0.50 | |
| | intermediate | 3.8 | 3.7 | 0.50 | |
| | highest | 4.0 | 3.8 | 0.70 | 0.082 |
| carbon_dioxide_bicarb | | | | | |
| | lowest | 24 | 24 | 3.0 | <0.001 |
| | low | 22 | 22 | 3.0 | |
| | intermediate | 23 | 23 | 2.0 | |
| | highest | 21 | 21 | 5.0 | 0.013 |
| bun | | | | | |
| | lowest | 14 | 11 | 8.0 | <0.001 |
| | low | 16 | 13 | 8.0 | |
| | intermediate | 19 | 14 | 8.3 | |
| | highest | 34 | 27 | 20 | <0.001 |
| creatinine | | | | | |
| | lowest | 0.9 | 0.79 | 0.38 | <0.001 |
| | low | 0.89 | 0.81 | 0.4 | |
| | intermediate | 1.2 | 0.99 | 0.47 | |
| | highest | 1.8 | 1.4 | 0.71 | <0.001 |
| anion_gap | | | | | |
| | lowest | 11 | 11 | 3.0 | <0.001 |
| | low | 12 | 12 | 3.0 | |
| | intermediate | 12 | 12 | 3.0 | |
| | highest | 15 | 14 | 4.0 | <0.001 |
| wbc_screen | | | | | |
| | lowest | 5.9 | 5.7 | 2.5 | <0.001 |
| | low | 9.1 | 7.3 | 3.3 | |
| | intermediate | 7.3 | 7.1 | 2.7 | |
| | highest | 11 | 9.6 | 8.0 | <0.001 |
| hemoglobin | | | | | |
| | lowest | 15 | 15 | 1.9 | 0.037 |
| | low | 14 | 14 | 2.8 | |
| | intermediate | 14 | 14 | 2.3 | |
| | highest | 15 | 15 | 2.6 | 0.244 |
| hematocrit | | | | | |
| | lowest | 44 | 44 | 5.8 | 0.07 |
| | low | 42 | 42 | 7.6 | |
| | intermediate | 42 | 43 | 5.9 | |
| | highest | 45 | 45 | 8.5 | 0.117 |
| platelet_count | | | | | |
| | lowest | 210 | 190 | 88 | 0.105 |
| | low | 240 | 230 | 91 | |
| | intermediate | 210 | 220 | 87 | |
| | highest | 210 | 180 | 160 | 0.398 |
| initial_ldh | | | | | |
| | lowest | 290 | 270 | 95 | <0.001 |
| | low | 330 | 310 | 130 | |
| | intermediate | 350 | 330 | 170 | |
| | highest | 580 | 490 | 260 | <0.001 |
| initial_d_dimer | | | | | |
| | lowest | 1100 | 580 | 520 | <0.001 |
| | low | 1100 | 780 | 950 | |
| | intermediate | 1700 | 940 | 840 | |
| | highest | 7200 | 1400 | 1900 | <0.001 |

TABLE 14-continued

Summary of Selected Numeric Attributes for the Classes of the Hierarchical Classifier for Assessment of Risk of Intubation (p values compare lowest risk group with others (low + high + highest) and highest risk group with others (lowest + low + high)

| Attribute | Class | Mean | Median | IQR | Mann-Whitney p |
|---|---|---|---|---|---|
| initial_c_reactive_protein | | | | | |
| | lowest | 43 | 41 | 47 | <0.001 |
| | low | 110 | 98 | 91 | |
| | intermediate | 110 | 110 | 99 | |
| | highest | 210 | 200 | 180 | <0.001 |
| ferritin | | | | | |
| | lowest | 460 | 340 | 370 | 0.135 |
| | low | 430 | 230 | 310 | |
| | intermediate | 740 | 520 | 830 | |
| | highest | 2300 | 640 | 830 | <0.001 |

Statistical Analysis of the Four Tests

Using the classifications presented in the previous section, Fisher's exact tests were performed comparing the proportion of outcome events in the highest and lowest risk groups to the others. Additionally, Cochran-Armitage tests for trend in the proportion of outcome events among the classification groups were performed. The results are presented in tables 15 and 16.

TABLE 15

Fisher's exact p-values comparing the proportion of outcome events in the highest risk classification group with others and lowest risk classification group with others

| | Any Complication | ICU Admission | ARDS | Intubation |
|---|---|---|---|---|
| Highest vs Rest | <1e-4 | <1e-4 | <1e-4 | <1e-4 |
| Lowest vs Rest | <1e-4 | <1e-4 | 16e-3 | 6.9e-4 |

TABLE 16

Cochran Armitage one-sided p-values testing for trend in the proportion of outcome events among the risk classification groups

| Any Complication | ICU Admission | ARDS | Intubation |
|---|---|---|---|
| <1e-4 | <1e-4 | <1e-4 | 4e-4 |

Discussion

As explained above, tests were developed to stratify patients into groups of increasing risk for each of the 4 endpoints or unfavorable outcomes occurring for hospitalized COVID-19 patients using limited clinical data. All four tests achieved highly pure (~90%) lowest risk groups and moderately pure (~50-60%) highest risk groups. The trend in increased proportion of endpoint events across the risk groups was statistically significant for all 4 tests, as was the difference in proportions between the highest and lowest risk groups vs all other groups. The performance of these tests has been validated with an independent data set, the results of which are set forth in Appendix A to our prior provisional application, Ser. No. 63/125,527 filed Dec. 15, 2020. As such, these tests could prove useful for decision making on patients admitted with COVID-19. Patients in the lowest risk group could be considered for more observation-only based treatment approaches and be candidates for early release, while patients in the highest risk groups might be candidates for more aggressive early treatment. Should hospital resources become limited, monitoring which patients are at high or low risk for severe disease as they enter the hospital could assist in scarcity triage decisions.

Across all four tests, several attributes were seemingly associated with differences in risk: ferritin, CRP, D-dimer, LDH, WBC screen, anion gap, creatine, BUN, and CO2 bicarbonate from the laboratory measurements and oxygen saturation from the ED numbers.

Further analysis via Shapley Values has been performed to further investigate the dependence of the classification algorithm on these variables on a sample-by-sample basis. Our work in Shapley Value analysis is presented in our prior provisional application, Ser. No. 63/125,527 and in the appendices B and C thereof, which are incorporated by reference. A brief summary of our work is presented here.

Shapley Values (SV)

Often, in the realm of deep learning in the medical context, we are asked what features are the most (least) important ones, and this is not an easy question to answer. Over the last couple of years an approach borrowed from economics (work pioneered by Lloyd Shapley, and the subject of a Nobel Prize) has been discussed in the realm of multivariate machine learning. Shapley values are numbers associated with each feature in the course of classification of a particular sample using a test, which tell you about the relative importance of each feature in the classification of this sample. However, the calculation of exact Shapley values is computationally prohibitively expensive for more than 20-30 features. Many approximate methods have been developed, usually requiring uncontrolled approximations.

Fortunately, the structure of the "Diagnostic Cortex" classifiers produced by the methodology of FIGS. 4 and/or 5 is such that we can estimate the Shapley values in reasonable time using Monte Carlo techniques without having to resort to these uncontrolled approximations. In the case of the tests described above, we have managed to generate SVs for 50 samples, and they give intuitively reasonable, but non-trivial results. For example, for a given patient in a risk category they tell you the ranking of used features for all the involved classifiers. Interestingly, the values can vary from classifier to classifier, and from patient to patient.

The methodology we have discovered is applicable for other tests, for example the mass spectrometry-based tests of the assignee Biodesix and described in many issued patents of the Assignee, including VeriStrat, see U.S. Pat. No. 7,736,905.

In a clinical setting, one could provide a customer with these Shapley values in addition to a test result to provide the physician (and the patient) with information how a test derived a particular test result. For example, in the case of the COVID-19 tests for a patient classified as lowest risk for ICU admission it would say (again for example) that the result of the initial binary classifier was dominated by LDH and CRP, and the result of the child classifier by ferritin, and the tree part by weight and gender. The full set of SVs for each classifier could also be presented to the physician and patient in graphical form, to show the relative importance of each attribute to the classification, as shown in Appendix B of our prior provisional application, Ser. No. 63/125,527. This information might be useful for the physician to plan future treatment and triage. For example, if a patient were classified as highest risk of poor outcome due to high levels of D-Dimer, the physician could consider therapeutic intervention to avoid blood clots, or if a patient were classified as highest risk of poor outcome due to high blood pressure, blood pressure controlling medication could be prescribed or adjusted.

As is explained in more detail in Appendix B and Appendix C of our prior provisional, Ser. No. 63/125,527, the Diagnostic Cortex classifier architecture (FIG. 5, also right hand side of FIG. 4), composed of an average over many dropout iterations each of which is a coalition of a subset of the total number of available attributes, means that an exact SV prediction for the Diagnostic Cortex algorithm trained on the same reference set using a smaller number of attributes can be obtained without the need for classifier retraining. This is explained in detail in Appendix C of our prior provisional, Ser. No. 63/125,527. However, the principle is simple: one observes that a dropout iteration that is a coalition of a subset of features, {S}, created and trained for the model using the entire set of features {M}, is also an allowable dropout iteration for any subset of {M} that includes {S}. This observation removes the need for classifier retraining and so allows the calculation of approximations to SVs using Monte Carlo-based sampling. Hence, we were able to generate SVs for the Diagnostic Cortex portions of the risk assessment classifiers. In this document when we refer to Monte Carlo methods, we are referring to any of a broad class of computational algorithms that rely on repeated random sampling to obtain numerical results. The underlying concept is to use randomness to solve problems that might be deterministic in principle. They are often used in physical and mathematical problems and are most useful when it is difficult or impossible to use other approaches. Specific examples of our methods are described in Appendix C of our prior provisional, Ser. No. 63/125,527.

The remaining parts of the risk assessment classifiers were ensemble averages of trees constructed using only a very small number of attributes. The small number of attributes allowed an exact SV calculation over the exponential number of terms in the sum, with model retraining for each attribute subset. The Shapley Value ($\Phi_j$) for a feature j can be calculated in accordance with the following equation:

$$\Phi_j = \sum_{\{S\} \subseteq \{M\}\setminus\{j\}} \frac{|S|!(|M|-|S|-1)!}{|M|!}(f(\{S\} \cup \{j\}) - f(\{S\}))$$

Where f({S}) is the result of the classifier trained using the set of features, {S}, which is a subset of all available features {M}.

SVs were evaluated for each of the classifiers used in each of the risk assessment tests for 50 patients from the validation cohort. Patients were selected so that there was somewhat equal representation across all possible test risk groups and endpoints. Race and gender were also considered in the selection, but representative populations across these attributes was secondary to risk group and endpoint. The Appendix B of our prior provisional, Ser. No. 63/125,527 provides examples of results for the calculations of the SV for particular patients with particular risk predictions.

Blinded Analysis of Closely Related Classifiers on Brown Data Set

In this section of this document, we will describe a blinded analysis of a set of classifiers which are closely related to those developed and described in detail previously. Such classifiers were then applied to an independent cohort of 128 patients hospitalized with COVID-19 at the Brown University health system. Endpoint data was initially withheld and only made available after the test labels were produced.

One difference between the Brown data set and the original classifier development set described above is that several of the attributes used to develop the original classifiers were missing either in full or for a subset of patients in the Brown set. Two approaches were used to deal with the missing attributes: imputation and redevelopment.

For the imputation approach, values for the missing attributes were predicted using the other attributes present in the data set for all missing attributes which were thought to be easily predictable from the present attributes. For a handful of attributes not thought to be easily predictable from present ones, the Diagnostic Cortex models (FIG. 4, 5) were altered so that these attributes were no longer necessary for prediction and therefore not used.

For the redevelopment approach, new classifiers were developed following an identical procedure to that used in the development of the original classifiers (FIGS. 1, 4, 5, 6 etc.) but using only the subset of attributes in the original development set which were complete in the Brown set.

All of the imputation and redevelopment was carried out using only data from the original COVID-19 classifier development set.

The completeness of available attributes in the Brown set and methodological details of both approaches are presented. The performance of both tests on each set is then presented, and conclusions are given.

Several observations and conclusion can be drawn from section of this document, and these will be explained in more detail below. While the Brown set was not complete in the attributes used to develop the original classifiers, the attributes that were present contained enough predictive information for both the imputation and redevelopment approaches to lead to decently performing tests. Performance had both similarities and differences to both what was observed in the development set for the two approaches and the performance of the original classifiers on the development set and the independent validation set, the differences will be explained later.

Another observation is that the tests of this document can be applied to make predictions for a COVID-19 patient who is presented for hospitalization even in the situation where the baseline characteristics, emergency department attributes, or lab data attributes may be incomplete or differ from the set of attributes and characteristics which were used to develop the classifiers of this disclosure. In this situation, it may be possible to impute or predict the missing attributes or characteristics from other information in the patient's electronic medical record and proceed to generate predictions. Alternatively, it may be possible to apply to such patient the classifiers, like those described above in detail, but which have been altered during development such that the missing attributes or characteristics are not necessary to make a prediction and therefore not used in classifier development. As another alternative it may be possible to apply to that patient trained classifiers (trained in accordance with the methodology of FIGS. 4, 5, 6 etc.) which only use for training the specific set of attributes which are matches for the attributes of the patient under consideration. As yet another alternative, if the patient's electronic medical record includes binary values for certain emergency department (ED) findings instead of discrete variables (such as tachycardia—Yes/No, Hypoxia—Yes/No, etc.), the classifiers could be redeveloped with binarization of the emergency department findings to match the binary characteristics of the patient's ED findings. In view of the fact that the methods of this disclosure could be applied in a diverse set of hospital environments with variation in the underlying patient electronic medical records which are used for classification and prediction of COVID-19 outcomes, in one embodiment a variety or suite of classifiers are generated using the general approach of FIGS. 1, 4, 5 and 6 etc. but taking into account these considerations. Ideally, if one were to conduct at test in this manner, one would validate the performance of such a test. In particular, one may need another set of data (or to reprocess an existing validation set with that attribute removed or binarized) to see what test performance you would expect from a particular available data scenario.

Attributes:

The original classifiers were developed on the sets of attributes given in tables 1-3, set forth previously in this document. The full cohort of Brown patients delivered contained 256 patients. After determining which attributes were thought to be imputable or acceptable to be missing for redevelopment, 128 patients that were complete in the attributes in table 17 were selected to be included in the analysis described here.

TABLE 17

Brown Set Complete Attributes

| | |
|---|---|
| Race or Ethnicity | Age |
| Sex or Gender | Sodium |
| Potassium | $CO_2$ Bicarbonate |
| BUN | Creatinine |
| eGFR | WBC Count |
| Platelet Count | CRP |

While the set of numeric Emergency Department (ED) attributes was missing entirely, a set of binary attributes derived from the same information was present and is listed in table 18. Additionally, weight was missing, but BMI was present. Ferritin, LDH, and d-Dimer were all present in the data set but were missing for a sizeable proportion of the cohort.

TABLE 18

Brown Set Binary ED Attributes

| | |
|---|---|
| Objective Fever | Hypothermia |
| Tachycardia | Hypotension |
| Tachypnea | Hypoxia |

Methods for Accounting for Missing Attributes in Brown Dataset

A. Imputation Approach

The goal of the imputation approach was to use the originally developed classifiers in prediction to the largest extent possible by imputing missing values in the data set from present ones and altering the Diagnostic Cortex models (FIG. 4, 5) to use only a portion of its component base learners to allow classification with some attributes missing entirely. This was done by only considering Diagnostic Cortex dropout iterations in the logistic regression step (FIG. 4, step 222, FIG. 5 step 121) that did not contain the attributes: hemoglobin, hematocrit, QTC.

The fundamental models we used to impute the missing features were k-nearest neighbor (kNN) regressors with a Euclidean norm trained on normalized sets constructed from the original development data.

Some attributes were imputed by directly training and applying the kNN classifiers using select attributes. Weight was imputed in this fashion using only BMI. Anion gap was imputed using sodium, potassium, and $CO_2$ Bicarbonate.

Training sets for the kNNs were taken from the original development set by taking all patients complete in the necessary attributes for the relevant kNN (e.g. for the anion gap kNNs, the training set was all patients in the original development set that were complete in sodium, potassium, and CO2 Bicarbonate. For all attributes, the kNNs used k=7. The training sets were sampled without replacement to use 80% of the available training data. This was done many (50) times to generate imputation replicates for each target sample. These replicates were then classified with all component classifiers and the plurality final risk label among the replicates after combining the component classifications was assigned as the single final risk label for each sample.

The attributes in table 19 were imputed using all complete attributes in the Brown set (table 17) and additionally, the binary ED attributes in table 18 (which were calculated in the training set using the continuous ED attributes that were present in that set). First, for each target sample, a subset of the kNN training set was selected using algorithm 1. Algorithm 1 searches the training set for patients that have the same values of the ED binaries as the test sample for imputation. It first tries to find patients that match for all six binary attributes. If it fails to find at least 25 such patients, it relaxes to search for patients that match for any five of the six attributes. The algorithm continues to relax its search in the same fashion until at least 25 matching patients are found.

The three attributes most correlated with the target attribute for imputation were then identified in the training set according to their Pearson correlation. A kNN using only the subset selected using algorithm 1 and the three identified attributes as its training set was used to impute the target attribute for the target sample.

TABLE 19

Attributes Imputed using ED Binary and Other Attributes

| | | |
|---|---|---|
| LDH | Temperature | Diastolic Blood Pressure |
| d-Dimer | Heart Rate | Respiratory Rate |
| Ferritin | Systolic Blood Pressure | Oxygen Saturation |

Algorithm 1: Selecting a subset of the kNN training set according to ED binary attributes for sample this_sample. The attribute values for a sample are represented by sample.attribute (e.g. sample.temperature). passing_samples is the set of selected training samples and is guaranteed to have more than 25 samples in it.

```
passing_samples = { }
fail_threshold = 0
WHILE number of samples in passing_samples is less than 25:
    passing samples = { }
    fail_threshold = fail_threshold + 1
    FOR train_sample in {training set}:
        nfailed = 0
        FOR attribute in {ED binary attributes}:
            IF train_sample.attribute is not equal to
this_sample.attribute:
                nfailed = nfailed + 1
            END IF
        END FOR
        IF nfailed < fail_threshold:
            append train_sample to passing_samples
        END IF
    END FOR
END WHILE
```

B. Redevelopment Approach

For the redevelopment approach, all component classifiers were redeveloped using the original development data, but with the ED attributes binarized to match those present in the Brown set. Basically, in the original development set, we had all the attributes as continuous numbers, like temperature of 38 degrees C., heart rate of 80 beats per minute, etc. In the Brown set, we only had binary attributes like fever (temperature greater than 38 degrees C.) or no fever (temperature less than or equal to 38 degrees C.). To binarize the continuous attributes in the development set for redevelopment, we determined which binary value was appropriate given the value of the continuous attribute and the thresholds (like 38 degrees for fever/no fever).

The attributes used in the Diagnostic Cortex models are given in table 20, and the attributes used in the first split decision trees are given in table 21. All hyper-parameters and hierarchical structure were identical to the original development.

TABLE 20

Redevelopment Diagnostic Cortex Attributes

| | |
|---|---|
| Sodium | $CO_2$ Bicarbonate |
| Potassium | Creatinine |
| BUN | WBC Count |
| eGFR | CRP |
| Platelet Count | |

TABLE 21

Redevelopment Decision Tree Attributes

| | | |
|---|---|---|
| Race or Ethnicity | Objective Fever | Hypothermia |
| Sex or Gender | Tachycardia | Hypotension |
| Hypoxia | Tachypnea | Age |

The Brown Data Set

The full cohort of patients delivered had a total of 256 patients. To be included for this analysis, patients had to be complete in all attributes listed in tables 17 and 18, yielding 128 patients. Selected categorical attributes are summarized in table 22, continuous attributes in table 23, and endpoint attributes in table 24.

TABLE 22

Categorical Attributes in the Brown Set (N = 128). For binary attributes, 1 indicates the presence of the condition and 0 indicates its absence.

| Attribute | Class | n (proportion of group) |
|---|---|---|
| Pt_Ethnicity | | |
| | Hispanic or Latino | 40 (0.31) |
| | Not Hispanic or Latino | 86 (0.67) |
| | Patient Refused | 2 (0.02) |
| Pt_FirstRace | | |
| | Black or African American | 22 (0.17) |
| | Other | 39 (0.30) |
| | Patient Refused | 3 (0.02) |
| | White or Caucasian | 64 (0.50) |
| Pt_Sex | | |
| | Female | 61 (0.48) |
| | Male | 67 (0.52) |
| eGFR | | |
| | 30 >= x > 60 | 33 (0.26) |
| | >60 | 83 (0.65) |
| | x < 30 | 12 (0.09) |
| hypotension | | |
| | 0 | 110 (0.86) |
| | 1 | 18 (0.14) |
| hypothermia | | |
| | 0 | 115 (0.90) |
| | 1 | 13 (0.10) |
| hypox | | |
| | 0 | 24 (0.19) |
| | 1 | 104 (0.81) |
| objective_fever | | |
| | 0 | 55 (0.43) |
| | 1 | 73 (0.57) |
| supp_o2 | | |
| | 0 | 35 (0.27) |
| | 1 | 93 (0.73) |
| tachycardia | | |
| | 0 | 61 (0.48) |
| | 1 | 67 (0.52) |
| tachypnea | | |
| | 0 | 35 (0.27) |
| | 1 | 93 (0.73) |

TABLE 23

Continuous Attributes in the Brown Set

| Attribute | nMissing | Median | 25th Percentile | 75th Percentile |
|---|---|---|---|---|
| BMI_Value_N | 0 | 30 | 27 | 34 |
| BUN | 0 | 16 | 11 | 27 |
| CO2 | 0 | 24 | 22 | 26 |
| CRP | 0 | 99 | 37 | 180 |
| Calcium | 0 | 8.8 | 8.4 | 9.2 |
| Creatinine | 0 | 0.94 | 0.77 | 1.3 |
| DDimer_Level | 87 | 340 | 220 | 630 |
| Ferritin | 43 | 570 | 280 | 1100 |
| LDH | 26 | 290 | 220 | 370 |
| Platelets | 0 | 200 | 150 | 250 |
| Potassium | 0 | 3.7 | 3.5 | 4.2 |
| Pt_Age_AtIndex | 0 | 61 | 51 | 71 |

TABLE 23-continued

Continuous Attributes in the Brown Set

| Attribute | nMissing | Median | 25th Percentile | 75th Percentile |
|---|---|---|---|---|
| WBC | 0 | 6.6 | 4.9 | 8.9 |
| sodium | 0 | 140 | 130 | 140 |

TABLE 24

Endpoint Attributes in the Brown Set (N = 128)

| Attribute | Class | n (proportion of group) |
|---|---|---|
| discharge | | |
| | Alive | 114 (0.89) |
| | Deceased | 14 (0.11) |
| icu | | |
| | Not admitted | 99 (0.77) |
| | Admitted | 29 (0.23) |
| mech_vent_need | | |
| | Not needed | 113 (0.88) |
| | Needed | 15 (0.12) |

Results

Tests Predicting Risk of Admission to the ICU

In the Brown set, the redevelopment approach test predicting risk of admission to the ICU classified 44 (34%) patients to the Highest risk group, 33 (26%) to the High risk group, 30 (23%) to the Low risk group, and 21 (16%) to the Lowest risk group. In the development set, the test classified 49 (21%) patients to the Highest risk group, 54 (24%) to the High risk group, 65 (28%) to the Low risk group, 61 (27%) to the Lowest risk group.

In the Brown set, the imputation approach test predicting risk of admission to the ICU classified 43 (34%) patients to the Highest risk group, 26 (20%) to the High risk group, 45 (35%) to the Low risk group, and 14 (11%) to the Lowest risk group. In the development set, the test classified 38 (19%) patients to the Highest risk group, 67 (33%) to the High risk group, 77 (38%) to the Low risk group, 23 (11%) to the Lowest risk group.

Table 25 compares the final risk group proportions, precision, and recall for the redevelopment approach for predicting risk of ICU admission in both the development and Brown cohorts. Table 26 gives the same results for the imputation approach.

TABLE 25

Comparison of Final Risk Group Proportions, Precision (PPV/NPV), and Recall for the Redevelopment Approach. Positive indicates admission to the ICU.

| Test | Risk Group | N Positive (proportion) | N Negative (proportion) | Precision | Recall |
|---|---|---|---|---|---|
| Development | Highest | 30 (61%) | 19 (39%) | 0.61 | 0.39 |
| Brown | Highest | 16 (36%) | 28 (64%) | 0.36 | 0.55 |
| Development | High | 15 (28%) | 39 (72%) | 0.28 | 0.19 |
| Brown | High | 7 (21%) | 26 (79%) | 0.21 | 0.24 |
| Development | Low | 17 (26%) | 48 (74%) | 0.74 | 0.32 |
| Brown | Low | 5 (17%) | 25 (83%) | 0.83 | 0.25 |
| Development | Lowest | 15 (25%) | 46 (75%) | 0.75 | 0.30 |
| Brown | Lowest | 1 (5%) | 20 (95%) | 0.95 | 0.20 |

TABLE 26

Comparison of Final Risk Group Proportions, Precision (PPV/NPV), and Recall for the Imputation Approach. Positive indicates admission to the ICU.

| Test | Risk Group | N Positive (proportion) | N Negative (proportion) | Precision | Recall |
|---|---|---|---|---|---|
| Development | Highest | 28 (74%) | 10 (26%) | 0.74 | 0.36 |
| Brown | Highest | 15 (35%) | 28 (65%) | 0.35 | 0.52 |
| Development | High | 23 (34%) | 44 (66%) | 0.34 | 0.30 |
| Brown | High | 5 (19%) | 21 (81%) | 0.19 | 0.17 |
| Development | Low | 23 (30%) | 54 (70%) | 0.70 | 0.42 |
| Brown | Low | 8 (18%) | 37 (82%) | 0.82 | 0.37 |
| Development | Lowest | 3 (13%) | 20 (87%) | 0.87 | 0.16 |
| Brown | Lowest | 1 (7%) | 13 (93%) | 0.93 | 0.13 |

Imputation

Tables 27 and 28, respectively, summarize selected categorical and continuous attributes by risk label. Mann-Whitney p-values are given comparing the median continuous attribute between the highest and lowest risk groups compared to all other risk groups. All statistics in these tables were calculated using Matlab R2020b.

TABLE 27

Categorical Attributes by Risk Label

| Attribute | Class | Lowest (N = 14) n (proportion of group) | Low (N = 45) n (proportion of group) | High (N = 26) n (proportion of group) | Highest (N = 43) n (proportion of group) |
|---|---|---|---|---|---|
| Pt_Ethnicity | | | | | |
| | Hispanic or Latino | 2 (0.14) | 19 (0.42) | 5 (0.19) | 14 (0.33) |
| | Not Hispanic or Latino | 11 (0.79) | 25 (0.56) | 21 (0.81) | 29 (0.67) |
| | Patient Refused | 1 (0.07) | 1 (0.02) | 0 (0.00) | 0 (0.00) |
| Pt_FirstRace | | | | | |
| | Black or African American | 3 (0.21) | 7 (0.16) | 2 (0.08) | 10 (0.23) |
| | Other | 2 (0.14) | 17 (0.38) | 6 (0.23) | 14 (0.33) |
| | Patient Refused | 1 (0.07) | 2 (0.04) | 0 (0.00) | 0 (0.00) |
| | White or Caucasian | 8 (0.57) | 19 (0.42) | 18 (0.69) | 19 (0.44) |
| Pt_Sex | | | | | |
| | Female | 10 (0.71) | 26 (0.58) | 10 (0.38) | 15 (0.35) |
| | Male | 4 (0.29) | 19 (0.42) | 16 (0.62) | 28 (0.65) |
| eGFR | | | | | |
| | 30 >= x > 60 | 4 (0.29) | 7 (0.16) | 5 (0.19) | 17 (0.40) |
| | >60 | 10 (0.71) | 35 (0.78) | 20 (0.77) | 18 (0.42) |
| | x < 30 | 0 (0.00) | 3 (0.07) | 1 (0.04) | 8 (0.19) |
| hypotension | | | | | |
| | 0 | 13 (0.93) | 40 (0.89) | 23 (0.88) | 34 (0.79) |
| | 1 | 1 (0.07) | 5 (0.11) | 3 (0.12) | 9 (0.21) |
| hypothermia | | | | | |
| | 0 | 14 (1.00) | 38 (0.84) | 24 (0.92) | 39 (0.91) |
| | 1 | 0 (0.00) | 7 (0.16) | 2 (0.08) | 4 (0.09) |
| Hypox | | | | | |
| | 0 | 9 (0.64) | 7 (0.16) | 4 (0.15) | 4 (0.09) |
| | 1 | 5 (0.36) | 38 (0.84) | 22 (0.85) | 39 (0.91) |
| objective_fever | | | | | |
| | 0 | 10 (0.71) | 19 (0.42) | 9 (0.35) | 17 (0.40) |
| | 1 | 4 (0.29) | 26 (0.58) | 17 (0.65) | 26 (0.60) |
| supp_o2 | | | | | |
| | 0 | 10 (0.71) | 12 (0.27) | 6 (0.23) | 7 (0.16) |
| | 1 | 4 (0.29) | 33 (0.73) | 20 (0.77) | 36 (0.84) |
| tachycardia | | | | | |
| | 0 | 11 (0.79) | 25 (0.56) | 14 (0.54) | 11 (0.26) |
| | 1 | 3 (0.21) | 20 (0.44) | 12 (0.46) | 32 (0.74) |
| tachypnea | | | | | |
| | 0 | 11 (0.79) | 12 (0.27) | 10 (0.38) | 2 (0.05) |
| | 1 | 3 (0.21) | 33 (0.73) | 16 (0.62) | 41 (0.95) |

TABLE 28

Continuous Attributes by Risk Label

| Attribute | Label | nMissing | Median | 25th Percentile | 75th Percentile | Mann-Whitney p |
|---|---|---|---|---|---|---|
| BMI_Value_N | Lowest | 0 | 32 | 28 | 33 | 0.899 |
| | Low | 0 | 30 | 28 | 36 | |
| | High | 0 | 28 | 26 | 32 | |
| | Highest | 0 | 31 | 27 | 35 | 0.690 |
| BUN | Lowest | 0 | 13 | 11 | 20 | 0.327 |
| | Low | 0 | 13 | 10 | 17 | |
| | High | 0 | 17 | 11 | 24 | |
| | Highest | 0 | 28 | 13 | 52 | <0.001 |

TABLE 28-continued

Continuous Attributes by Risk Label

| Attribute | Label | nMissing | Median | 25th Percentile | 75th Percentile | Mann-Whitney p |
|---|---|---|---|---|---|---|
| $CO_2$ | Lowest | 0 | 25 | 24 | 26 | 0.193 |
| | Low | 0 | 25 | 23 | 26 | |
| | High | 0 | 25 | 24 | 26 | |
| | Highest | 0 | 24 | 20 | 25 | 0.004 |
| CRP | Lowest | 0 | 15 | 5.6 | 42 | <0.001 |
| | Low | 0 | 51 | 27 | 180 | |
| | High | 0 | 100 | 77 | 140 | |
| | Highest | 0 | 140 | 98 | 260 | <0.001 |
| Calcium | Lowest | 0 | 9.4 | 8.7 | 9.6 | 0.011 |
| | Low | 0 | 8.7 | 8.5 | 9.1 | |
| | High | 0 | 8.8 | 8.5 | 9 | |
| | Highest | 0 | 8.8 | 8.4 | 9.2 | 0.498 |
| Creatinine | Lowest | 0 | 0.9 | 0.72 | 1.3 | 0.630 |
| | Low | 0 | 0.8 | 0.67 | 1.1 | |
| | High | 0 | 0.9 | 0.76 | 1 | |
| | Highest | 0 | 1.1 | 0.9 | 1.6 | <0.001 |
| DDimer_Level | Lowest | 11 | 330 | 120 | 530 | 0.568 |
| | Low | 29 | 290 | 210 | 360 | |
| | High | 17 | 350 | 270 | 1400 | |
| | Highest | 30 | 490 | 350 | 670 | 0.095 |
| Ferritin | Lowest | 8 | 100 | 22 | 200 | 0.002 |
| | Low | 17 | 680 | 360 | 1000 | |
| | High | 9 | 410 | 240 | 1000 | |
| | Highest | 9 | 800 | 500 | 1500 | 0.012 |
| LDH | Lowest | 2 | 170 | 150 | 240 | <0.001 |
| | Low | 9 | 300 | 230 | 350 | |
| | High | 4 | 280 | 240 | 370 | |
| | Highest | 11 | 350 | 240 | 440 | 0.019 |
| Platelets | Lowest | 0 | 190 | 160 | 270 | 0.538 |
| | Low | 0 | 220 | 160 | 240 | |
| | High | 0 | 180 | 160 | 220 | |
| | Highest | 0 | 170 | 130 | 270 | 0.486 |
| Potassium | Lowest | 0 | 3.9 | 3.5 | 4.3 | 0.459 |
| | Low | 0 | 3.6 | 3.4 | 3.8 | |
| | High | 0 | 3.7 | 3.4 | 3.9 | |
| | Highest | 0 | 4 | 3.5 | 4.4 | 0.011 |
| Pt_Age_AtIndex | Lowest | 0 | 59 | 45 | 71 | 0.633 |
| | Low | 0 | 59 | 50 | 65 | |
| | High | 0 | 68 | 57 | 83 | |
| | Highest | 0 | 62 | 50 | 71 | 0.765 |
| WBC | Lowest | 0 | 6 | 4.9 | 6.8 | 0.287 |
| | Low | 0 | 6.1 | 4.8 | 8.1 | |
| | High | 0 | 6.8 | 5.4 | 8.8 | |
| | Highest | 0 | 7.6 | 4.9 | 10 | 0.059 |
| sodium | Lowest | 0 | 130 | 130 | 140 | 0.439 |
| | Low | 0 | 140 | 130 | 140 | |
| | High | 0 | 140 | 130 | 140 | |
| | Highest | 0 | 140 | 130 | 140 | 0.214 |

Redevelopment

Figure 24:
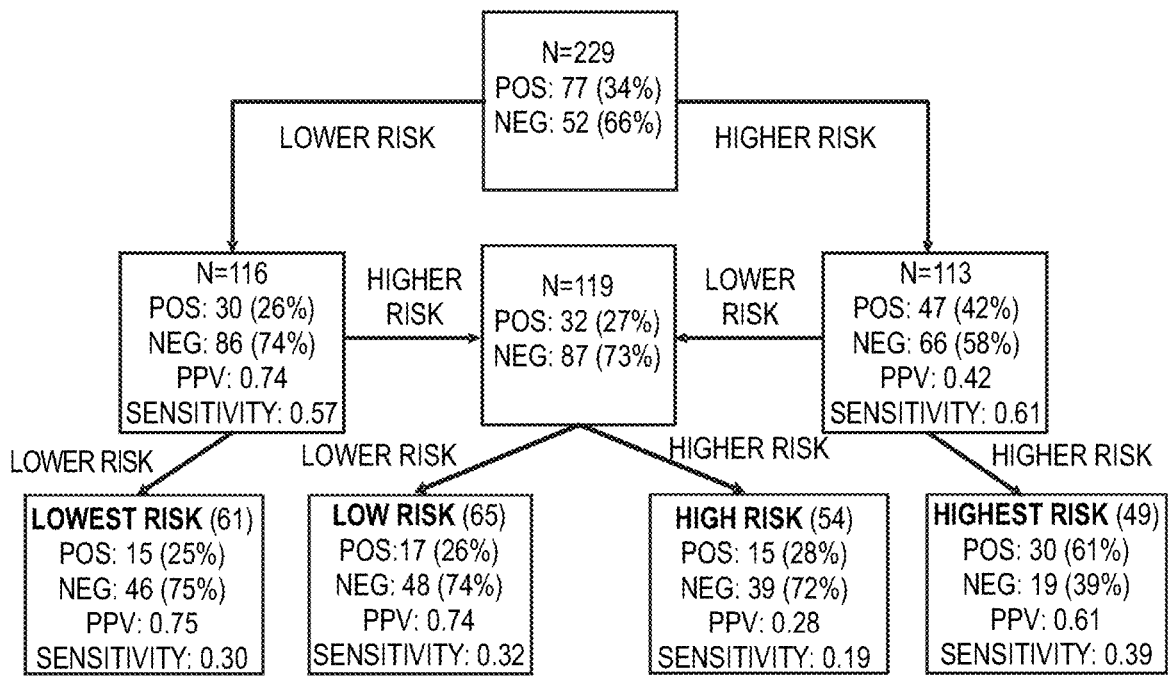
FIG. 24 is a chart showing the performance of a redeveloped ICU admission test on the development set. The redeveloped ICU admission test used what is referred to below as a "redevelopment approach" in which all component classifiers were redeveloped using the original development data, but the emergency department (ED) attributes were binarized in order to match the binarization of ED attributes as presented in the Brown set.
Figure 25:
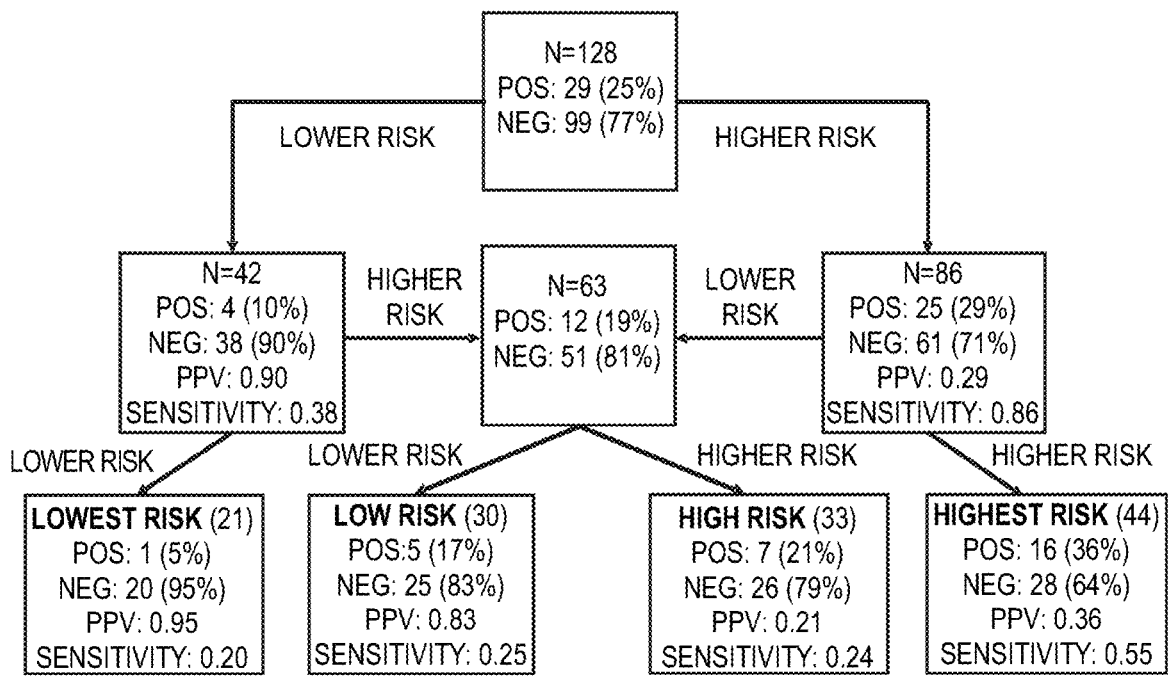
FIG. 25 is a chart showing the performance of redeveloped ICU test on a Brown data set.

FIG. 24 shows the proportion of patients admitted to the ICU (positive), the proportion not admitted to the ICU (negative), precision, and recall in each relevant group for the ICU admission hierarchical test in the development set. FIG. 25 gives the corresponding results in the Brown set. These figures show results for the redeveloped ICU admission classifier using the "redevelopment approach" described earlier, i.e., with ED attributes in the development set binarized.

Tables 29 and 30, respectively, summarize selected categorical and continuous attributes by risk label. Mann-Whitney p-values are given comparing the median continuous attribute between the highest and lowest risk groups compared to all other risk groups. All statistics in these tables were calculated using Matlab R2020b.

TABLE 29

Categorical Attributes by Risk Label

| Attribute | Class | Lowest (N = 21) n (proportion of group) | Low (N = 30) n (proportion of group) | High (N = 33) n (proportion of group) | Highest (N = 44) n (proportion of group) |
|---|---|---|---|---|---|
| Pt_Ethnicity | | | | | |
| | Hispanic or Latino | 3 (0.14) | 14 (0.47) | 9 (0.27) | 14 (0.32) |
| | Not Hispanic or Latino | 17 (0.81) | 15 (0.50) | 24 (0.73) | 30 (0.68) |
| | Patient Refused | 1 (0.05) | 1 (0.03) | 0 (0.00) | 0 (0.00) |
| Pt_FirstRace | | | | | |
| | Black or African American | 4 (0.19) | 4 (0.13) | 3 (0.09) | 11 (0.25) |
| | Other | 3 (0.14) | 15 (0.50) | 7 (0.21) | 14 (0.32) |
| | Patient Refused | 1 (0.05) | 2 (0.07) | 0 (0.00) | 0 (0.00) |
| | White or Caucasian | 13 (0.62) | 9 (0.30) | 23 (0.70) | 19 (0.43) |
| Pt_Sex | | | | | |
| | Female | 16 (0.76) | 17 (0.57) | 14 (0.42) | 14 (0.32) |
| | Male | 5 (0.24) | 13 (0.43) | 19 (0.58) | 30 (0.68) |
| eGFR | | | | | |
| | 30 >= x > 60 | 5 (0.24) | 4 (0.13) | 7 (0.21) | 17 (0.39) |
| | >60 | 16 (0.76) | 24 (0.80) | 26 (0.79) | 17 (0.39) |
| | x < 30 | 0 (0.00) | 2 (0.07) | 0 (0.00) | 10 (0.23) |
| hypotension | | | | | |
| | 0 | 20 (0.95) | 26 (0.87) | 29 (0.88) | 35 (0.80) |
| | 1 | 1 (0.05) | 4 (0.13) | 4 (0.12) | 9 (0.20) |
| hypothermia | | | | | |
| | 0 | 18 (0.86) | 29 (0.97) | 28 (0.85) | 40 (0.91) |
| | 1 | 3 (0.14) | 1 (0.03) | 5 (0.15) | 4 (0.09) |
| Hypox | | | | | |
| | 0 | 9 (0.43) | 5 (0.17) | 5 (0.15) | 5 (0.11) |
| | 1 | 12 (0.57) | 25 (0.83) | 28 (0.85) | 39 (0.89) |
| objective_fever | | | | | |
| | 0 | 16 (0.76) | 6 (0.20) | 16 (0.48) | 17 (0.39) |
| | 1 | 5 (0.24) | 24 (0.80) | 17 (0.52) | 27 (0.61) |
| supp_o2 | | | | | |
| | 0 | 11 (0.52) | 9 (0.30) | 8 (0.24) | 7 (0.16) |
| | 1 | 10 (0.48) | 21 (0.70) | 25 (0.76) | 37 (0.84) |
| tachycardia | | | | | |
| | 0 | 13 (0.62) | 15 (0.50) | 18 (0.55) | 15 (0.34) |
| | 1 | 8 (0.38) | 15 (0.50) | 15 (0.45) | 29 (0.66) |
| tachypnea | | | | | |
| | 0 | 12 (0.57) | 6 (0.20) | 13 (0.39) | 4 (0.09) |
| | 1 | 9 (0.43) | 24 (0.80) | 20 (0.61) | 40 (0.91) |

TABLE 30

Continuous Attributes by Risk Label

| Attribute | Label | nMissing | Median | 25th Percentile | 75th Percentile | Mann-Whitney p |
|---|---|---|---|---|---|---|
| BMI_Value_N | Lowest | 0 | 32 | 29 | 38 | 0.069 |
| | Low | 0 | 31 | 28 | 34 | |
| | High | 0 | 30 | 27 | 34 | |
| | Highest | 0 | 28 | 25 | 33 | 0.025 |
| BUN | Lowest | 0 | 13 | 11 | 21 | 0.138 |
| | Low | 0 | 12 | 9 | 16 | |
| | High | 0 | 15 | 10 | 20 | |
| | Highest | 0 | 29 | 19 | 51 | <0.001 |
| CO2 | Lowest | 0 | 25 | 25 | 26 | 0.057 |
| | Low | 0 | 23 | 22 | 25 | |
| | High | 0 | 25 | 24 | 26 | |
| | Highest | 0 | 24 | 20 | 26 | 0.118 |

TABLE 30-continued

Continuous Attributes by Risk Label

| Attribute | Label | nMissing | Median | 25th Percentile | 75th Percentile | Mann-Whitney p |
|---|---|---|---|---|---|---|
| CRP | Lowest | 0 | 36 | 9.6 | 66 | <0.001 |
| | Low | 0 | 38 | 24 | 110 | |
| | High | 0 | 130 | 99 | 190 | |
| | Highest | 0 | 140 | 91 | 260 | <0.001 |
| Calcium | Lowest | 0 | 9 | 8.7 | 9.4 | 0.033 |
| | Low | 0 | 8.7 | 8.5 | 8.8 | |
| | High | 0 | 8.8 | 8.4 | 9.1 | |
| | Highest | 0 | 8.7 | 8.3 | 9.2 | 0.615 |
| Creatinine | Lowest | 0 | 0.83 | 0.65 | 1.2 | 0.073 |
| | Low | 0 | 0.91 | 0.73 | 1 | |
| | High | 0 | 0.84 | 0.69 | 0.99 | |
| | Highest | 0 | 1.3 | 0.9 | 1.9 | <0.001 |
| DDimer_Level | Lowest | 17 | 120 | 120 | 430 | 0.140 |
| | Low | 22 | 290 | 210 | 320 | |
| | High | 20 | 290 | 200 | 720 | |
| | Highest | 28 | 420 | 370 | 640 | 0.029 |
| Ferritin | Lowest | 8 | 330 | 110 | 430 | <0.001 |
| | Low | 14 | 860 | 420 | 1400 | |
| | High | 11 | 440 | 260 | 740 | |
| | Highest | 10 | 840 | 470 | 2400 | 0.007 |
| LDH | Lowest | 3 | 240 | 160 | 320 | 0.008 |
| | Low | 5 | 270 | 230 | 360 | |
| | High | 7 | 320 | 240 | 370 | |
| | Highest | 11 | 330 | 230 | 440 | 0.138 |
| Platelets | Lowest | 0 | 220 | 170 | 280 | 0.053 |
| | Low | 0 | 210 | 170 | 240 | |
| | High | 0 | 180 | 160 | 220 | |
| | Highest | 0 | 170 | 120 | 260 | 0.199 |
| Potassium | Lowest | 0 | 3.7 | 3.5 | 4.5 | 0.862 |
| | Low | 0 | 3.5 | 3.4 | 3.8 | |
| | High | 0 | 3.8 | 3.7 | 4 | |
| | Highest | 0 | 3.9 | 3.5 | 4.4 | 0.035 |
| Pt_Age_AtIndex | Lowest | 0 | 61 | 55 | 73 | 0.731 |
| | Low | 0 | 56 | 43 | 61 | |
| | High | 0 | 60 | 54 | 72 | |
| | Highest | 0 | 65 | 56 | 74 | 0.033 |
| WBC | Lowest | 0 | 6.2 | 4.9 | 7.6 | 0.573 |
| | Low | 0 | 6.3 | 3.8 | 7.7 | |
| | High | 0 | 6.2 | 4.8 | 7.9 | |
| | Highest | 0 | 8.4 | 5.2 | 11 | 0.009 |
| sodium | Lowest | 0 | 130 | 130 | 140 | 0.144 |
| | Low | 0 | 130 | 130 | 140 | |
| | High | 0 | 140 | 130 | 140 | |
| | Highest | 0 | 140 | 130 | 140 | 0.165 |

Tests Predicting Risk of Intubation

In the Brown set, the redevelopment approach test predicting risk of intubation classified 24 (19%) patients to the Highest risk group, 35 (27%) to the High risk group, 40 (31%) to the Low risk group, and 29 (23%) to the Lowest risk group. In the development set, the test classified 42 (18%) patients to the Highest risk group, 61 (27%) to the High risk group, 58 (25%) to the Low risk group, 68 (30%) to the Lowest risk group.

In the Brown set, the imputation approach test predicting risk of intubation classified 27 (21%) patients to the Highest risk group, 20 (16%) to the High risk group, 37 (29%) to the Low risk group, and 44 (34%) to the Lowest risk group. In the development set, the test classified 33 (16%) patients to the Highest risk group, 51 (25%) to the High risk group, 50 (24%) to the Low risk group, 71 (35%) to the Lowest risk group.

Table 31 compares the final risk group proportions, precision, and recall for the redevelopment approach for predicting risk of intubation in both the development and Brown cohorts. Table 32 gives the same results for the imputation approach.

TABLE 31

Comparison of Final Risk Group Proportions, Precision (PPV/NPV), and Recall for the Redevelopment Approach. Positive indicates the need for intubation.

| Test | Risk Group | N Positive (proportion) | N Negative (proportion) | Precision | Recall |
|---|---|---|---|---|---|
| Development | Highest | 22 (52%) | 20 (48%) | 0.52 | 0.42 |
| Brown | Highest | 6 (25%) | 18 (75%) | 0.25 | 0.40 |
| Development | High | 13 (21%) | 48 (79%) | 0.21 | 0.25 |
| Brown | High | 6 (17%) | 29 (83%) | 0.17 | 0.40 |
| Development | Low | 10 (17%) | 48 (83%) | 0.83 | 0.27 |

TABLE 31-continued

Comparison of Final Risk Group Proportions, Precision (PPV/NPV), and Recall for the Redevelopment Approach. Positive indicates the need for intubation.

| Test | Risk Group | N Positive (proportion) | N Negative (proportion) | Precision | Recall |
|---|---|---|---|---|---|
| Brown | Low | 3 (8%) | 37 (92%) | 0.92 | 0.33 |
| Development | Lowest | 8 (12%) | 60 (88%) | 0.88 | 0.34 |
| Brown | Lowest | 0 (0%) | 29 (100%) | 1.00 | 0.26 |

TABLE 32

Comparison of Final Risk Group Proportions, Precision (PPV/NPV), and Recall for the Imputation Approach. Positive indicates the need for intubation.

| Test | Risk Group | N Positive (proportion) | N Negative (proportion) | Precision | Recall |
|---|---|---|---|---|---|
| Development | Highest | 26 (79%) | 7 (21%) | 0.79 | 0.49 |
| Brown | Highest | 7 (26%) | 20 (74%) | 0.26 | 0.47 |
| Development | High | 7 (14%) | 44 (86%) | 0.14 | 0.13 |
| Brown | High | 2 (10%) | 18 (90%) | 0.10 | 0.13 |
| Development | Low | 12 (24%) | 38 (76%) | 0.76 | 0.25 |
| Brown | Low | 5 (14%) | 32 (86%) | 0.86 | 0.28 |
| Development | Lowest | 8 (11%) | 63 (89%) | 0.89 | 0.41 |
| Brown | Lowest | 1 (2%) | 43 (98%) | 0.98 | 0.38 |

Imputation

Tables 33 and 34, respectively, summarize selected categorical and continuous attributes by risk label. Mann-Whitney p-values are given comparing the median continuous attribute between the highest and lowest risk groups compared to all other risk groups. All statistics in these tables were calculated using Matlab R2020b.

TABLE 33

| | | Categorical Attributes by Risk Label | | | |
|---|---|---|---|---|---|
| Attribute | Class | Lowest (N = 44) n (proportion of group) | Low (N = 37) n (proportion of group) | High (N = 20) n (proportion of group) | Highest (N = 27) n (proportion of group) |
| Pt_Ethnicity | | | | | |
| | Hispanic or Latino | 12 (0.27) | 8 (0.22) | 11 (0.55) | 9 (0.33) |
| | Not Hispanic or Latino | 30 (0.68) | 29 (0.78) | 9 (0.45) | 18 (0.67) |
| | Patient Refused | 2 (0.04) | 0 (0.00) | 0 (0.00) | 0 (0.00) |
| Pt_FirstRace | | | | | |
| | Black or African American | 7 (0.16) | 1 (0.03) | 6 (0.30) | 8 (0.30) |
| | Other | 12 (0.27) | 9 (0.24) | 10 (0.50) | 8 (0.30) |
| | Patient Refused | 3 (0.07) | 0 (0.00) | 0 (0.00) | 0 (0.00) |
| | White or Caucasian | 22 (0.50) | 27 (0.73) | 4 (0.20) | 11 (0.41) |
| Pt_Sex | | | | | |
| | Female | 28 (0.64) | 15 (0.41) | 9 (0.45) | 9 (0.33) |
| | Male | 16 (0.36) | 22 (0.59) | 11 (0.55) | 18 (0.67) |
| eGFR | | | | | |
| | 30 >= x > 60 | 10 (0.23) | 8 (0.22) | 2 (0.10) | 13 (0.48) |
| | >60 | 33 (0.75) | 26 (0.70) | 17 (0.85) | 7 (0.26) |
| | x < 30 | 1 (0.02) | 3 (0.08) | 1 (0.05) | 7 (0.26) |
| hypotension | | | | | |
| | 0 | 39 (0.89) | 33 (0.89) | 18 (0.90) | 20 (0.74) |
| | 1 | 5 (0.11) | 4 (0.11) | 2 (0.10) | 7 (0.26) |
| hypothermia | | | | | |
| | 0 | 42 (0.95) | 32 (0.86) | 17 (0.85) | 24 (0.89) |
| | 1 | 2 (0.04) | 5 (0.14) | 3 (0.15) | 3 (0.11) |

TABLE 33-continued

| | | Categorical Attributes by Risk Label | | | |
|---|---|---|---|---|---|
| | | Lowest (N = 44) | Low (N = 37) | High (N = 20) | Highest (N = 27) |
| Attribute | Class | n (proportion of group) | n (proportion of group) | n (proportion of group) | n (proportion of group) |
| Hypox | | | | | |
| | 0 | 13 (0.30) | 2 (0.05) | 5 (0.25) | 4 (0.15) |
| | 1 | 31 (0.70) | 35 (0.95) | 15 (0.75) | 23 (0.85) |
| objective_fever | | | | | |
| | 0 | 21 (0.48) | 16 (0.43) | 6 (0.30) | 12 (0.44) |
| | 1 | 23 (0.52) | 21 (0.57) | 14 (0.70) | 15 (0.56) |
| supp_o2 | | | | | |
| | 0 | 19 (0.43) | 6 (0.16) | 5 (0.25) | 5 (0.19) |
| | 1 | 25 (0.57) | 31 (0.84) | 15 (0.75) | 22 (0.81) |
| tachycardia | | | | | |
| | 0 | 26 (0.59) | 15 (0.41) | 11 (0.55) | 9 (0.33) |
| | 1 | 18 (0.41) | 22 (0.59) | 9 (0.45) | 18 (0.67) |
| tachypnea | | | | | |
| | 0 | 20 (0.45) | 9 (0.24) | 4 (0.20) | 2 (0.07) |
| | 1 | 24 (0.55) | 28 (0.76) | 16 (0.80) | 25 (0.93) |

TABLE 34

| | Continuous Attributes by Risk Label | | | | | |
|---|---|---|---|---|---|---|
| Attribute | Label | nMissing | Median | 25th Percentile | 75th Percentile | Mann-Whitney p |
| BMI_Value_N | Lowest | 0 | 31 | 26 | 33 | 0.825 |
| | Low | 0 | 28 | 27 | 30 | |
| | High | 0 | 34 | 30 | 39 | |
| | Highest | 0 | 31 | 27 | 35 | 0.764 |
| BUN | Lowest | 0 | 13 | 10 | 20 | 0.016 |
| | Low | 0 | 15 | 11 | 26 | |
| | High | 0 | 12 | 10 | 16 | |
| | Highest | 0 | 46 | 25 | 62 | <0.001 |
| CO2 | Lowest | 0 | 25 | 23 | 26 | 0.205 |
| | Low | 0 | 24 | 23 | 26 | |
| | High | 0 | 25 | 22 | 28 | |
| | Highest | 0 | 24 | 19 | 25 | 0.038 |
| CRP | Lowest | 0 | 30 | 17 | 52 | <0.001 |
| | Low | 0 | 140 | 110 | 190 | |
| | High | 0 | 160 | 56 | 190 | |
| | Highest | 0 | 200 | 98 | 290 | <0.001 |
| Calcium | Lowest | 0 | 8.8 | 8.6 | 9.4 | 0.188 |
| | Low | 0 | 8.8 | 8.3 | 9.1 | |
| | High | 0 | 8.7 | 8.5 | 9.2 | |
| | Highest | 0 | 8.9 | 8.5 | 9.2 | 0.837 |
| Creatinine | Lowest | 0 | 0.88 | 0.68 | 1.1 | 0.025 |
| | Low | 0 | 0.93 | 0.69 | 1.1 | |
| | High | 0 | 0.85 | 0.75 | 0.96 | |
| | Highest | 0 | 1.5 | 1.1 | 2.1 | <0.001 |
| DDimer_Level | Lowest | 32 | 210 | 160 | 340 | 0.016 |
| | Low | 22 | 320 | 250 | 420 | |
| | High | 17 | 4500 | 2400 | 6700 | |
| | Highest | 16 | 490 | 380 | 650 | 0.084 |
| Ferritin | Lowest | 18 | 310 | 95 | 520 | <0.001 |
| | Low | 9 | 500 | 370 | 860 | |
| | High | 12 | 840 | 580 | 860 | |
| | Highest | 4 | 1100 | 760 | 2400 | <0.001 |
| LDH | Lowest | 8 | 250 | 190 | 330 | 0.001 |
| | Low | 9 | 300 | 230 | 350 | |
| | High | 4 | 340 | 270 | 400 | |
| | Highest | 5 | 360 | 280 | 510 | 0.004 |
| Platelets | Lowest | 0 | 180 | 130 | 240 | 0.193 |
| | Low | 0 | 200 | 160 | 240 | |
| | High | 0 | 210 | 170 | 260 | |
| | Highest | 0 | 200 | 150 | 300 | 0.587 |

TABLE 34-continued

Continuous Attributes by Risk Label

| Attribute | Label | nMissing | Median | 25th Percentile | 75th Percentile | Mann-Whitney p |
|---|---|---|---|---|---|---|
| Potassium | Lowest | 0 | 3.8 | 3.5 | 4.1 | 0.805 |
| | Low | 0 | 3.7 | 3.4 | 3.9 | |
| | High | 0 | 3.5 | 3.4 | 3.7 | |
| | Highest | 0 | 4.2 | 3.6 | 4.5 | 0.003 |
| Pt_Age_AtIndex | Lowest | 0 | 60 | 47 | 68 | 0.246 |
| | Low | 0 | 58 | 44 | 78 | |
| | High | 0 | 60 | 55 | 62 | |
| | Highest | 0 | 67 | 62 | 74 | 0.004 |
| WBC | Lowest | 0 | 5.2 | 3.6 | 6.7 | <0.001 |
| | Low | 0 | 6.8 | 5 | 8.3 | |
| | High | 0 | 7.5 | 5.9 | 9.5 | |
| | Highest | 0 | 8.9 | 6.5 | 11 | 0.001 |
| sodium | Lowest | 0 | 130 | 130 | 140 | 0.415 |
| | Low | 0 | 140 | 130 | 140 | |
| | High | 0 | 130 | 130 | 140 | |
| | Highest | 0 | 140 | 130 | 140 | 0.069 |

Redevelopment

Figure 26:
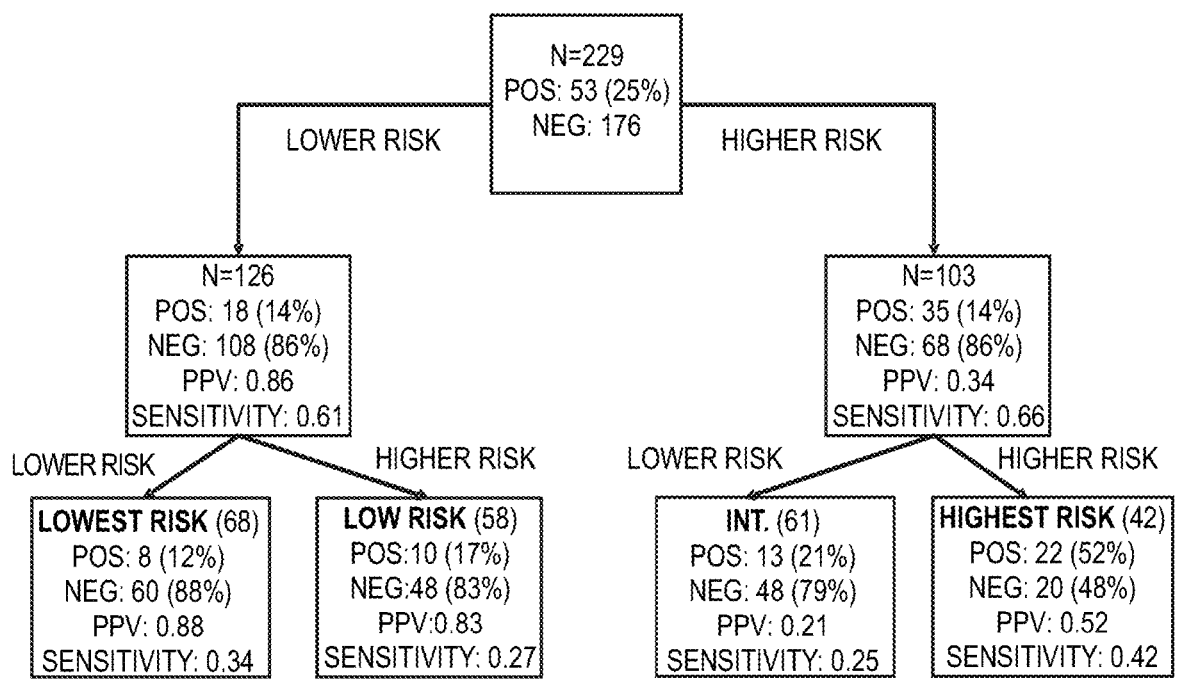
FIG. 26 is a chart showing the performance of a redeveloped Intubation test on the development set, again using redeveloped classifiers using the "redevelopment approach."
Figure 27:
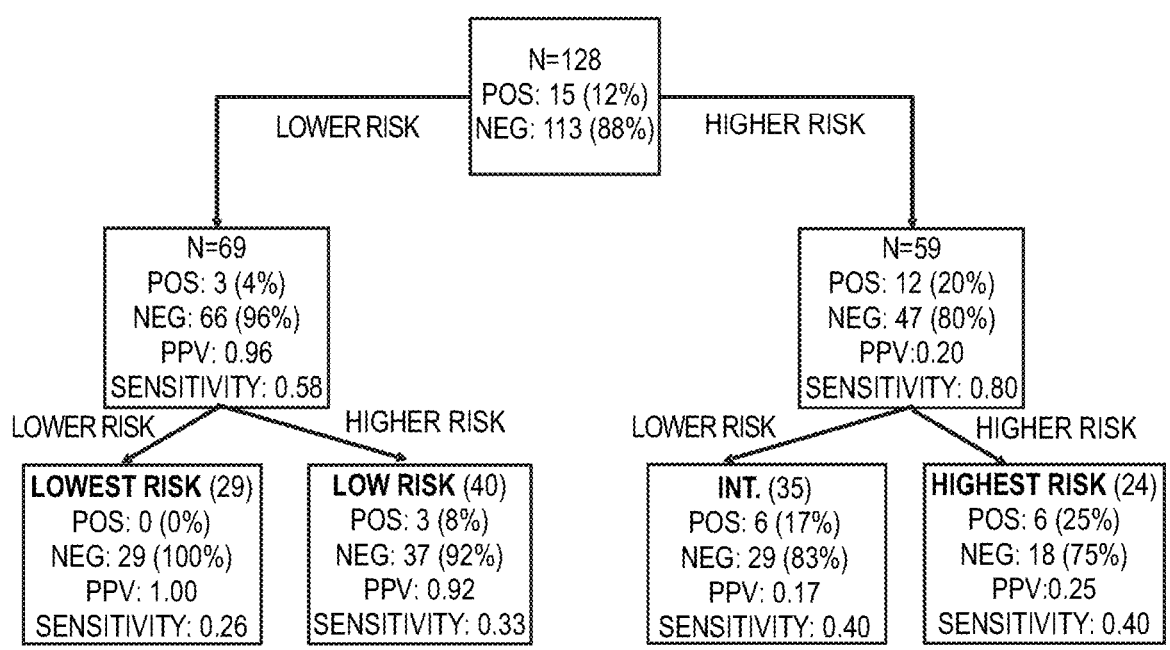
FIG. 27 is a chart showing the performance of a redeveloped Intubation test on the Brown data set.

FIG. 26 shows the results for the redeveloped intubation classifiers, namely the proportion of patients that were intubated (positive), the proportion not intubated (negative), precision, and recall in each relevant group for the risk of intubation. FIG. 27 gives the corresponding results of the redeveloped classifiers in the Brown set.

Tables 35 and 36, respectively, summarize selected categorical and continuous attributes by risk label. Mann-Whitney p-values are given comparing the median continuous attribute between the highest and lowest risk groups compared to all other risk groups. All statistics in these tables were calculated using Matlab R2020b.

TABLE 36

Categorical Attributes by Risk Label

| Attribute | Class | Lowest (N = 29) n (proportion of group) | Low (N = 40) n (proportion of group) | High (N = 35) n (proportion of group) | Highest (N = 24) n (proportion of group) |
|---|---|---|---|---|---|
| Pt_Ethnicity | | | | | |
| | Hispanic or Latino | 7 (0.24) | 9 (0.23) | 17 (0.49) | 7 (0.29) |
| | Not Hispanic or Latino | 21 (0.72) | 30 (0.75) | 18 (0.51) | 17 (0.71) |
| | Patient Refused | 1 (0.03) | 1 (0.03) | 0 (0.00) | 0 (0.00) |
| Pt_FirstRace | | | | | |
| | Black or African American | 4 (0.14) | 1 (0.03) | 9 (0.26) | 8 (0.33) |
| | Other | 8 (0.28) | 8 (0.20) | 15 (0.43) | 8 (0.33) |
| | Patient Refused | 1 (0.03) | 2 (0.05) | 0 (0.00) | 0 (0.00) |
| | White or Caucasian | 16 (0.55) | 29 (0.73) | 11 (0.31) | 8 (0.33) |
| Pt_Sex | | | | | |
| | Female | 20 (0.69) | 23 (0.58) | 11 (0.31) | 7 (0.29) |
| | Male | 9 (0.31) | 17 (0.43) | 24 (0.69) | 17 (0.71) |
| eGFR | | | | | |
| | 30 >= x > 60 | 6 (0.21) | 12 (0.30) | 3 (0.09) | 12 (0.50) |
| | >60 | 23 (0.79) | 25 (0.63) | 28 (0.80) | 7 (0.29) |
| | x < 30 | 0 (0.00) | 3 (0.07) | 4 (0.11) | 5 (0.21) |
| hypotension | | | | | |
| | 0 | 26 (0.90) | 37 (0.93) | 30 (0.86) | 17 (0.71) |
| | 1 | 3 (0.10) | 3 (0.07) | 5 (0.14) | 7 (0.29) |
| hypothermia | | | | | |
| | 0 | 28 (0.97) | 29 (0.73) | 35 (1.00) | 23 (0.96) |
| | 1 | 1 (0.03) | 11 (0.28) | 0 (0.00) | 1 (0.04) |
| hypox | | | | | |
| | 0 | 9 (0.31) | 7 (0.18) | 6 (0.17) | 2 (0.08) |
| | 1 | 20 (0.69) | 33 (0.83) | 29 (0.83) | 22 (0.92) |
| objective_fever | | | | | |
| | 0 | 15 (0.52) | 30 (0.75) | 2 (0.06) | 8 (0.33) |
| | 1 | 14 (0.48) | 10 (0.25) | 33 (0.94) | 16 (0.67) |

TABLE 36-continued

| | | Categorical Attributes by Risk Label | | | |
|---|---|---|---|---|---|
| Attribute | Class | Lowest (N = 29) n (proportion of group) | Low (N = 40) n (proportion of group) | High (N = 35) n (proportion of group) | Highest (N = 24) n (proportion of group) |
| supp_o2 | | | | | |
| | 0 | 14 (0.48) | 11 (0.28) | 7 (0.20) | 3 (0.13) |
| | 1 | 15 (0.52) | 29 (0.73) | 28 (0.80) | 21 (0.88) |
| tachycardia | | | | | |
| | 0 | 16 (0.55) | 23 (0.58) | 13 (0.37) | 9 (0.38) |
| | 1 | 13 (0.45) | 17 (0.43) | 22 (0.63) | 15 (0.63) |
| tachypnea | | | | | |
| | 0 | 13 (0.45) | 16 (0.40) | 5 (0.14) | 1 (0.04) |
| | 1 | 16 (0.55) | 24 (0.60) | 30 (0.86) | 23 (0.96) |

TABLE 36

| | Continuous Attributes by Risk Label | | | | |
|---|---|---|---|---|---|
| Attribute | Label | nMissing | Median | 25th Percentile | 75th Percentile | Mann-Whitney p |
| BMI_Value_N | Lowest | 0 | 31 | 27 | 36 | 0.293 |
| | Low | 0 | 30 | 27 | 34 | |
| | High | 0 | 30 | 27 | 34 | |
| | Highest | 0 | 29 | 27 | 34 | 0.772 |
| BUN | Lowest | 0 | 11 | 9 | 16 | <0.001 |
| | Low | 0 | 16 | 12 | 25 | |
| | High | 0 | 13 | 11 | 18 | |
| | Highest | 0 | 33 | 26 | 58 | <0.001 |
| CO2 | Lowest | 0 | 25 | 23 | 26 | 0.590 |
| | Low | 0 | 25 | 23 | 26 | |
| | High | 0 | 25 | 22 | 26 | |
| | Highest | 0 | 24 | 20 | 27 | 0.611 |
| CRP | Lowest | 0 | 22 | 9.1 | 51 | <0.001 |
| | Low | 0 | 130 | 86 | 200 | |
| | High | 0 | 92 | 39 | 160 | |
| | Highest | 0 | 160 | 100 | 290 | <0.001 |
| Calcium | Lowest | 0 | 8.8 | 8.6 | 9.4 | 0.407 |
| | Low | 0 | 8.8 | 8.4 | 9.1 | |
| | High | 0 | 8.7 | 8.4 | 9.1 | |
| | Highest | 0 | 9.1 | 8.4 | 9.5 | 0.192 |
| Creatinine | | | | | | |
| | Lowest | 0 | 0.78 | 0.63 | 1.1 | 0.004 |
| | Low | 0 | 0.9 | 0.67 | 1.2 | |
| | High | 0 | 0.94 | 0.8 | 1.1 | |
| | Highest | 0 | 1.5 | 1.1 | 1.9 | <0.001 |
| DDimer_Level | Lowest | 20 | 210 | 140 | 410 | 0.057 |
| | Low | 29 | 340 | 250 | 690 | |
| | High | 27 | 250 | 220 | 340 | |
| | Highest | 11 | 490 | 380 | 710 | 0.020 |
| Ferritin | Lowest | 11 | 310 | 140 | 430 | <0.001 |
| | Low | 12 | 500 | 290 | 1200 | |
| | High | 15 | 700 | 400 | 880 | |
| | Highest | 5 | 1100 | 840 | 2600 | <0.001 |
| LDH | Lowest | 4 | 230 | 160 | 260 | <0.001 |
| | Low | 6 | 310 | 260 | 370 | |
| | High | 11 | 300 | 220 | 370 | |
| | Highest | 5 | 380 | 290 | 500 | 0.002 |
| Platelets | Lowest | 0 | 190 | 130 | 250 | 0.865 |
| | Low | 0 | 210 | 170 | 240 | |
| | High | 0 | 190 | 150 | 250 | |
| | Highest | 0 | 180 | 130 | 300 | 0.632 |
| Potassium | Lowest | 0 | 3.7 | 3.5 | 3.9 | 0.264 |
| | Low | 0 | 3.9 | 3.5 | 4.3 | |
| | High | 0 | 3.7 | 3.4 | 3.8 | |
| | Highest | 0 | 4.1 | 3.5 | 4.4 | 0.107 |
| Pt_Age_AtIndex | Lowest | 0 | 56 | 41 | 68 | 0.016 |
| | Low | 0 | 61 | 54 | 79 | |
| | High | 0 | 59 | 54 | 64 | |
| | Highest | 0 | 66 | 58 | 73 | 0.090 |

TABLE 36-continued

Continuous Attributes by Risk Label

| Attribute | Label | nMissing | Median | 25th Percentile | 75th Percentile | Mann-Whitney p |
|---|---|---|---|---|---|---|
| WBC | Lowest | 0 | 5.3 | 3.6 | 6.2 | <0.001 |
|  | Low | 0 | 7 | 5.3 | 9.3 |  |
|  | High | 0 | 6.9 | 5.1 | 9.3 |  |
|  | Highest | 0 | 7.9 | 4.6 | 10 | 0.226 |
| sodium | Lowest | 0 | 130 | 130 | 140 | 0.214 |
|  | Low | 0 | 140 | 130 | 140 |  |
|  | High | 0 | 140 | 130 | 140 |  |
|  | Highest | 0 | 140 | 130 | 140 | 0.514 |

Discussion

While the Brown set was not complete in the attributes used to develop the original classifiers, the attributes that were present contained enough predictive information for both the imputation and redevelopment approaches to lead to decently performing tests. Performance had both similarities and differences to both what was observed in the development set for the two approaches and the performance of the original classifiers on the development set and validation set. The percentage of patients that experienced poor outcome increased across the risk groups from Lowest to Highest, as was seen before. The increase in proportion of patients that did not experience poor outcome in the Lowest risk groups was as good or even better than was previously observed. However, the increase in proportion of patients that experience poor outcome in the Highest risk groups was not as good as previously observed. This could be due in part to the lower incidence of poor outcome events in the Brown set compared to the development set, similar to what was observed in the original validation set. It is possible that this may also be due in part to the reduction in information content from the binarized ED attributes. This hypothesis is consistent with the larger degradation of performance in the ICU admission test, which was observed in the original Shapley value analysis to frequently rely on those attributes strongly in predicting risk.

While the set was relatively small and hypothesis testing for trends was not performed, qualitatively, we observed similar patterns in positive predictive value (PPV) and recall across the risk groups of the tests. Analysis of attribute association with risk group yielded similar results in both approaches to what was observed in the original development and validation studies.

While the imputation approach did use the originally trained classifiers, the resulting tests are still not identical to the original ones, and thus this study is not intended to be a further validation of the original tests. (Appendix A of our prior provisional application, Ser. No. 63/125,527 sets forth validation of the classifiers of this disclosure) However, the performance of the imputation approach still lends credence to the ability of the original classifiers to generalize to unseen data. Furthermore, the redevelopment approach results demonstrate the ability of the classifier development procedure itself to produce tests that generalize well to unseen data. This work also illustrates how the tests of this disclosure can be used to make predictions for a patient whose health record may be missing one or more attributes (using for example the imputation approach) and also that a suite of classifiers could be developed using our redevelopment approach such that the classifiers are developed from a data set which attributes which match those of the patient, or are binarized in accordance findings in the patient's health record, and so forth.

CONCLUSION

We have disclosed methods for generating predictions of a risk of unfavorable outcome for a hospitalized COVID-19 patient. We have also disclosed related computer systems implementing the method. It is contemplated that the methods can be generalized to generating classifiers trained to predicting risk of unfavorable outcomes for hospitalized patients in other disease contexts. Specifically, a method has been described developing a classifier for predicting risk of an unfavorable outcome of a patient admitted to a hospital, which includes steps of:

a) obtaining a development set comprising data from records for a multitude of patients admitted to one or more hospitals, wherein the data includes laboratory data, findings obtained at admission, basic patient characteristics, and clinical data including data indicating whether or not the unfavorable outcome occurred during hospitalization of the patients;

b) training an initial binary classifier from the development set to stratify members of the development set into high and low risk groups;

c) training child classifiers to further stratify high and low risk groups into at least highest and lowest risk groups; and d) configuring a test for predicting risk of unfavorable outcome as a hierarchical combination of the initial binary classifier and the child classifiers. The initial binary classifier is configured as a combination of a trained classification decision tree and a logistical combination of atomic classifiers with drop-out regularization, and the child classifiers are configured as a logistical combination of atomic classifiers with drop-out regularization.

Accordingly, while in one illustrated embodiment the classifiers are trained to predict risk for COVID-19 patients, on the other hand, for example, the classifiers could be trained to predict risk of unfavorable outcomes of other types of patients, such as influenza patients and the classifiers are trained from a development set consisting of health record data including hospitalization outcome data, basic patient characteristics, findings obtained at admission, and laboratory data from a multitude of previously hospitalized influenza patients. In one specific embodiment, the attributes used for training the tree of the binary classifier take the form of age, race, weight, gender, and the output classification label produced by the logistical combination of atomic classifiers with drop-out regularization. As with the case with COVID-19 risk classifiers, missing attributes in the health record could be imputed or predicted from other data in the health record.

We claim:

1. A method for predicting an unfavorable outcome for a hospitalized COVID-19 patient, comprising the steps of:
   a) obtaining attributes from a health record for the patient comprising at least findings obtained at admission, basic patient characteristics and laboratory data,
   b) iteratively training each of a set of initial binary classifiers from a development set and child classifiers from development subsets comprising data obtained from records for a set of hospitalized COVID-19 patients including at least findings obtained at admission, basic patient characteristics, and laboratory data for each of such patient;
   c) supplying the attributes obtained in step a) to a classifier using the trained set of initial binary and child classifiers implemented in a programmed computer trained to predict a risk of the unfavorable outcome, wherein:
   1) the classifier is arranged as a hierarchical combination of (a) the initial binary classifier stratifying the patient into either a high risk group or a low risk group, and (b) the child classifiers further classifying the patient in a lowest risk group or a highest risk group depending how the initial binary classifier stratified the patient as either a member of the high risk or low risk group,
   2) the initial binary classifier is configured as a combination of a trained classification decision tree and a logistical combination of atomic classifiers with drop-out regularization; and
   3) the child classifiers are configured as a logistical combination of atomic classifiers with drop-out regularization; and
   generating an output specifying a predicted risk of the unfavorable outcome for the patient based on a risk group in which the patient is classified.

2. The method of claim 1, wherein the unfavorable outcome comprises at least one of ICU admission, acute respiratory distress syndrome, any complication, and intubation.

3. The method of claim 1, further comprising the step of predicting one or more missing attributes in the health record for the patient, and wherein step c) comprises supplying the attributes obtained in step a) and the predicted one or more missing attributes.

4. The method of claim 1, wherein the initial binary and child classifiers are developed from attributes which are inclusive of the attributes presented in the health record for the patient.

5. The method of claim 1, wherein the findings obtained at admission in step a) are in a binary format and wherein the initial binary and child classifiers are developed from attributes in the form of findings obtained at admission in the development set which are converted into the binary format.

6. The method of claim 1, wherein the attributes used for training the classification decision tree of step c) 2) comprise age, race, weight, gender, and the output classification label produced by the logistical combination of atomic classifiers with drop-out regularization.

7. A method for developing a classifier for predicting risk of an unfavorable outcome of a patient admitted to a hospital, comprising the steps of:
   a) obtaining a development set comprising data from records for a multitude of patients admitted to one or more hospitals, wherein the data includes laboratory data, findings obtained at admission, basic patient characteristics, and clinical data including data indicating whether or not the unfavorable outcome occurred during hospitalization of the patients;
   b) iteratively training an initial binary classifier from the development set to stratify members of the development set into high and low risk groups;
   c) iteratively training child classifiers to further stratify high and low risk groups into at least highest and lowest risk groups;
   d) supplying the development set to the classifier using the trained set of initial binary and child classifiers;
   e) configuring a test for predicting risk of unfavorable outcome as a hierarchical combination of the initial binary classifier and the child classifiers using characteristics from a portion of data in the development set, and
   wherein: 1) the initial binary classifier is configured as a combination of a trained classification decision tree and a logistical combination of atomic classifiers with drop-out regularization, and 2) the child classifiers are configured as a logistical combination of atomic classifiers with drop-out regularization; and
   f) generating an output of the test specifying a predicted risk of the unfavorable outcome on a risk group in which the characteristics from the portion of data in the development set is classified.

8. The method of claim 7, wherein the development set comprises data for a multitude of hospitalized influenza patients.

9. The method of claim 7, wherein, for the initial binary classifier, the attributes used for training the tree comprise age, race, weight, gender, and the output classification label produced by the logistical combination of atomic classifiers with drop-out regularization.

10. The method of claim 7, further comprising the step of predicting one or more missing attributes in the health record for the patients in the development set, and wherein step b) comprises supplying the attributes obtained in step a) and the predicted one or more missing attributes.

* * * * *